US012176073B2

(12) United States Patent
Vu et al.

(10) Patent No.: US 12,176,073 B2
(45) Date of Patent: Dec. 24, 2024

(54) MODELING RIBOSOME DYNAMICS TO OPTIMIZE HETEROLOGOUS PROTEIN PRODUCTION

(71) Applicant: NORTH CAROLINA STATE UNIVERSITY, Raleigh, NC (US)

(72) Inventors: Scott Khoi Vu, Raleigh, NC (US); Donald L. Bitzer, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 797 days.

(21) Appl. No.: 16/744,130

(22) Filed: Jan. 15, 2020

(65) Prior Publication Data
US 2020/0286578 A1 Sep. 10, 2020

Related U.S. Application Data

(63) Continuation of application No. 15/541,941, filed as application No. PCT/US2016/012398 on Jan. 6, 2016, now abandoned.

(60) Provisional application No. 62/100,417, filed on Jan. 6, 2015.

(51) Int. Cl.
| G16B 5/20 | (2019.01) |
| C12N 15/67 | (2006.01) |
| G01N 33/68 | (2006.01) |
| G16B 5/00 | (2019.01) |
| G16B 20/00 | (2019.01) |

(52) U.S. Cl.
CPC .............. *G16B 5/20* (2019.02); *C12N 15/67* (2013.01); *G01N 33/68* (2013.01); *G16B 5/00* (2019.02); *G16B 20/00* (2019.02)

(58) Field of Classification Search
CPC ............ G16B 5/20; G16B 5/00; G16B 20/00; G16B 25/10; G16B 40/00; C12N 15/67; G01N 33/68
See application file for complete search history.

(56) References Cited

U.S. PATENT DOCUMENTS
| 2005/0227301 A1 | 10/2005 | Glover et al. |
| 2006/0024679 A1 | 2/2006 | Voges |
| 2010/0160602 A1 | 6/2010 | Kohlhoff et al. |

OTHER PUBLICATIONS

Mitarai, Namiko, and Steen Pedersen. "Control of ribosome traffic by position-dependent choice of synonymous codons." Physical biology 10.5 (2013): 056011 (Year: 2013).*
JPO; Decision of Refusal for Japanese Patent Application No. 2017-554252 dated Jul. 7, 2020, 3 pages.
CIPO; Office Action for Canadian Patent Application No. 2,972,473 dated Jun. 30, 2021, 7 pages.
AUIP; Examination Report for Australian Patent Application No. 2016205254 dated Aug. 30, 2021, 3 pages.
CNIPA; Office Action for Chinese Patent Application No. 201680005182.9 dated Jul. 31, 2020, 22 pages.
IPI; Office Action for Indian Patent Application No. 201717025807 dated Jul. 30, 2020, 8 pages.
Siller, Efrain, et al., "Slowing Bacterial Translation Speed Enhances Eukaryotic Protein Folding Efficiency", Journal of Molecular Biology, 2010, vol. 396, pp. 1310-1318.
KIPO; Office Action for Korean Patent Application No. 10-2017-7021950 dated Jan. 28, 2022, 10 pages.
Gene-We Li et al., "the Anti-Shine Dalgramo Sequence Drives Translation Pausing and Codon Choice In Bacteria, Nature." Author manuscript; available in PMC Oct. 26, 2012, vol. 484 (7395), pp. 538-541.
International Search Report and Written Opinion dated May 12, 2016 from related International appliocation No. PCT/US2016/012398.
S. K. Vu et al., "Modeling Ribosome dynamics To Optimize Heterologous Protein Production in *Esherichia coli*," North Carolina State University, Global SIP14-Workshop on Genomic Signal Processing and Statistics, pp. 1422-1425 (2014).
Molinar et al., "A Real Time PCR Assay for Early Detection of Eastern Filbert Blight," AN 2013:943654 Caplus, DN 161:516911, American Phytopathological Society Journal 97(6), 813-818 (2013) (Abstract).
Gorissen et al., "Ribosome Dwell Times and the Protein Copy Number Distribution," AN 2012:1321386 Caplus, DN 159:738800, Journal of Statistical Physics 148(4), 627-635 (2012) (Abstract).
Gorissen et al., "Semi-Markov Models of mRNA Translation," AN 2011:447467 Caplus, DN 155:478165, Quantitative Biology (2011) 1-4, Cornell university Library, Apr. 2011 (Abstract).
Dethlefsen et al., "Codon bias In Highly Expressed Genes is Correlated with Ribosomal RNA Operon Copy Number in the Bacteria ," AN 2003:556216 Biosis, DN PREV200300556939, Abstracts of the General Meeting of the American Society for Microbiology, vol. 103, pp. R-056 (2003) (Abstract).
Chapin-Robertson et al., "Detection and Identification of *Myobacterium* Directly from BACTEC Bottles By Using a DNA-rRNA Probe," AN 1994:111417 Biosis, DN 1PREV199497124417, Diagnositc Biology and Infectious Disease, vol. 17. No. 3, pp. 203-207 (1993) (Abstract).
Kubyshikin et al., "On Universal Coding Events In Protein Biogenesis," AN 2018:369015 Biosis, DN PREV201800369015, Biosystems, vol. 164, pp. 16-25 (2018) (Abstract).
Yuan et al., "Controlling Multicycle Replication of Live-Attenuated HIV-1 Using an Unnatural Genetic Switch," AN 2017:126654 Caplus, DN 166:384057, ACS Synthetic Biology, 6(4), 721-731 (2017) (Absract).
Patil et al., "Increased tRNA Modification and Gene-Specific Codon Usage Regulate Cell Cycle Progression During the DNA Damage Response," AN 2012:724743 Biosis, DN PREV201200724723, Cell Cycle, vol. 11, No. 19, pp. 3656-3665 (Oct. 1, 2012) (Abstract).

(Continued)

*Primary Examiner* — Nancy J Leith
*Assistant Examiner* — Kyle T Rega
(74) *Attorney, Agent, or Firm* — NK Patent Law

(57) ABSTRACT

The presently disclosed subject matter provides a free-energy based model of translation elongation to predict and optimize heterologous gene expression. The model and software allow for the prediction and optimization of genes for increased or decreased protein yield and for increased or decreased protein aggregation.

6 Claims, 28 Drawing Sheets

Specification includes a Sequence Listing.

(56) References Cited

OTHER PUBLICATIONS

Chen et al., "Unraveling the Dynamics of Ribosome Translocation," AN 2013:136458 Biosis, DN PREV201300136458, Current Opinion in Structural Biology, vol. 22, No. 6, pp. 804-814 (Dec. 2012) (Abstract).

Frenkel-Morgenstern et al., "Genes Adopt Non-Optimal Codon Usage to Generate Cell-Cycle Dependent Oscillations in Protein Levels," AN 2912128079 Embase, DN 364362390, Molecular Systems Biology, vol. 8, am. 572 (2012) (Abstract).

Frenkel-Morgenstern et al., "Genes Adopt Non-Optimal Codon Usage to Generate Cell-Cycle Dependent Oscillations in Protein Levels," AN 2012:816776 Caplus, DN 159:711043, Molecular Systems Biology, vol. 8, 10 pages (2012) (Abstract).

Frenkel-Morgenstern et al., "Genes Adopt Non-Optimal Codon Usage to Generate Cell-Cycle Dependent Oscillations in Protein Levels," AN 2012:249702 Biosis, DN PREV201200249702, Molecular Systems Biology, vol. 8, Article No. 572 (2012) (Abstract).

Zouridis et al., "Effects of Codon Distributions and tRNA Competition On Protein Translation," AN 2008:569477 Biosis, DN PREV200800569476, Biophysical Journal, vol. 95, No. 3, pp. 1018-1033 (Aug. 1, 2008) (Abstract).

Moura et al., "Codon-Triplet Context Unveils Unique Features of the Candida Albicans Protein Coding Genome," AN 2008:542820 Caplus, DN 148:463865, BMC Genomics, No. 8 (2007) (Abstract).

Glover et al., "Cell Cycle Progression Genes and Proteins of *Drosophila melanogaster* and their Human Homologs and their Use for Prevention, Treatment and Diagnosis of Disease," AN 2004:606544 Caplus, DN 141:152214, PCT WO 2004063362 (Abstract).

Gnirke et al., "Large Scale Synthesis of a Messenger RNA Analogue," AN 1989:289458 Biosis, DN PREV198988014802, Biochemistry International, vol. 18, No. 3, pp. 551-560 (1989) (Abstract).

Liljenstroem et al., "The tRNA Cycle and Its Relation to the Rate of Protein Synthesis," European Biophysics Journal, No. 12(2), 115-119 (1985).

* cited by examiner

MODELING RIBOSOME DYNAMICS TO OPTIMIZE HETEROLOGOUS PROTEIN PRODUCTION

CROSS-REFERENCE TO RELATED APPLICATIONS

This application claims the benefit of U.S. Provisional Application No. 62/100,417, filed Jan. 6, 2015, the entire content of which is incorporated by reference herein in its entirety.

BACKGROUND

Translation is a biological process by which an organism produces specific polypeptides that fold into functional proteins [1,13]. Heterologous protein synthesis uses translation to produce proteins not normally produced in the host organism [2,3]. These proteins are used across a broad range of industrial applications, ranging from biofuel production to agriculture and biopharmaceuticals. Unfortunately, attempts to translate unmodified exogenous genes in production organisms, such as *Escherichia coli*, often result in low or no synthesis of the desired protein [1,2]. Some of the issues identified are poor translation, non-optimal ribosome binding site (RBS), RBS and start codon spacing, frameshifting, premature termination, and protein aggregation caused by misfolding of the protein [1,2]. Although maximizing protein yield has been studied in detail for some time, the underlying processes and effects of translation elongation on protein yield have not been resolved. For many years, the primary cause of low protein yield was thought to be simply codon bias and rare codons coding for rare aminoacyl-tRNA (aa-tRNA) [1,2,3]. Recent experimental evidence suggests that low protein yield may result from a number of equally important additional factors [4,5,6,7].

The current "standard" for determining protein yield is Sharpe's codon adaptation index (CAI) [8]. Sharpe's algorithm takes the codon usage from highly expressed genes as the standard for calculating CAI. Genes with similar codon usage as highly expressed genes score higher, with CAI ranging from 0 to 1. CAI can be used as a measure of a gene's codon bias relative to an organism's codon bias. Typically one would optimize yield by modifying the codon bias of a heterologous gene towards the codon bias of highly expressed genes of the production organism. Unfortunately, optimization using only CAI sometimes works, and sometimes does not [1,3].

It is suggested from the experiments of [4,5,6,7] that the determinants of low protein yield, or protein yield in general, may not only be from codon bias and rare tRNA availability, but from possibly equally important additional factors. For example, ribosomal profiling data from [6] suggest that the anti-Shine-Dalgarno (aSD) of the 3' terminal nucleotides of the 16S rRNA interacts with the mRNA during translation elongation to "pause" the ribosome. Li et al [6] observed little correlation between codon usage/tRNA abundance and ribosome translation speed. They propose that the yield from translation elongation is highly correlated with ribosome pausing at Shine-Dalgarno (SD) like sequences in the mRNA, and that the aSD of the 3' end 16S rRNA tail affects the "speed" of ribosomes translating the mRNA.

Without being bound by theory, the presently disclosed subject matter relates to the hypothesis that the ribosome is physically slightly displaced relative to the zero reading frame where ribosome pausing is observed. By being displaced, it takes the ribosome longer to acquire the next aa-tRNA. Second order effects from the free energy periodicity signal [9,10,11] and tRNA abundance information may be used to build a novel translation model for *E. coli* that incorporates this fractional displacement notion. Based on in vivo experiments, this model appears to have considerable predictive and optimizing power.

SUMMARY

The presently disclosed subject matter provides a free-energy based model of translation elongation to predict and optimize protein yield and aggregation. In one aspect, a method for predicting protein yield for translation of a gene is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) determining a total cycle count across codons throughout the coding region; wherein the total cycle count across codons throughout the coding region is correlated with protein yield.

In another aspect, a method for predicting protein yield for translation of a gene is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; (b) plotting a translation bottleneck plot, wherein the plot comprises values comprising a sum of cycles within a sliding window of size N codons; and (c) determining a maximum sum in the translation bottleneck plot; wherein the maximum sum in the translation bottleneck plot is correlated with protein yield.

In another aspect, a method for predicting protein yield for translation of a gene is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) performing a protein translation simulation to determine an amount of ribosomes that finish translation within a number of cycles; wherein the amount of ribosomes that finish translation within a number of cycles is correlated with protein yield.

In another aspect, a method for increasing protein yield for translation of a gene is provided, the method comprising: (a) performing any one of the methods for predicting protein yield for translation of a gene as described above; and (b) modifying codons using synonymous codons that conserve the protein amino acid sequence while changing the force and/or the wait time; wherein the protein yield for translation of the gene is increased. In further aspects, step (b) comprises modifying codons such that ribosome wait time is decreased. In further aspects, the ribosome displacement magnitude is minimized by selecting for a phase angle of the gene that is substantially equal to a species angle of the gene.

In another aspect, a method for decreasing protein yield for translation of a gene is provided, the method comprising: (a) performing any one of the methods for predicting protein yield for translation of a gene as described above; and (b) modifying codons using synonymous codons that conserve the protein amino acid sequence while changing the force and/or the wait time; wherein the protein yield for translation of the gene is decreased. In further aspects, step (b) comprises modifying codons such that ribosome wait time is decreased.

In another aspect, a method for predicting protein aggregation is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) determining a total cycle count across codons throughout the coding region; wherein the total cycle count across codons throughout the coding region is correlated with protein aggregation.

In another aspect, a method for predicting protein aggregation is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome: (b) plotting a translation bottleneck plot, wherein the plot comprises values comprising a sum of cycles within a sliding window of size N codons; and (c) determining a maximum sum in the translation bottleneck plot; wherein the maximum sum in the translation bottleneck plot is correlated with protein aggregation.

In another aspect, a method for predicting protein aggregation is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) performing a protein translation simulation to determine an amount of ribosomes that finish translation within a number of cycles; wherein the amount of ribosomes that finish translation within a number of cycles is correlated with protein aggregation.

In another aspect, a method for increasing protein aggregation is provided, the method comprising: (a) performing any one of the methods for predicting protein aggregation as described above; and (b) modifying codons using synonymous codons that conserve the protein amino acid sequence while changing the force and/or the wait time; wherein protein aggregation is increased. In further aspects, step (b) comprises modifying codons such that ribosome wait time is decreased.

In another aspect, a method for decreasing protein aggregation, the method comprising: (a) performing any one of the methods for predicting protein aggregation as described above; and (b) modifying codons using synonymous codons that conserve the protein amino acid sequence while changing the force and/or the wait time; wherein protein aggregation is decreased. In further aspects, step (b) comprises modifying codons such that ribosome wait time is decreased.

In another aspect, any of the methods disclosed herein are provided, wherein the gene is from a prokaryotic organism and the 3' terminal rRNA tail of the ribosome is a 16S rRNA tail. In another aspect, any of the methods disclosed herein are provided, wherein the gene is from a eukaryotic organism and the 3' terminal rRNA tail of the ribosome is an 18S rRNA tail.

In a further aspect, a computer readable medium is provided, programmed to perform one or more of any of the method steps disclosed herein.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Having thus described the presently disclosed subject matter in general terms, reference will now be made to the accompanying Figures, which are not necessarily drawn to scale.

Figure 1:
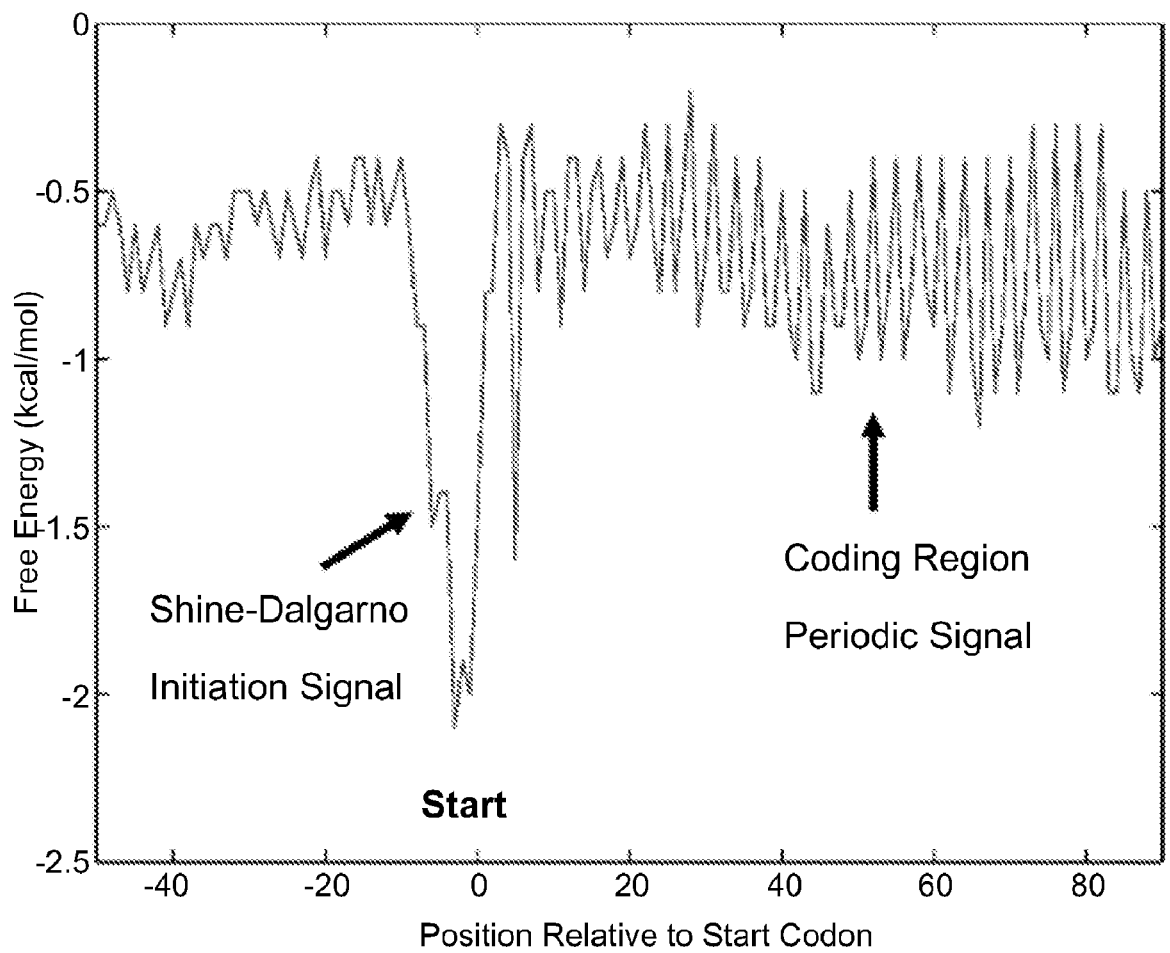

FIG. 1. Plot of the average free energy signal. This signal is obtained by calculating hybridization energy at every nucleotide for 200 non-frame-shifting *E. coli* genes with length greater than 1000 nucleotides.

Figure 2:
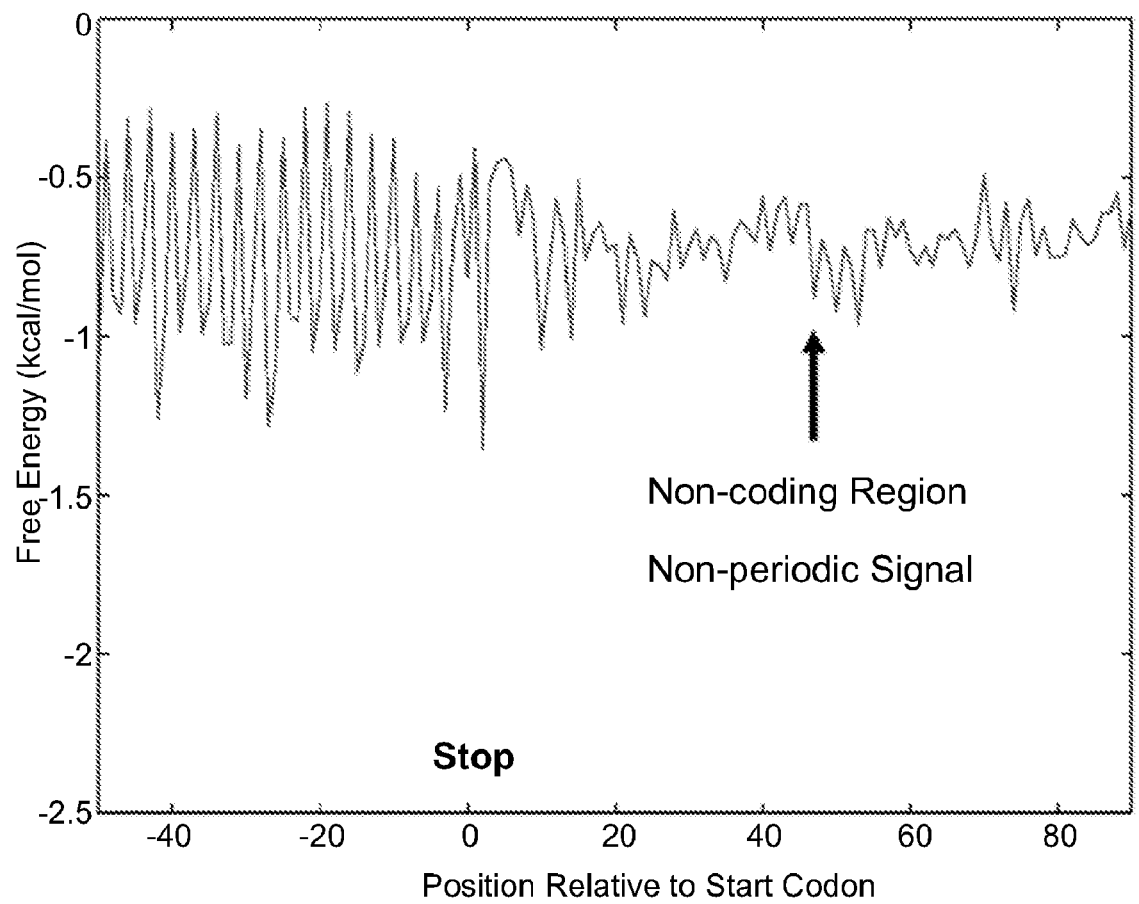

FIG. 2. Plot of the average signal post stop codon. This signal is also obtained by calculating hybridization energy of 200 non-frame-shifting *E. coli* endogenous genes after the stop codon of the open reading frames.

Figure 3:
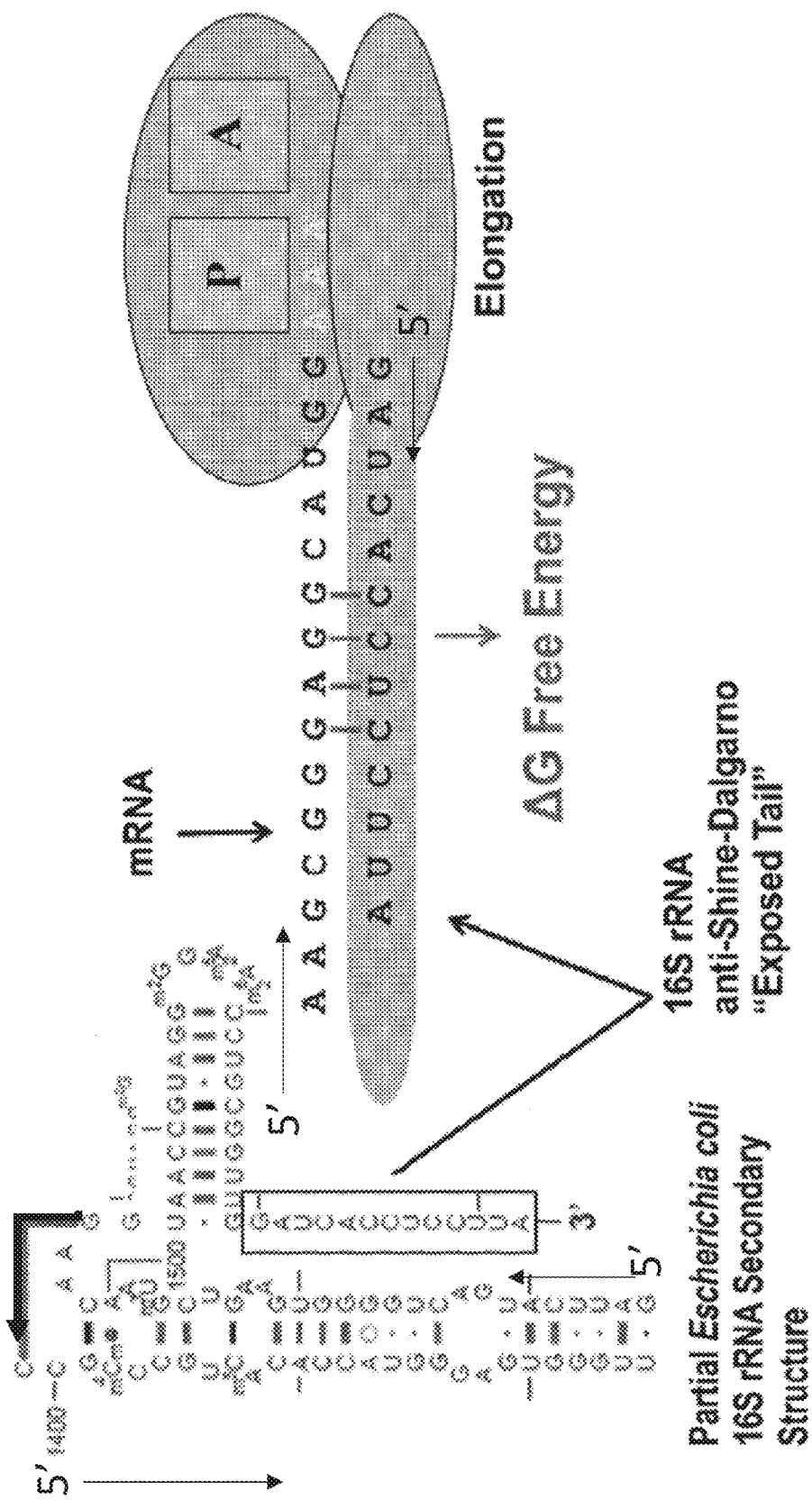

FIG. 3. Interactions between ribosomal tail and mRNA. The 16S sRNA "exposed tail" continuously interacts with the mRNA during translation elongation for which the free energy from the Watson and Crick binding can be calculated FIG. 3 discloses SEQ ID NOS 13-16, respectively, in order of appearance.

Figure 4:
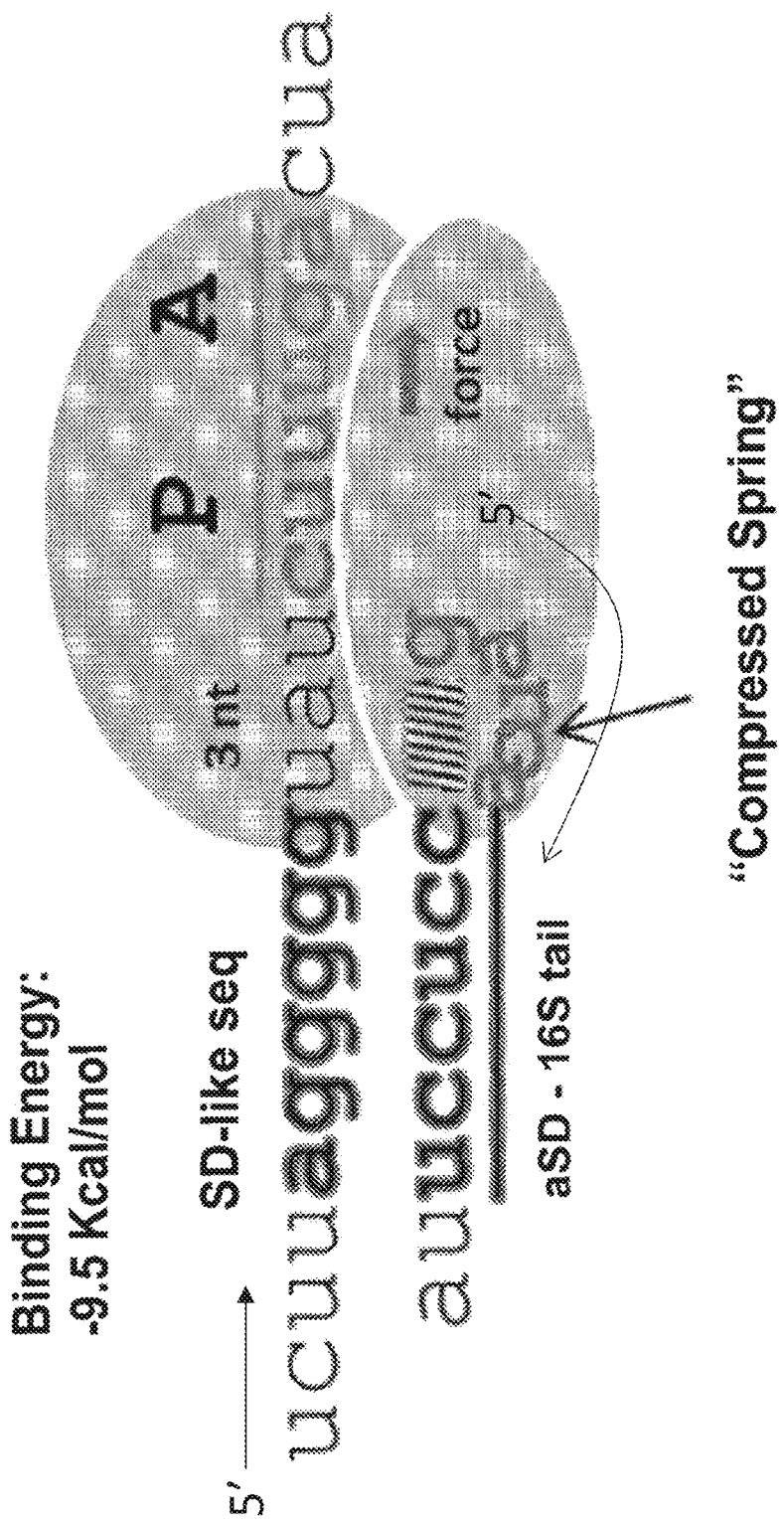

FIG. 4. Physical illustration during translation of prfB at frameshift site, codon 26. FIG. 4 discloses SEQ ID NOS 5 and 16, respectively in order of appearance. The aSD of 16S "exposed tail" binds too close, 3 nucleotides, to the P-site at codon 26 (stop) and compresses the "spring" that displaces ribosome towards +1 reading frame. The simulation illustration is depicted in FIG. 5.

Figure 5:
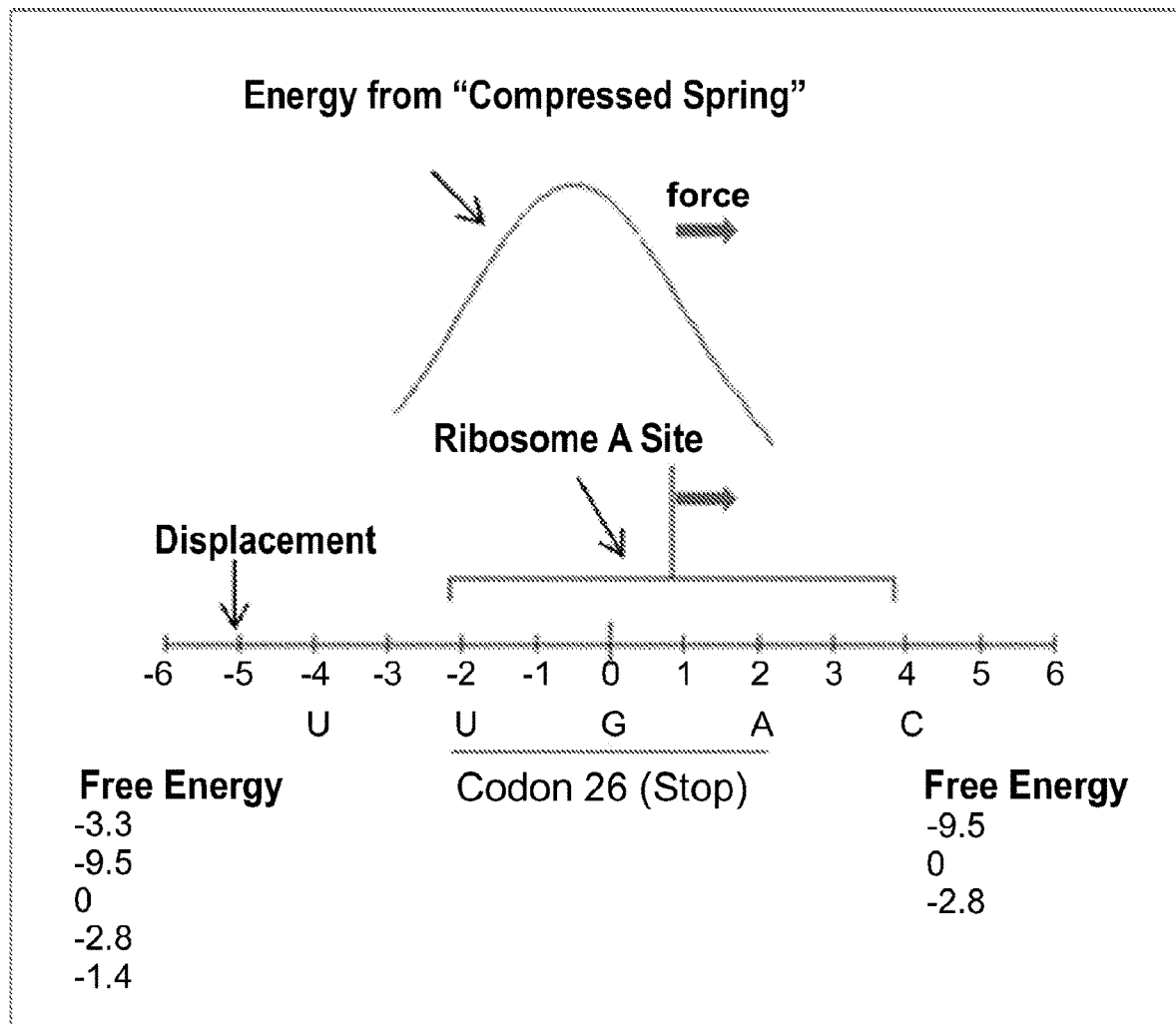

FIG. 5. Simulation illustration during translation of prfB at frameshift site, codon 26. The energy from compressed spring is shown. This energy is calculated from the free energy resulting from the binding between the SD-like sequence on the mRNA and the aSD of 16S "exposed tail". The binding compresses the "spring" that displaces ribosome towards minimal energy in +1 reading frame.

Figure 6:
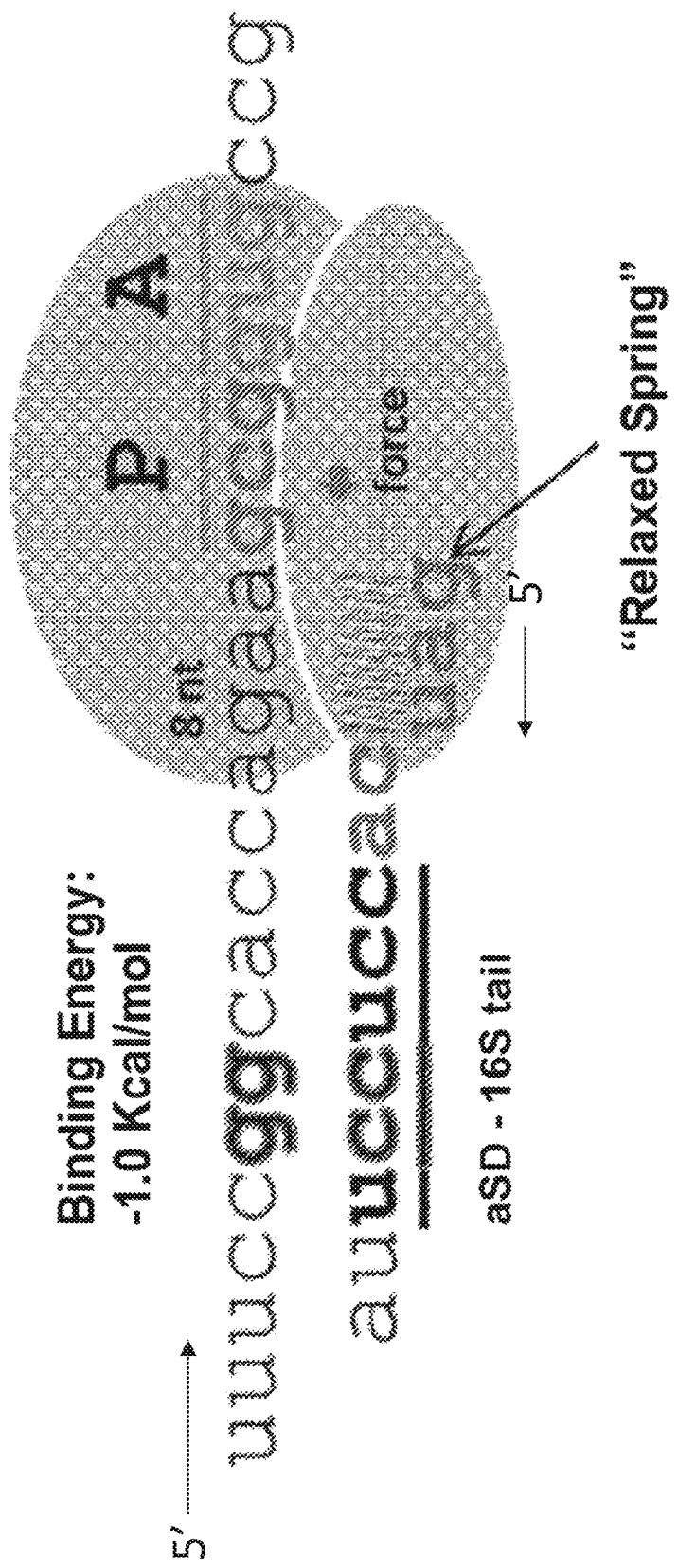

FIG. 6. Physical illustration during translation of lacZ at codon 70. FIG. 6 discloses SEQ ID NOS 6 and 16, respectively, in order of apperance. The aSD binds 8 nucleotides from the P-site resulting in a "relaxed spring" with little to no ribosome displacement. The distance between the aSD to the P-site is 5 bases. The simulation illustration is depicted in FIG. 7.

Figure 7:
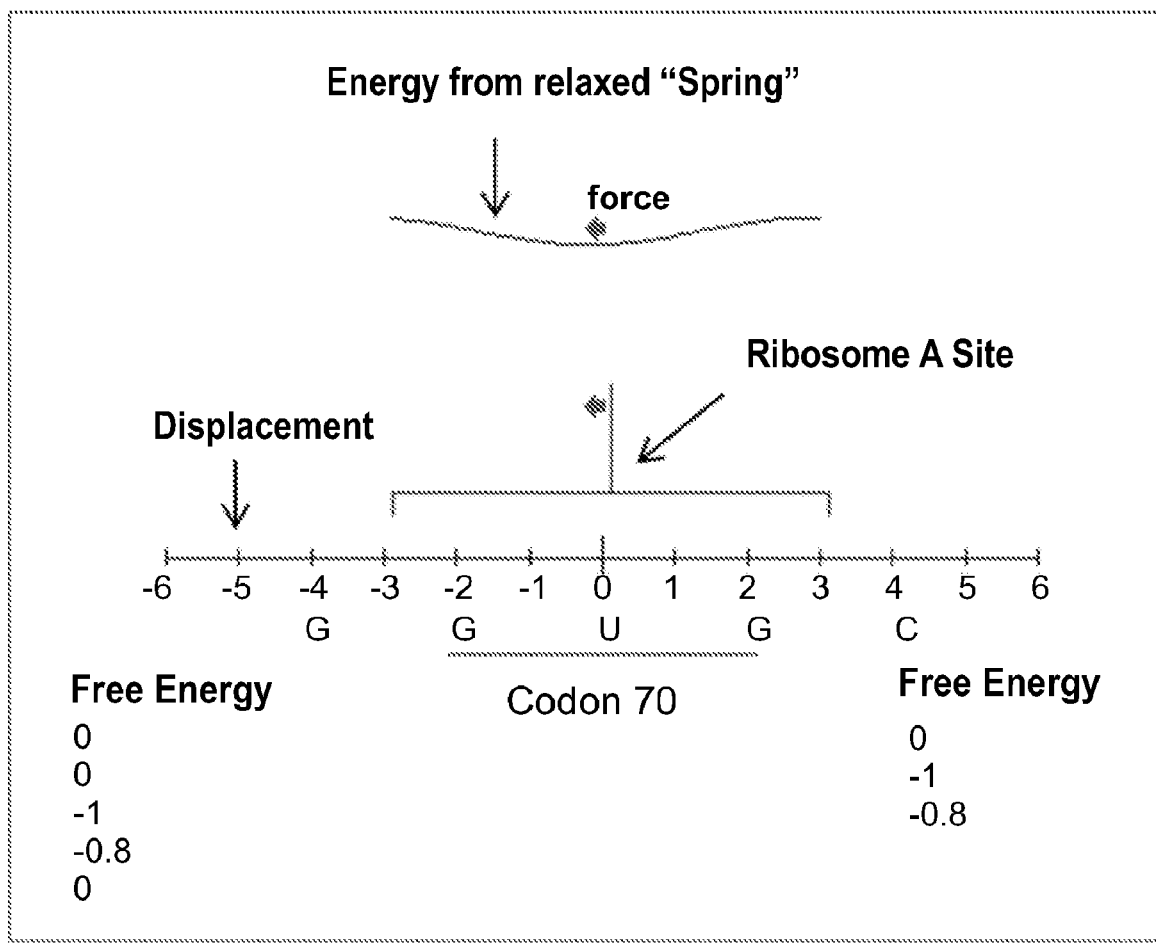

FIG. 7. Simulation illustration during translation of lacZ at codon 70. The energy from a relaxed spring is shown. This energy is calculated from the free energy resulting from the binding between the mRNA and the aSD of 16S "exposed tail". The aSD binds 8 nucleotides from the P-site resulting in a "relaxed spring" with little to no ribosome displacement.

Figure 8:
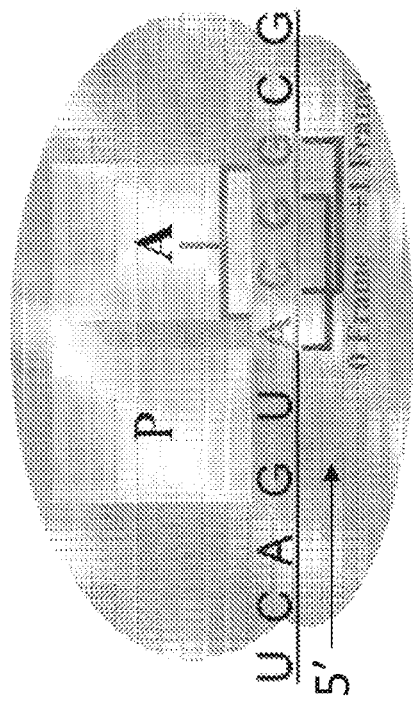
Figure 8:
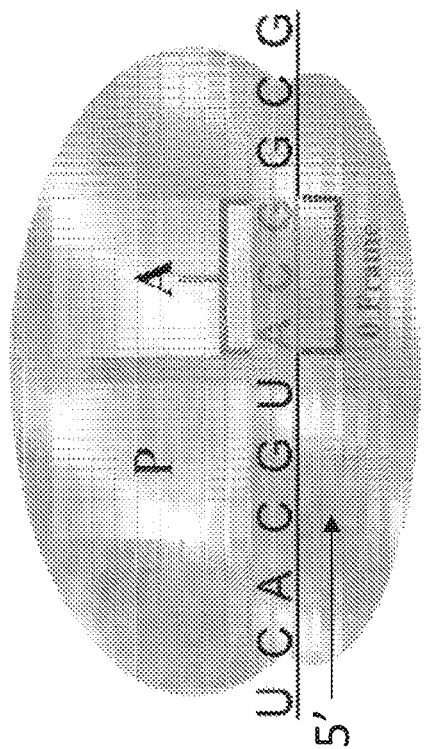

FIG. 8. Displaced vs non-displaced ribosome. Left) Illustration of a non-displaced ribosome; the A-site is in perfect alignment with the 0 reading frame. FIG. 8 discloses SEQ ID NOS 7-8 respectively in order of appearance. Right) Illustration of a displaced ribosome between the 0 reading frame and +1 reading frame resulting in a misalignment. The A-site sees both the codon in the 0 reading frame and +1 reading frame and is capable of picking up the aminoacyl-tRNA in either reading frame. In this example, the ribosome can pick up either the aa-tRNA coded by ACG codon or aa-tRNA coded by CGG codon.

Figure 9:
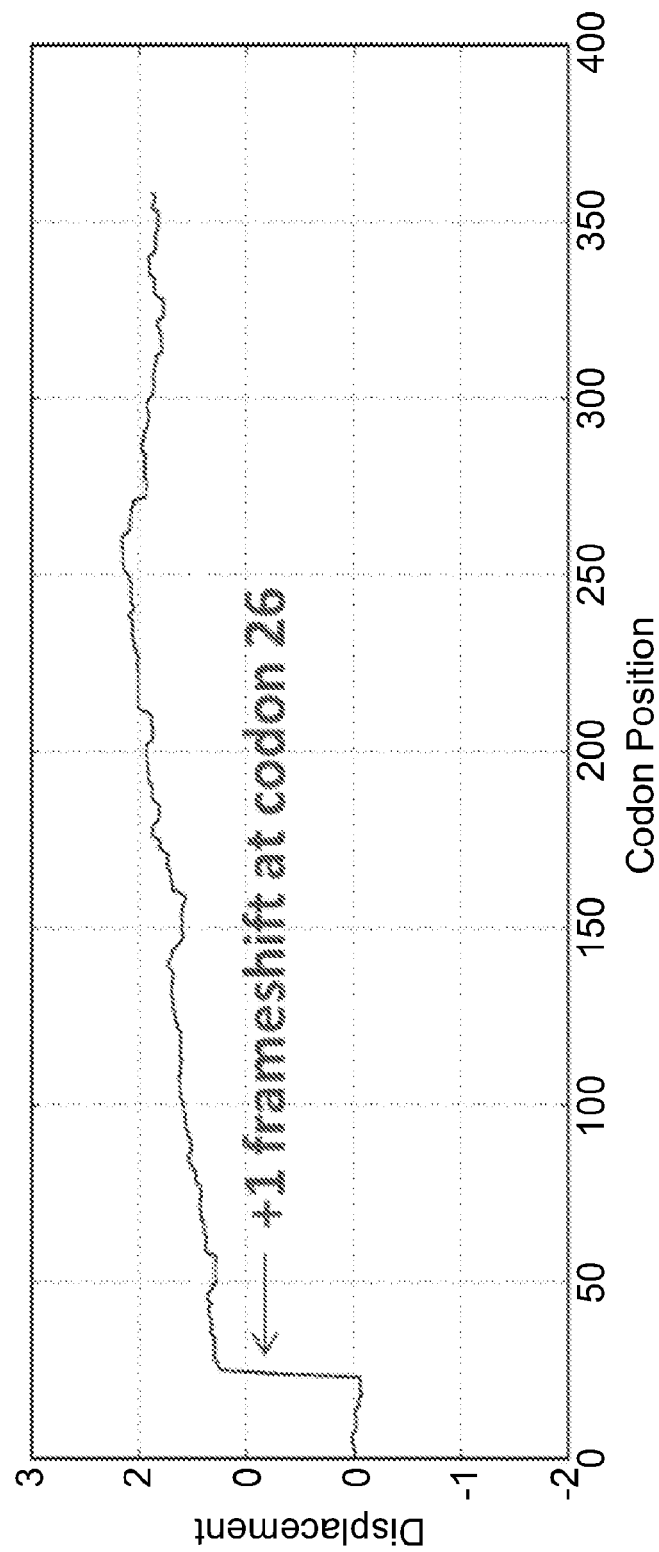

FIG. 9. Ribosome displacement plot of prfB during translation elongation. Displacement shifts towards +2 displacement units (1 nucleotide) at the frameshift site (codon 26) indicating a +1 frameshifting event.

Figure 10:

FIG. 10. Ribosome wait time plot of prfB during translation elongation. High ribosome wait time of 147 cycles at codon 26 indicates the ribosome pauses at the frameshift site. This illustrates that ribosome displacement (FIG. 4.9) contributes to ribosome wait time.

Figure 11:
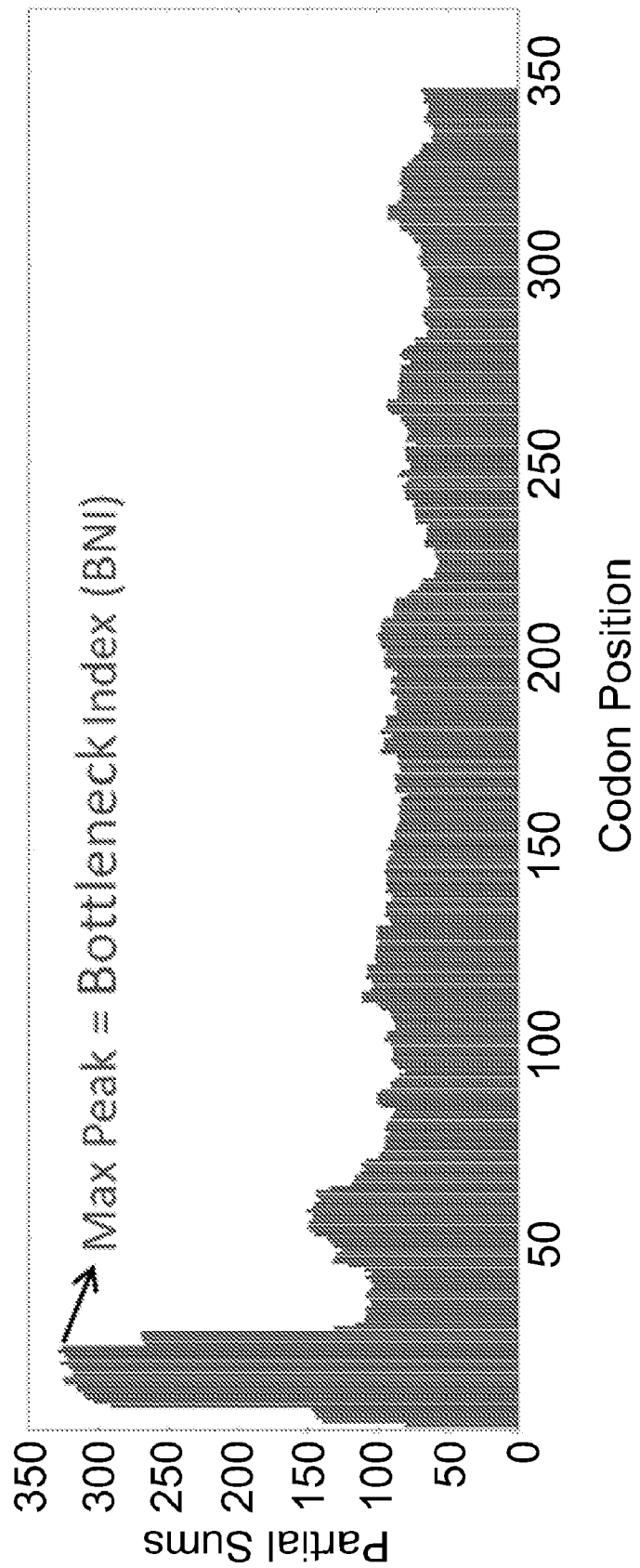

FIG. 11. Translation bottleneck plot of prfB throughout translation elongation. High ribosome wait time at frameshift site due to ribosome frameshifting produces a bottleneck of 329 at codon 26.

Figure 12:
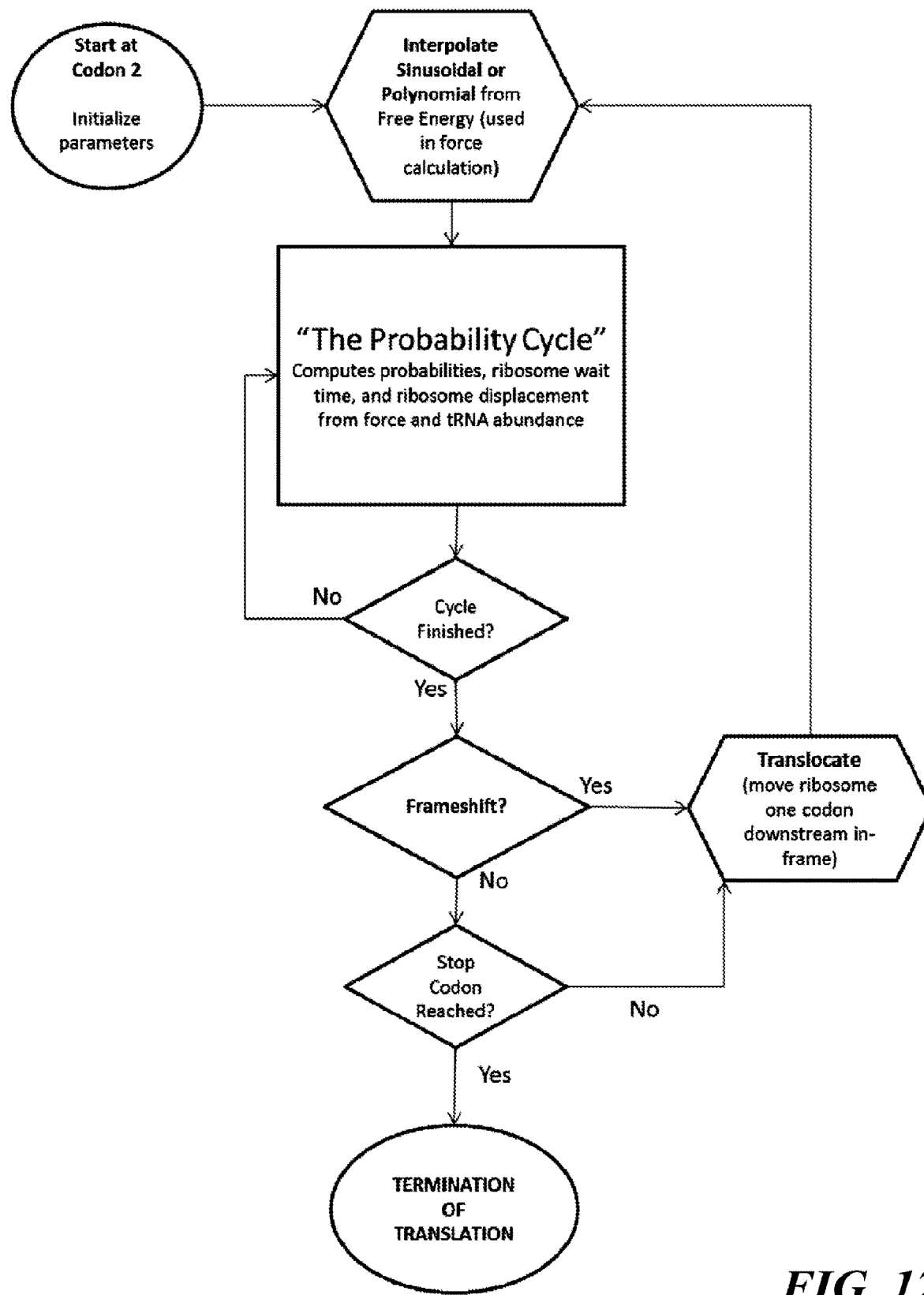

FIG. 12. Flow chart of the main algorithm. The main algorithm starts with codon 2 in the A-site. Force is computed from free energy signal. The probability cycle executes to determine ribosome displacement at each codon. After picking up an aa-tRNA, the ribosome either frameshifts then translocates or performs regular in-frame translocation. If a stop codon is recognized, the main algorithm terminates ribosome translation simulation.

Figure 13:
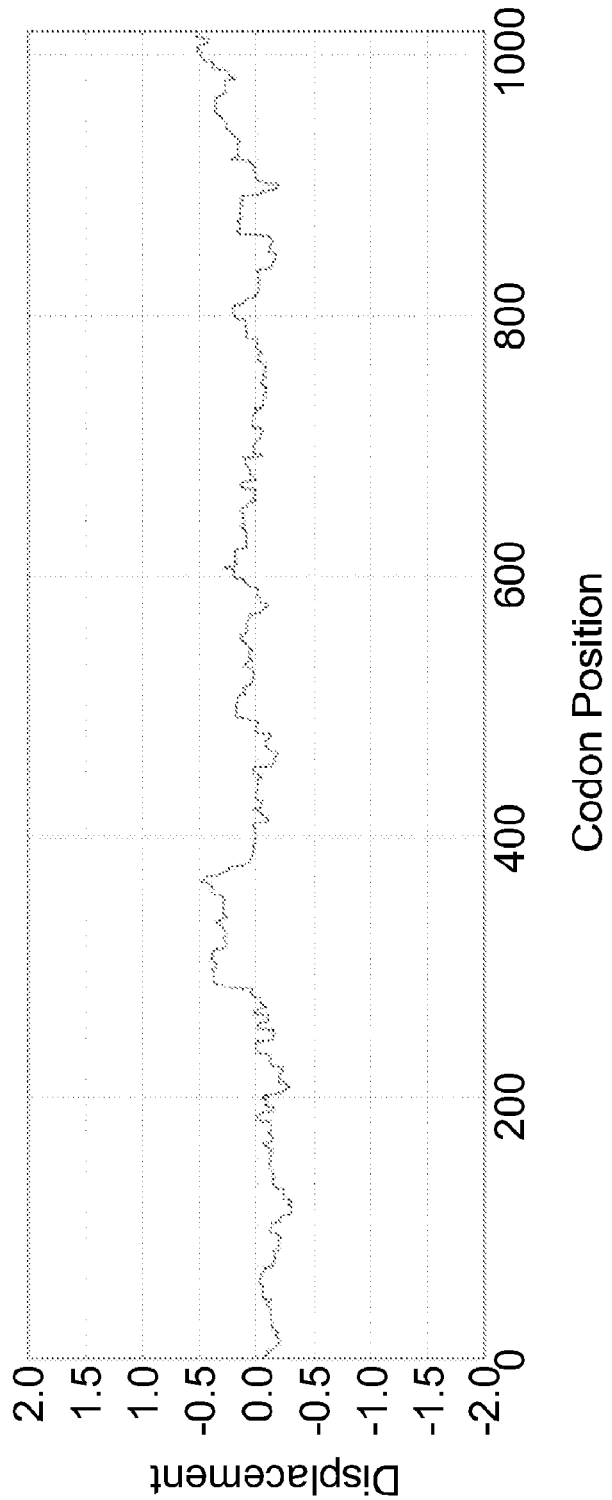

FIG. 13. Ribosome displacement plot of lacZ. This plot is generated as the algorithm progresses through each cycle and outputs a value for ribosome displacement at each codon position.

Figure 14:
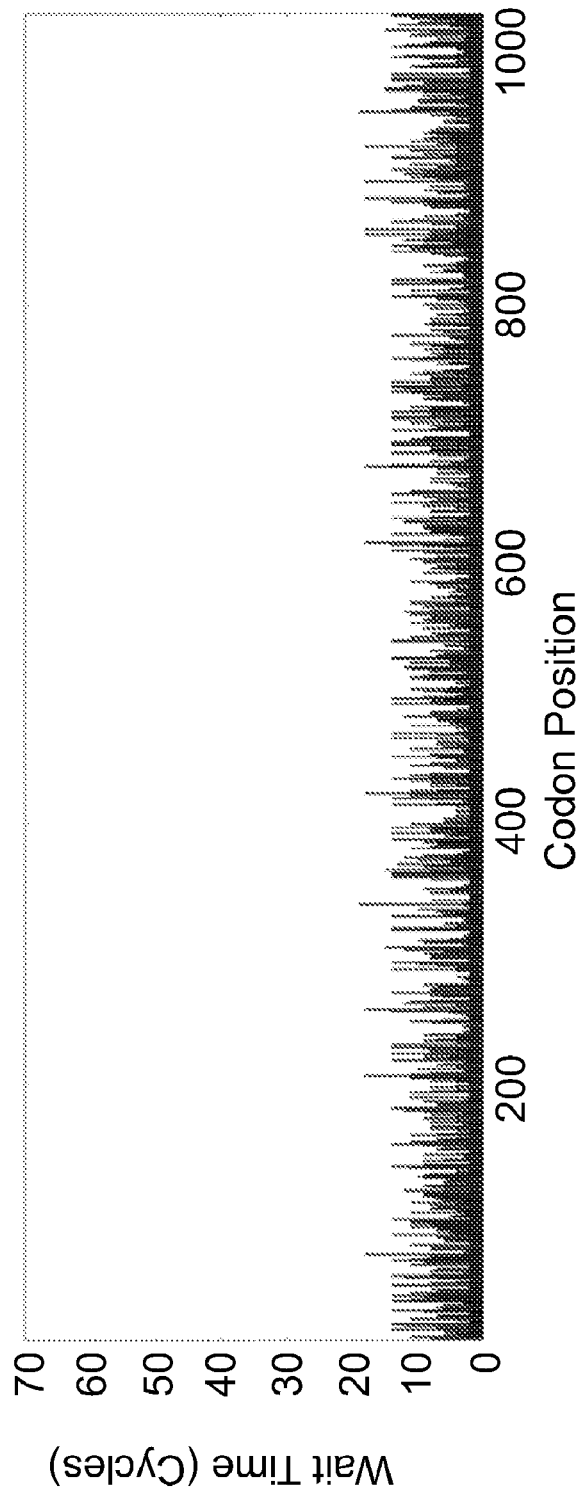

FIG. 14. Ribosome wait time plot of lacZ. This plot is generated as the number of cycles required for the ribosome to "pick up" an aa-tRNA at each codon position.

Figure 15:
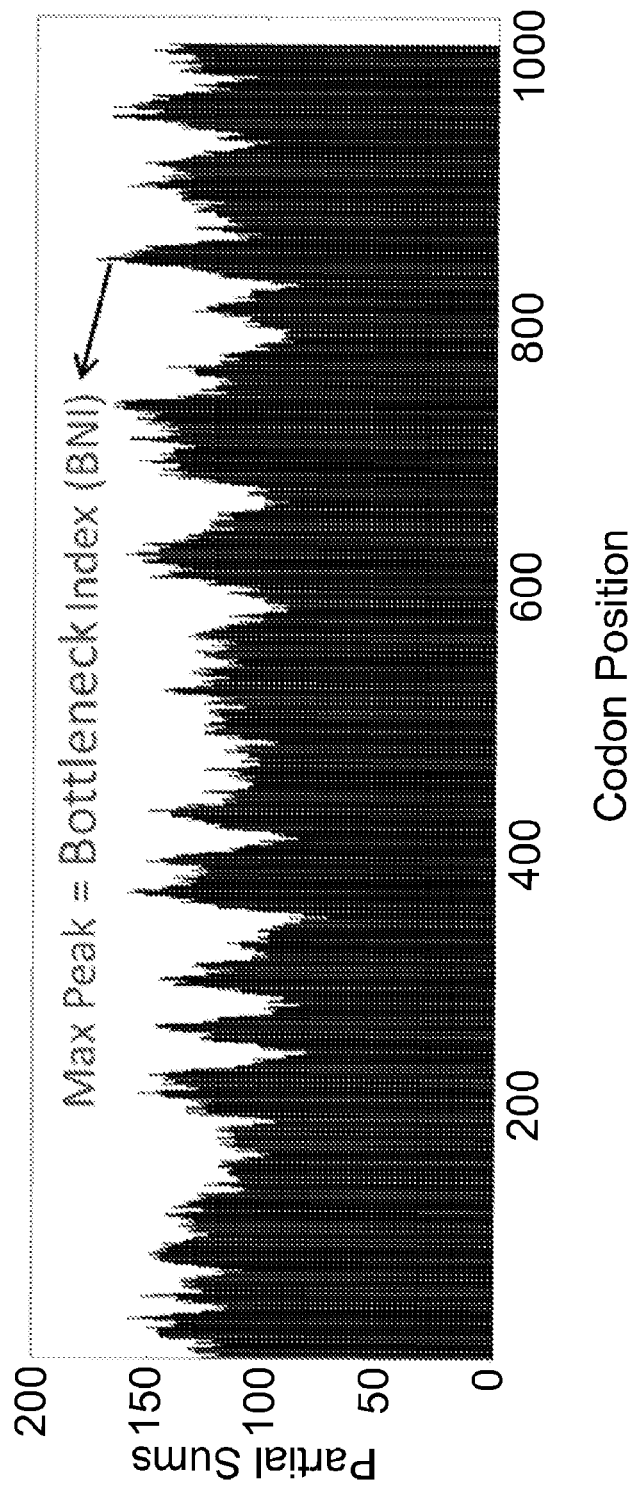

FIG. 15. Translation bottleneck plot of lacZ during translation elongation. Illustrates the partial sums using a sliding window size of 20 codons. Bottleneck (BNI) is 174 at codon 839.

Figure 16:
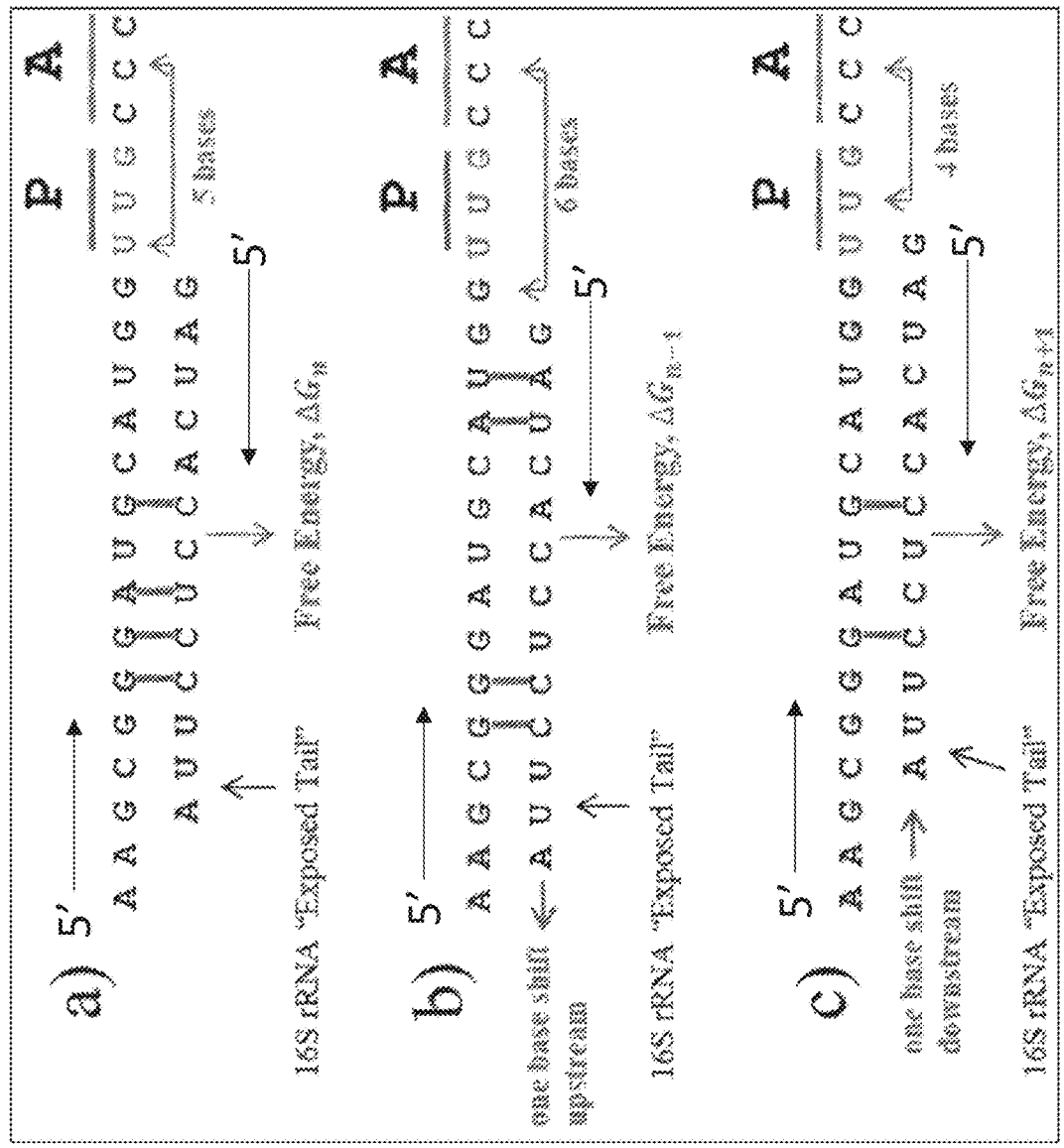

FIG. 16. Variation in free energy based on tail mRNA spacing. (a) Free energy value ($\Delta G_n$) is calculated from the binding between the 16S rRNA exposed tail and the mRNA 5 bases away from the center of the A-site. (b) Free energy value ($\Delta G_{n-1}$) is calculated from 16S rRNA exposed tail: mRNA binding 6 bases away from the center of the A-site, or a one base shift upstream from $\Delta G_n$ binding position. (c) Free energy value ($\Delta G_{n+1}$) is calculated from the binding between 16S rRNA exposed tail and mRNA 4 bases away from the center of the A-site, or one base shift downstream relative to the $\Delta G_n$ binding position. Free energy calculation is described in Appendix A. FIG. 16 discloses SEQ ID NOS 9, 16, 9, 16, 9, and 16, erspectivelly, in order of appearance.

Figure 17:
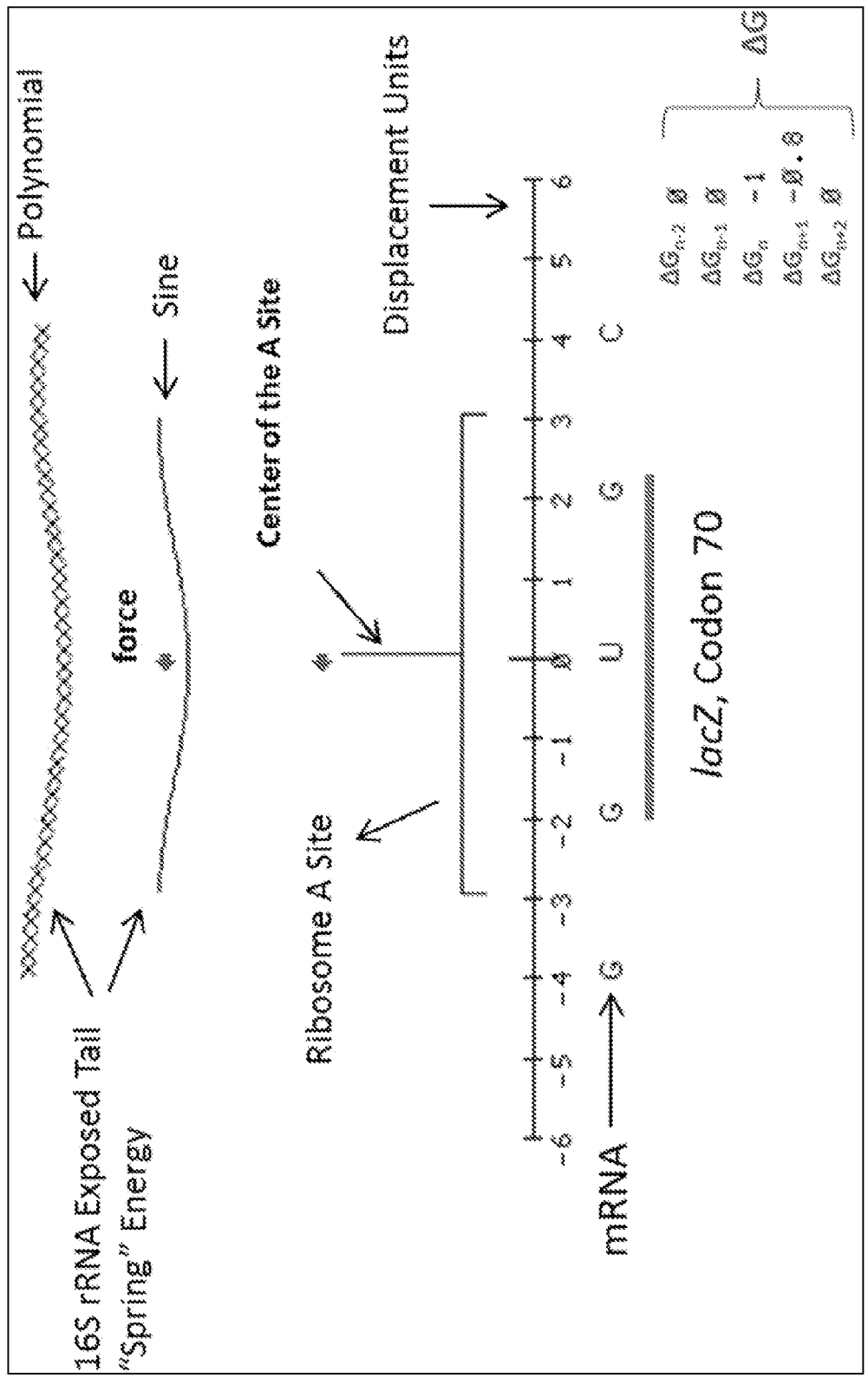

FIG. 17. Simulation of ribosome of translating lacZ at codon 70. At codon 70, the aSD binds to the mRNA 8 nucleotides from the P-site (FIG. 5), resulting in a "relaxed spring". This is modeled by minimal energy located close to the center of the A-site. Therefore the magnitude of the force is small and results in little to no ribosome displacement. The free energies $\Delta G_{n-2}$, $\Delta G_{n-1}$, $\Delta G_n$, $\Delta G_{n+1}$, and $\Delta G_{n+2}$ used to calculate the continuous energy function are displayed on the bottom right.

Figure 18:
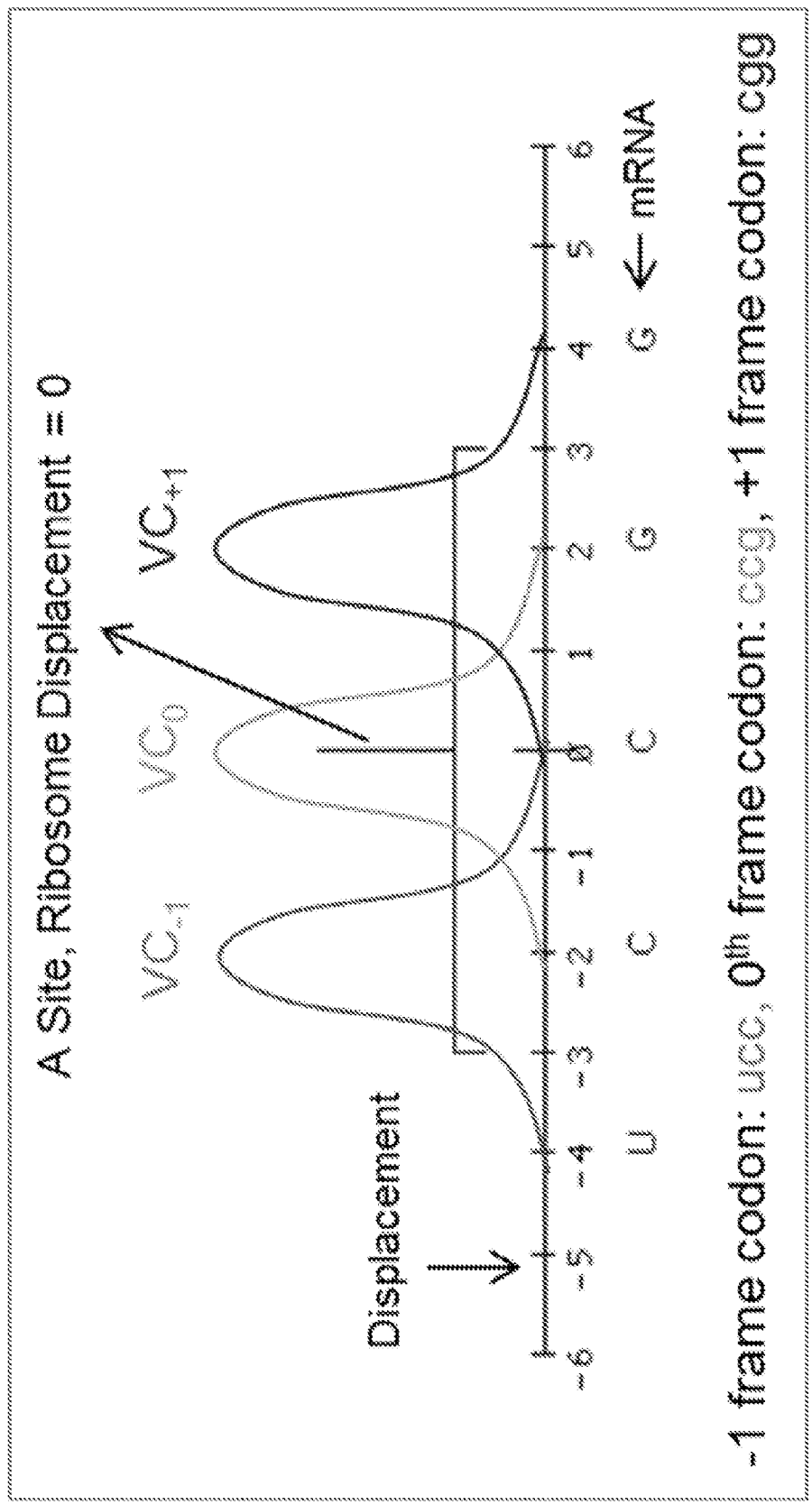

FIG. 18. A-site when ribosome displacement is 0. The A-site is in perfect alignment with the codon in the 0 reading frame. Therefore, the A-site "sees" all of codon ccg and none of the codons in the +1 or −1 reading frame. This is modeled by the view curve VC, being at its peak and $VC_{-1}$ and $VC_{+1}$ being at zero.

Figure 19:
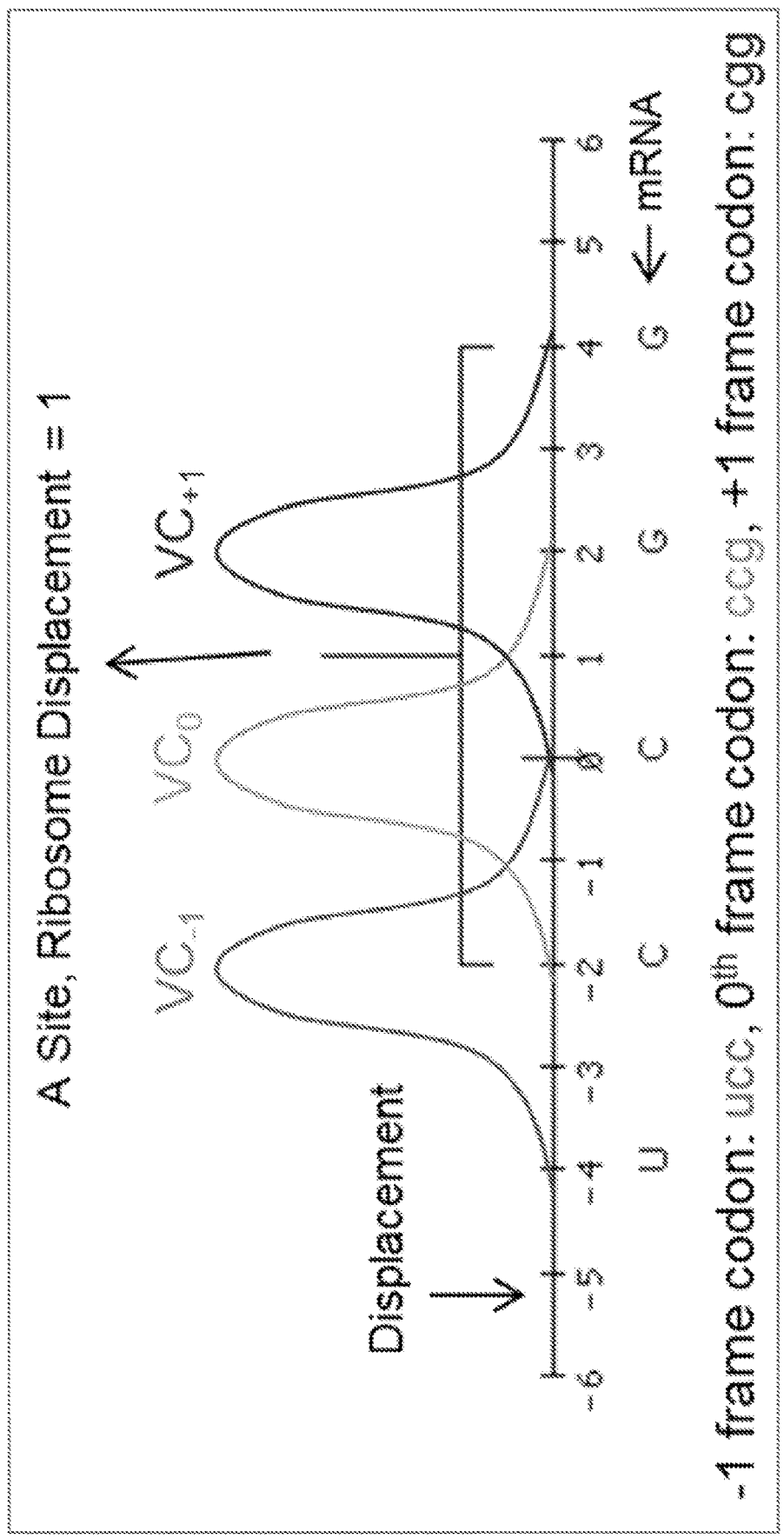

FIG. 19. A-site when ribosome displacement is 1 (equivalent to ½ nucleotides). The A-site is misaligned with the 0 reading frame by ½ nucleotides and therefore "sees" half of codon ccg and half of codons egg in the +1 reading frame. This is modeled by view curve $VC_0$ being equal to $VC_{+1}$.

Figure 20:
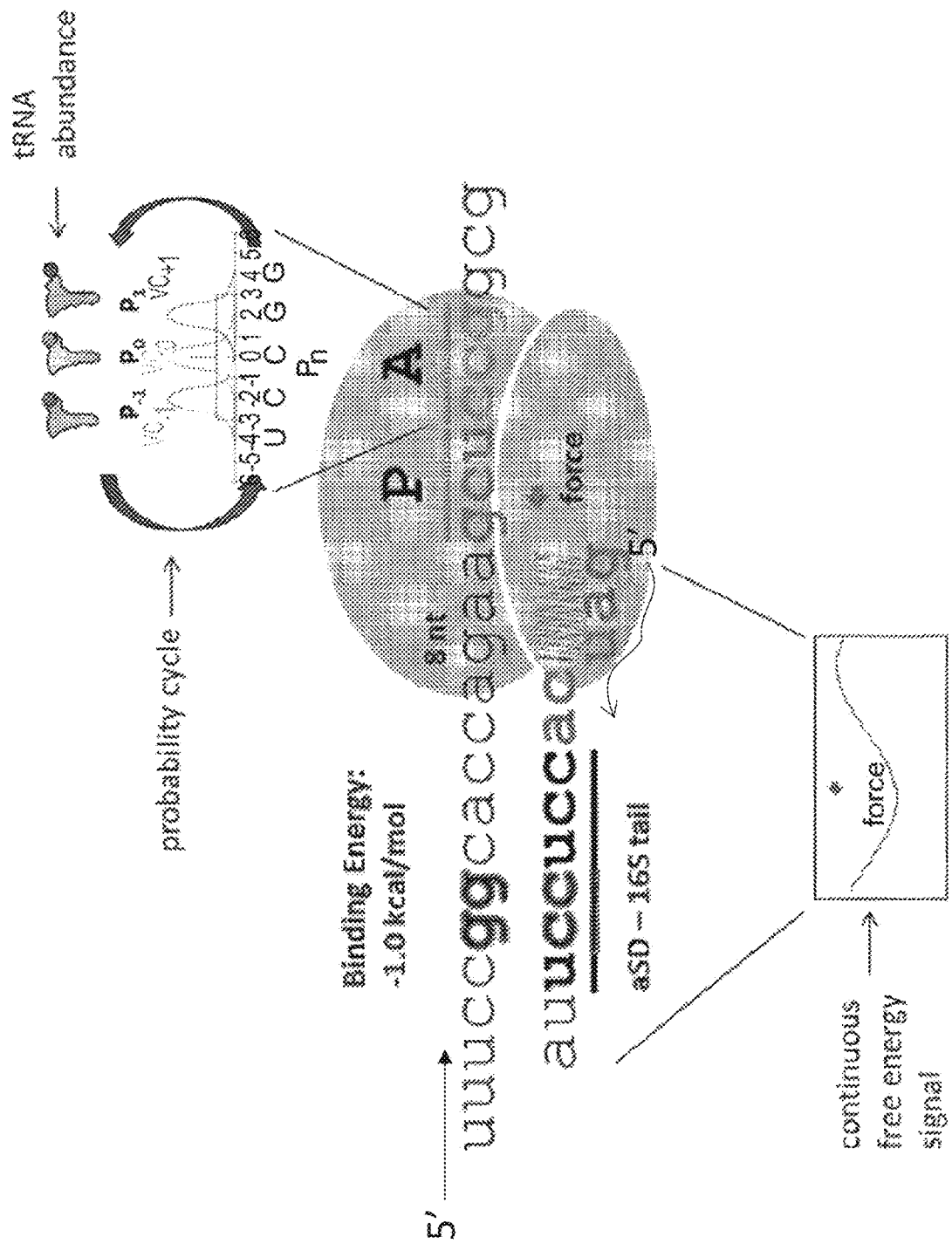

FIG. 20. Graphical illustration of the algorithms. The binding between the mRNA and 16S rRNA "exposed tail" is modeled using a continuous free energy signal from which the force can be calculated. The probability cycle uses probabilities $P_{-1}$ $P_0$, $P_{-1}$, $P_n$, the view curve, aa-tRNA abundance, and the force to displace the ribosome while it waits for the delivery of the next aa-tRNA. After the aa-tRNA has been delivered, the main algorithm moves the ribosome three bases downstream, and the probability cycle begins again. FIG. 20 discloses SEQ ID NOS. 10 and 16, respectively, in order of appearance.

Figure 21:
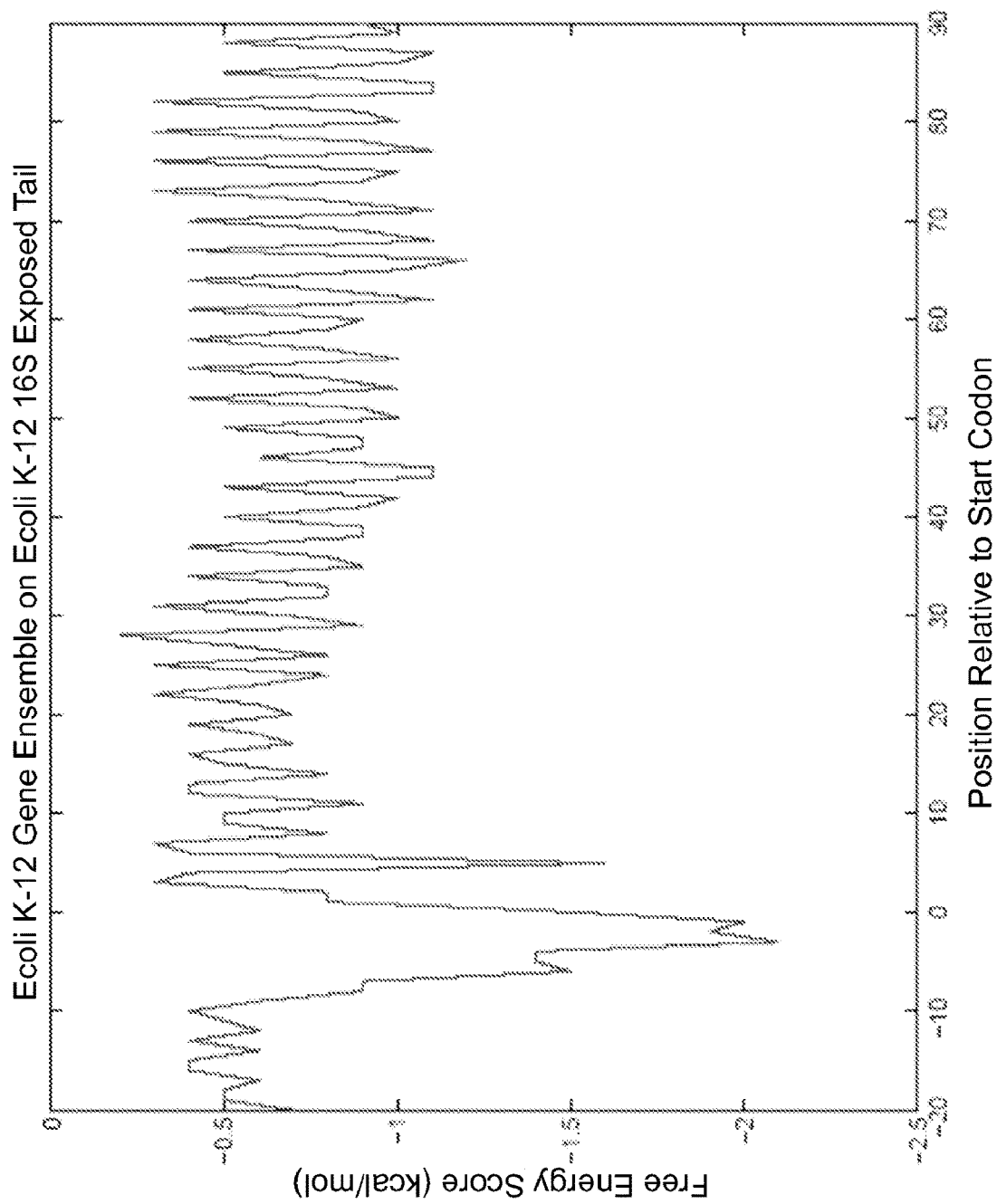

FIG. 21. Periodic signal observed from average free energy of 200 E. coli genes [9].

Figure 22:
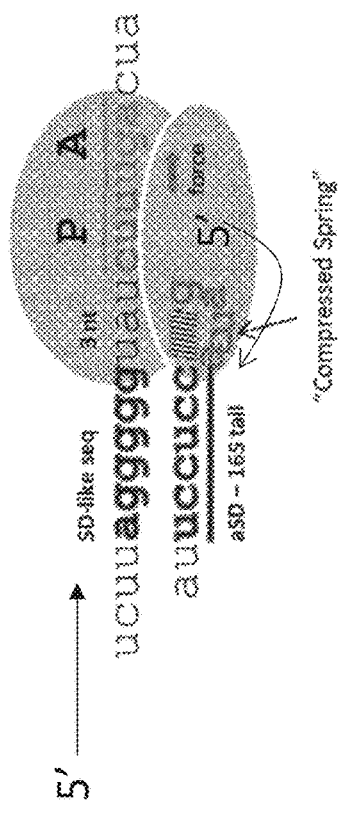
Figure 22:
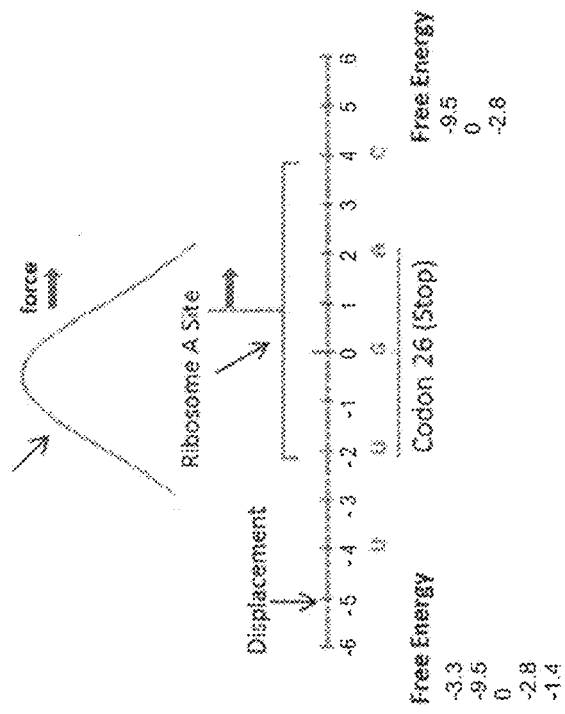

FIG. 22. Translation simulation of prfB. The aSD of 16S "exposed tail" binds too close, 3 nucleotides, to the P site at codon 26 (stop) and compresses the "spring" that displaces ribosome towards minimal energy. FIG. 22 discloses SEQ ID NOS 5 and 16, respectfully, in order of apperance.

Figure 23:
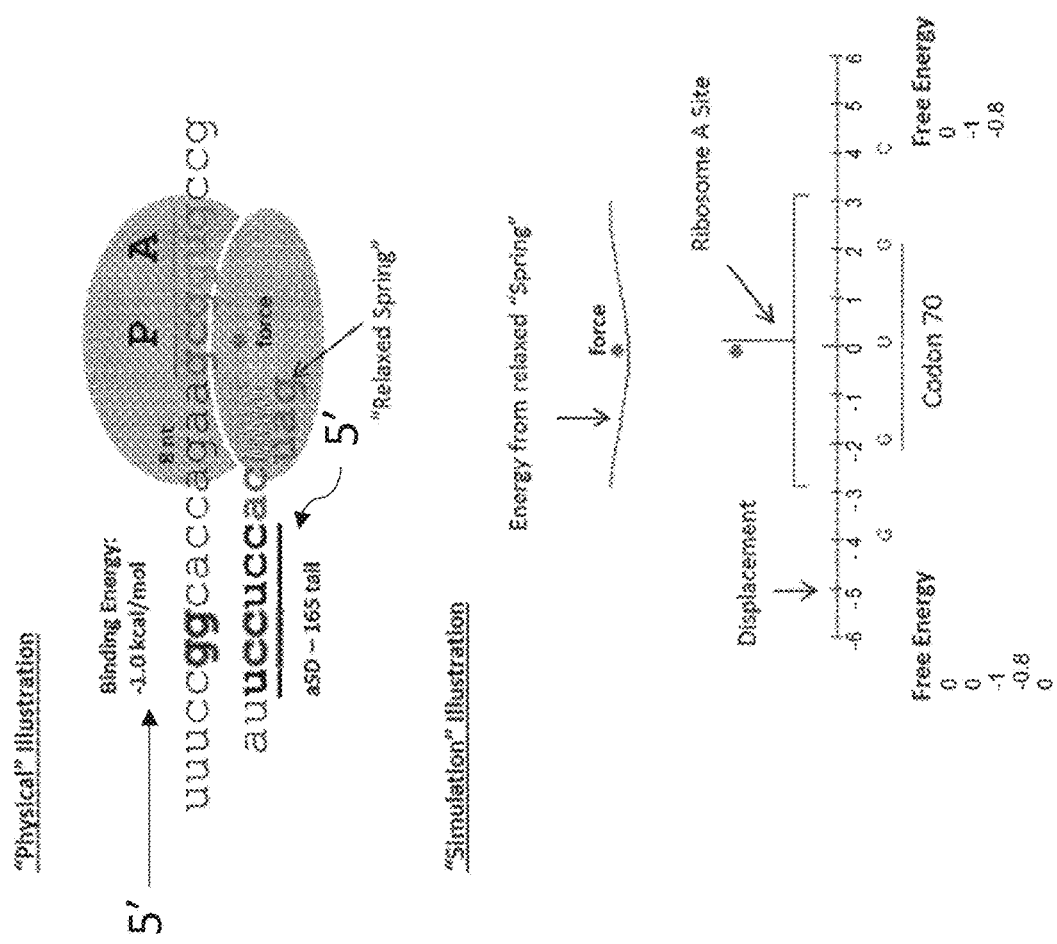

FIG. 23. Translation simulation of lacZ at codon 70. FIG. 23 discloses SEQ ID NOS 6 and 16, respectively, in order of appearance. The aSD binds 8 nucleotides from the P site resulting in a "relaxed spring" close to minimal energy with little to no ribosome displacement.

Figure 24:
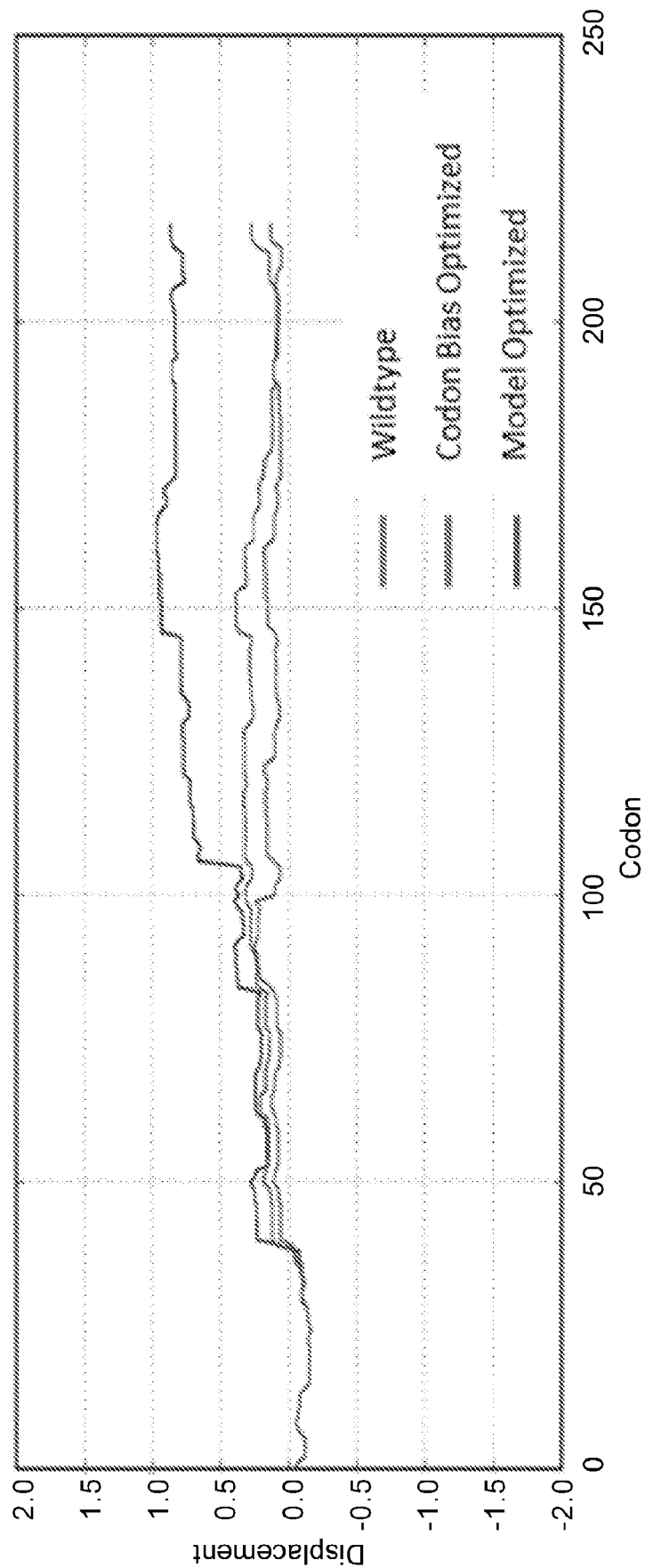

FIG. 24. Ribosome displacement plots of wildtype (top curve), codon bias optimized (middle curve), and model-optimized (bottom curve). Both optimizations reduce displacement.

Figure 25:
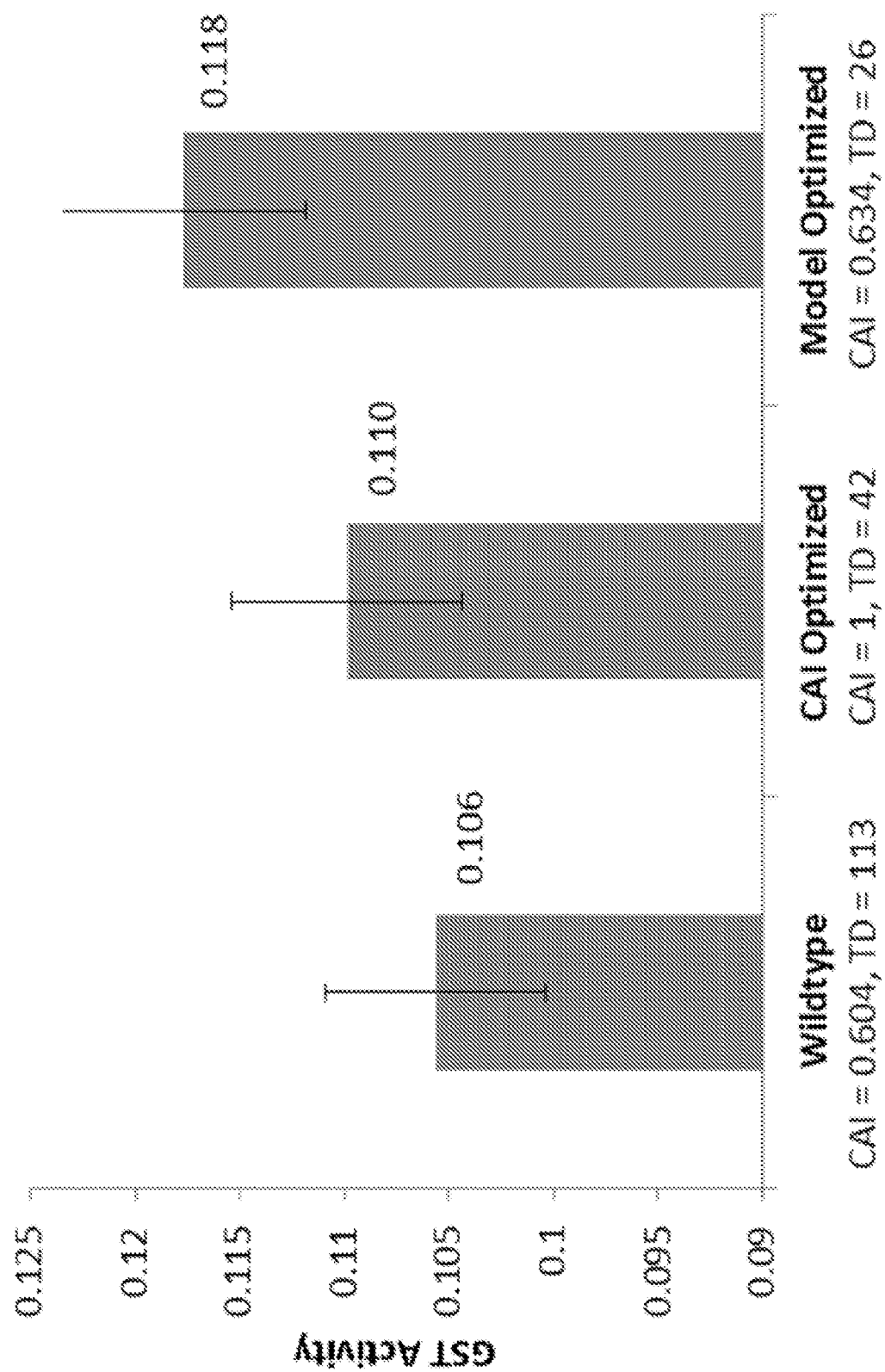

FIG. 25. GST activity of wildtype and optimized genes. The model-optimized variant yields about 11.6% more GST activity than wild type. CAI-optimized yielded 4% more than wildtype. GST activity units are ($\Delta ABS_{340nm}$/min)/$ABS_{562nm}$. Error bar indicates one standard deviation. CAI is codon adaptation index. TD is total displacement.

Figure 26:
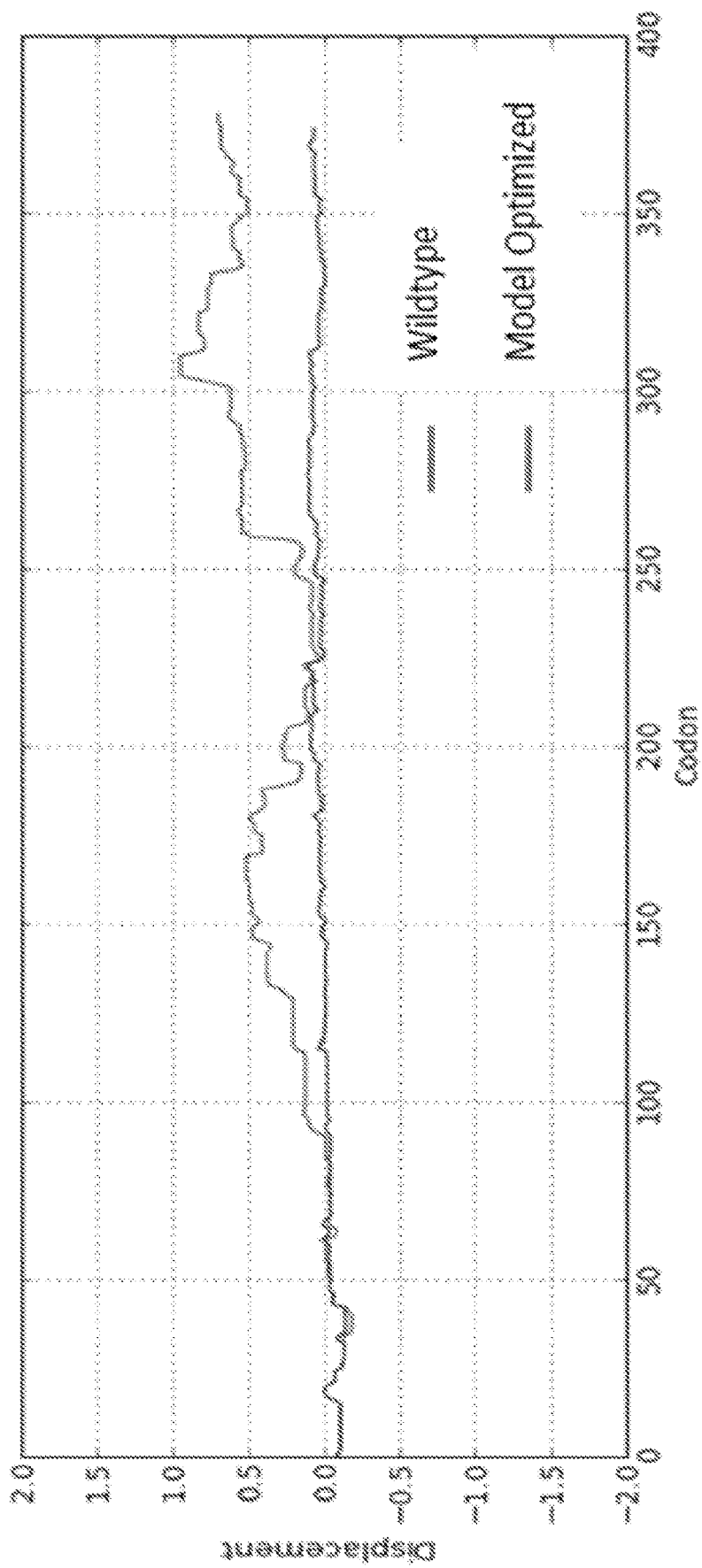

FIG. 26. Ribosome displacement plots of wildtype (top curve) and model-optimized (bottom curve) of adh (alcohol dehydrogenase, CLJU_C11880, from Clostridium ljungdahlii DSM 13528).

Figure 27:
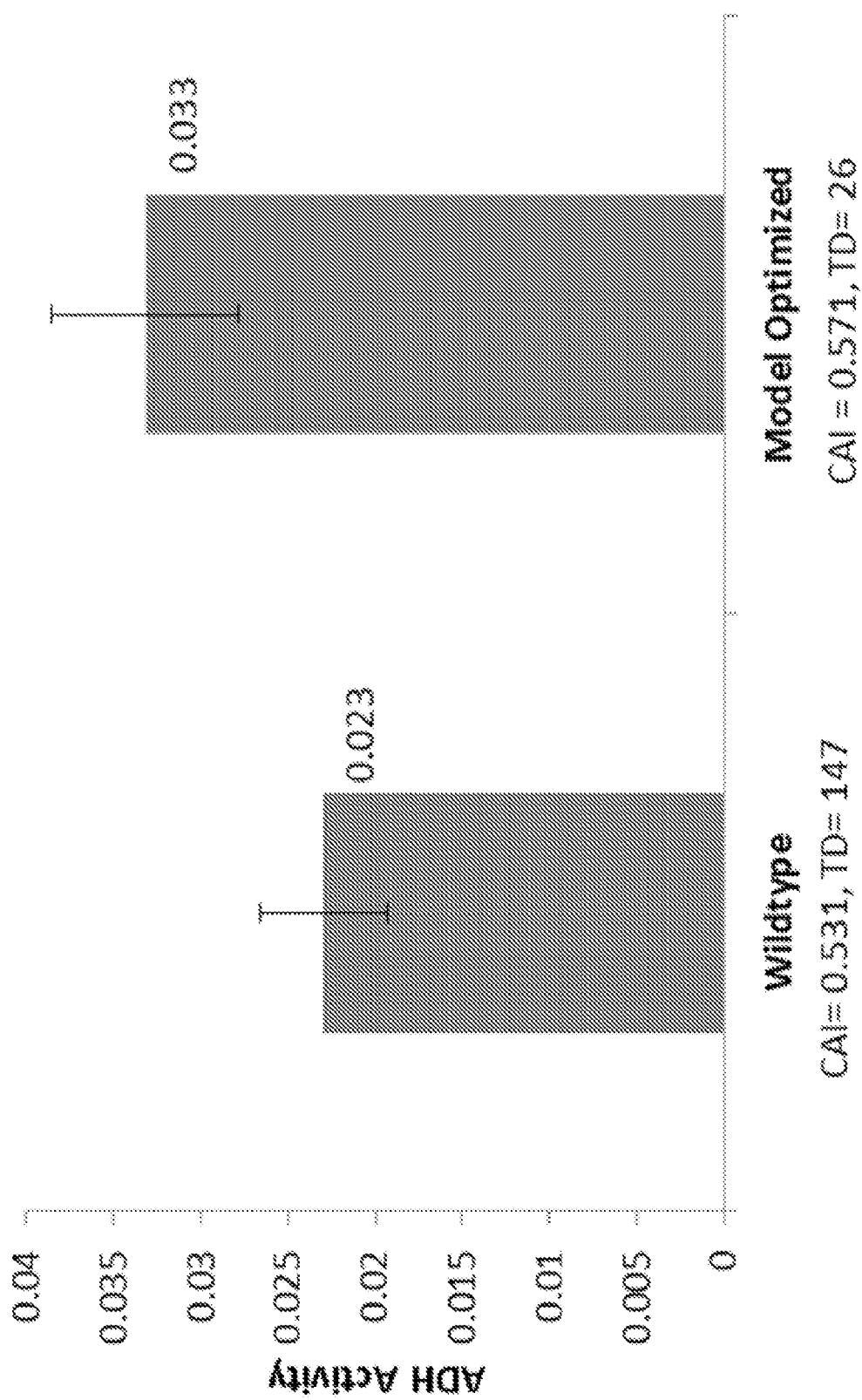

FIG. 27. ADH activity of wildtype and model-optimized genes Optimized variant yields 45% more activity than wildtype. ADH activity units are ($\Delta ABS_{340nm}$/min)/$ABS_{562nm}$. Error bar indicates one standard deviation. CAI is codon adaptation index. TD is total displacement.

Figure 28:
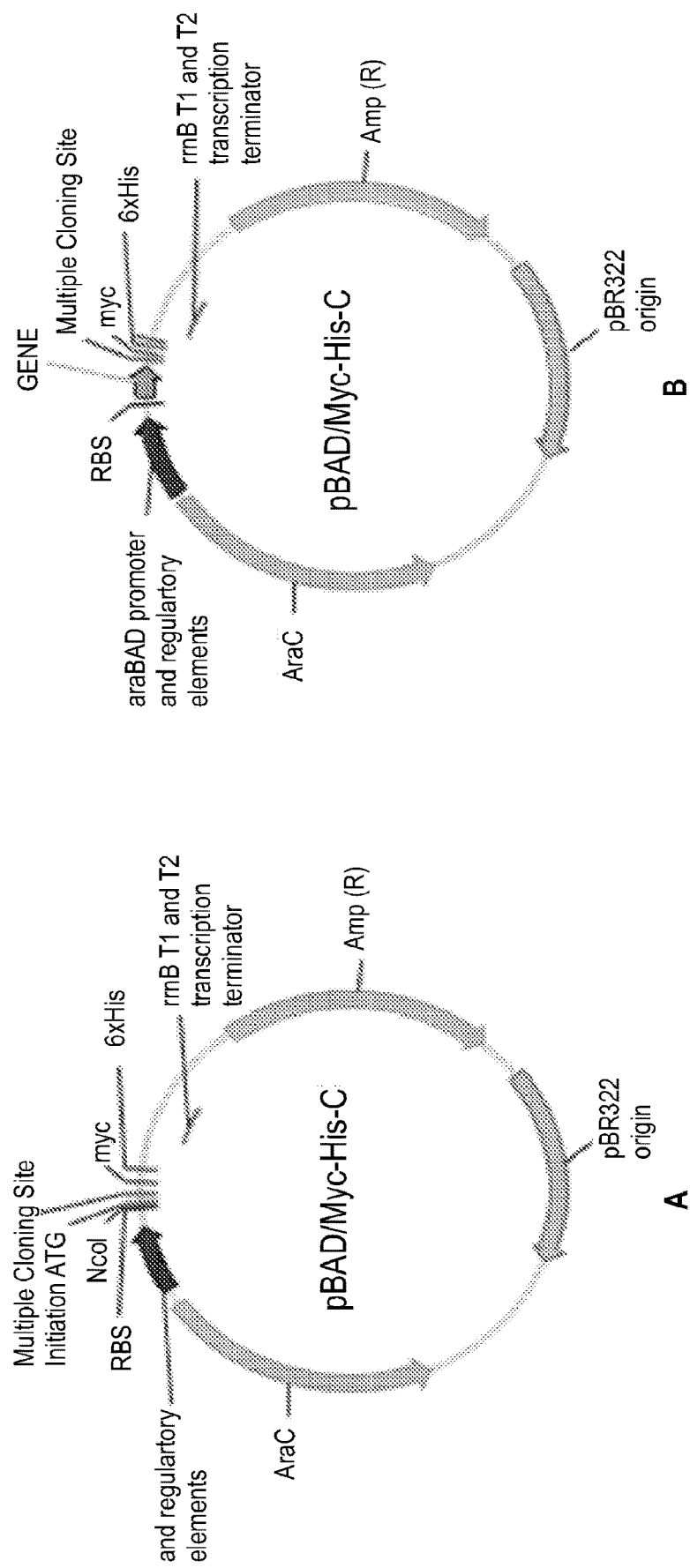

FIG. 28. Insertion of gene into pBAD/Myc-His C plasmid. A) Original pBAD/Myc-His C plasmid available from Thermo Fisher Scientific, Inc. B) Gene cloned into pBAD/Myc-His C plasmid. FIG. 28 discloses "6xHis" as SEQ ID NO: 17.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Fundamentals of Protein Synthesis

Translation is the process in which functional proteins are synthesized from amino acids using mRNA as the coding sequence. The fundamental components of translation are ribosomes, mRNAs, tRNAs, and amino acids. The ribosome decodes the mRNA to assemble the amino acids into a polypeptide chain, which then folds into a functional protein. tRNAs are used to deliver the next amino acid to the ribosome where the amino acid is attached to the polypeptide chain. Translation is split into three stages: initiation, elongation, and termination. During initiation, the ribosome subunit forms a complex to begin elongation. During elongation, the ribosome translocates the mRNA in the 5' to 3' direction; at this stage, the ribosome synthesizes a growing polypeptide chain using aminoacyl-tRNAs (aa-tRNA). Termination is when the ribosome recognizes a release factor at the stop codon and dissociates.

Prior to initiation, the ribosome has dissociated into its 30S and 50S subunits. During initiation, the 30S subunit of the ribosome attaches to the mRNA at the Shine-Dalgarno sequence upstream from the start codon [23]. The Shine-Dalgarno (SD) sequence is a Watson-Crick complement to the 3' end anti-Shine-Dalgarno (aSD) of the 16S rRNA [23]. Once bound, the 30S subunit-mRNA complex is further stabilized by initiation factor 1 (IF1), initiation factor 3 (IF3), and initiator tRNA (fMet-tRNA). IF1 and IF3 guide the 30S assembly by placing the mRNA and initiator tRNA (fMet-tRNA) into the P-site of the 30S and also prevent premature association of the 50S and aa-tRNA. fMet-tRNA is an initiator tRNA that is uniquely charged with N-formyl-methionine, which prevents it from binding with the C-terminus of the previously translated polypeptide. This ensures that N-formyl-methionine is always at the beginning of a polypeptide. Initiation factor 2 (IF2) binds to 30S preinitiation complex and recognizes the formyl group on the initiator tRNA; this further stabilizes the 30S:initiator tRNA interaction. Marshall et al. showed that binding of IF2 to the 30S initiation complex accelerated the joining of the 50S subunit to the 30S subunit to form the 70S initiation complex under the rotated configuration. Their experiments also showed that GTP hydrolysis by IF2 brings the 70S ribosome back into the classic (non-rotated) configuration; in the absence of IF2 and GTP hydrolysis, the ribosome does not enter the elongation phase [24]. The initiation factors and GDP then disassociate from the ribosome:mRNA:initiation-tRNA complex, and translation enters into the elongation phase ready to accept the first aminoacyl-tRNA (aa-tRNA).

Elongation is the step after initiation in which the ribosome reads each individual codon on the mRNA. These codons specify the different amino acids that form the polypeptide chain. The ribosome contains three sites. E, P, and A. The E-site is where uncharged-tRNAs exit the ribosome Next to the E-site is the P-site, where the amino acid attached to the aa-tRNA is added to the polypeptide chain. The codon in the A-site determines the next aa-tRNA to be recruited to the translation complex. In total, elongation consists of three major steps: aa-tRNA binding, transpeptidation, and translocation.

The first step, aa-tRNA binding, is driven by the codon-anticodon interaction between the aa-tRNA and the codon located at the A-site. For this to occur, the ribosome pauses until an aa-tRNA containing the correct cognate nucleotide triplet, dubbed the anticodon, enters the A-site. However, this interaction only loosely follows the canonical Watson-Crick base-pairing, meaning that a single aa-tRNA can recognize more than one codon. This interaction is also aided by elongation factor Tu (EF-Tu), which binds to the aa-tRNA and GTP to form a ternary complex. When this complex interacts with the ribosome, GTP is hydrolyzed to GDP. This lowers the affinity between EF-Tu and the ribosome, which releases EF-Tu and leaves the aa-tRNA at the A-site. The EF-Tu/GTP complex with aa-tRNA also serves in proofreading that the correct amino acid is being added.

The second major step of elongation is transpeptidation, or the formation of the peptide bond. During this step, the aa-tRNA at the A-site interacts with the peptidyl-tRNA located at the P-site. The amino group on the aa-tRNA acts as a nucleophile and "attacks" the carbonyl group in the ester bond between the peptide residue and tRNA moiety at the P-site. This results in the transfer of the peptide bond from the peptidyl-tRNA to the aa-tRNA. The free energy gained from transpeptidation helps drive translocation, the next step of elongation.

The third and final step of elongation is translocation. Here, the deacylated-RNA in the P-site is released through the E-site, and the newly formed peptidyl-tRNA in the A-site shifts to the P-site. This leaves the A-site vacant and ready for the next aa-tRNA to bind. This translocation process is catalyzed by elongation factor G (EF-G). Similar to EF-Tu, EF-G forms a complex with GTP and binds to the ribosome. Upon translocation, GTP is hydrolyzed to GDP, and the affinity between EF-G and the ribosome is decreased, thereby releasing EF-G from the ribosome. In short, translocation consists of the ribosome moving in frame downstream from the initiation codon in controlled movements that are a distance of three bases (one codon) long.

Termination of translation involves the recognition of one of three termination codons: UAA, UAG, or UGA [25,26,27,9,17,36]. It is important to note that termination codons are often found in the other reading frames, meaning that accidental frameshifting during translocation will often result in termination of the faulty protein. Termination codons do not code for any amino acid but instead induce the binding of release factors (RF1, RF2, RF3). RF1 is specific to termination codons UAA and UAG; whereas, RF2 is specific to UAA and UGA. RF3 acts in a GTP-dependent fashion similar to EF-Tu and EF-G. These release factors simulate the aa-tRNA interaction at the A-site and break the peptidyl-tRNA ester bond rather than the usual transpeptidation, detaching the polypeptide chain from the P-site [26,27]. GTP is then hydrolyzed to GDP, and the release factors are released from the ribosome. The deacylated-tRNA is then released, and the ribosome separates into the 50S and 30S subunits, terminating the process of translation.

Reading frames are a perspective for analyzing a nucleotide sequence based on the three base compositions of codons in protein coding regions of mRNA. The addition or elimination of a single nucleotide to a coding sequence would shift the reading frame. A change in reading frame can drastically alter the primary sequence of a polypeptide and cause early termination. Since the genetic code calls for translation of three nucleotides to one amino acid, from a fixed starting position (as set by the initiation codon), there exist three reading frames from which the codons can be read. The reading frame defined by the start codon is called the 0 reading frame. The frame that would be one base downstream from the 0 frame is called the +1 reading frame, and the frame with a one base shift upstream is called the −1 reading frame. Most coding regions in genomes code for one protein in one reading frame, but exceptions such as overlapping (internal) genes [28,29,30] and programmed frameshifts have been observed [31,32,33,34].

Frameshifting is a mechanism in which the ribosome shifts out of the 0 frame and into one of the two other frames relative to the start codon. This produces a different amino acid sequence compared to the original reading frame. There are two common types of frameshifts: +1 and −1 frameshifts. These events rarely occur in nature; however, some genes have evolved to contain embedded frameshifts. These are called "programmed" frameshifts. An example of a +1 programmed frameshift is prfB in *E. coli* [31,33]. The phenomenon of programmed frameshifting has been studied intensively because of its potential to reveal the mechanisms that maintain the appropriate reading frame of the ribosome during translation. The model gene prfB in *E. coli* has been studied in detail to determine the sequence features that are associated with a specific shift in reading frame.

Determinants of Protein Yield During Initiation and Elongation

Salis et al. [35] provide an extensive analysis of translation initiation in their 2009 publication. They contend that the four molecular interactions that determine initiation rates are (1) 16S rRNA to ribosome binding site (RBS) hybridization, (2) 16S rRNA binding site to start codon spacing, (3) RNA secondary structures that occlude either the 16S rRNA binding site or the standby site, and (4) the binding of fMet-tRNA to the start codon. These first three determinants are integral to modeling translation initiation and are discussed here. The fourth determinant, involving binding of the first tRNA to the start codon, stabilizes the initiation complex and aids in the transition to elongation.

The development of a model for translation elongation dates back several decades. More recently, various predictive indices and optimization methods for translation have emerged [36,37,38,39,40,41]. Predictive indices and optimization methods have largely focused on the elongation step, during which the ribosome translocates down the mRNA while tRNAs transfer amino acids to the growing polypeptide chain.

In 2014. Vu et al. [42] revealed yet another determinant of protein yield based on second order free energy effects from the binding between the anti-Shine-Dalgarno sequence of the 3' terminal rRNA tail and the mRNA transcript. Vu et al. [42] described a new factor dubbed ribosome displacement that arises from these second-order free energy effects. Ribosome displacement is the misalignment between the A-site and normal "zero" reading frame and is proposed to be "cumulative" during elongation; i.e., misalignments are not reset after translocation. This paradigm suggests that ribosome has "memory" during elongation.

Vu et al. [42] used the well-established programmed frameshifting genes prfB and dnaX as the basis to establish their model. They computed a "spring-like" reaction force that displaces the ribosome relative to the mRNA after translocation. They refer to this displacement as the secondary ribosome movement; translocation is the primary movement. The spring-like reaction force is modeled by calculating the change in energetic interactions between the 16S rRNA exposed tail and mRNA using the fundamental law of physics (Δenergy=−force·Δdistance). Vu et al. [42] call this ribosome spring-like reaction the ribosome spring model. The ribosome spring model convolves tRNA abundance, ribosome displacement, and spring-like reaction force to simulate the secondary ribosome movements during elongation. Shultzaberger et al. [43] and Salis et al. [35] also referred to the ribosome acting like a "rigid spring" when investigating optimal SD to start codon spacing at initiation. Tinoco et al. [44] also proposed that a "springy" 16S rRNA aSD: SD helix produced a −1 frameshift. Vu et al. [42] then used the ribosome spring model to optimize heterologous protein production. The spring-like force can be realized as a change in the "phase" of the free energy sinusoidal signal. By changing codons of a gene using synonymous codons, this force can be minimized to reduce ribosome displacement and improve protein yield. Vu et al. [42] described the "phase" of the free energy sinusoidal signal that minimizes the spring-like force and ribosome displacement. That phase is termed the "species angle," which is, as the name implies, unique to each organism. By minimizing displacement, Vu et al. [42] optimized protein production for two genes: Glutathione S-Transferase (GST) from *Schistosoma japonicum* and alcohol dehydrogenase (ADH) from *Clostridium ljungdahlii*. GST optimized with their model showed an 11.6% increase over the wildtype, compared to a 4% increase over wildtype for CAI-optimized GST. ADH activity was 45% higher from the optimized gene compared to wildtype. The ribosome spring model takes into account ribosome displacement, tRNA abundance, and spring-like reaction force to produce a "wait-time" parameter at each codon. Minimizing these wait-time parameters is crucial to producing proteins efficiently [42].

Methods of Predicting and Optimizing Protein Yield and Aggregation

Ineffective heterologous protein synthesis has often been ascribed to codon bias and rare codons. New experimental evidence suggests that codon bias alone may not be the sole cause of poor translation. The presently disclosed subject matter provides a free-energy based model of translation elongation to predict and optimize protein yield and aggregation. The model takes into account second order free energy effects from the binding between the anti-Shine-Dalgarno sequence of the 3' terminal rRNA tail and the mRNA, tRNA abundance, and ribosome displacement. The model and software allow optimization of genes for increased or decreased protein yield as well as increased or decreased protein aggregation. As described in the Examples below, the model's predictive and optimization accuracy was assessed by optimizing and expressing three model genes and multiple mRNA variants coding for GST (26 kDa Glutathion S-Transferase from *Schistosoma japonicum*). Protein yield of optimized genes showed increase from their wildtype levels. Optimization of Glutathion S-Transferase from *Schistosoma japonicum* and Alcohol Dehydrogenase from *Clostridium ljungdahlii* DSM 13528 are discussed in the Examples below.

Accordingly, in one aspect, a method for predicting protein yield for translation of a gene is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) determining a total cycle count across codons throughout the coding region; wherein the total cycle count across codons throughout the coding region is correlated with protein yield.

In another aspect, a method for predicting protein yield for translation of a gene is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; (b) plotting a translation bottleneck plot, wherein the plot comprises values comprising a sum of cycles within a sliding window of size N codons; and (c) determining a maximum sum in the translation bottleneck plot; wherein the maximum sum in the translation bottleneck plot is correlated with protein yield.

In another aspect, a method for predicting protein yield for translation of a gene is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) performing a protein translation simulation to determine an amount of ribosomes that finish translation within a number of cycles; wherein the amount of ribosomes that finish translation within a number of cycles is correlated with protein yield.

In another aspect, a method for increasing protein yield for translation of a gene is provided, the method comprising: (a) performing any one of the methods for predicting protein yield for translation of a gene as described above; and (b) modifying codons using synonymous codons that conserve the protein amino acid sequence while changing the force and/or the wait time; wherein the protein yield for translation of the gene is increased. In further aspects, step (b) comprises modifying codons such that ribosome wait time is decreased. In further aspects, the ribosome displacement magnitude is minimized by selecting for a phase angle of the gene that is substantially equal to a species angle of the gene.

In another aspect, a method for decreasing protein yield for translation of a gene is provided, the method comprising: (a) performing any one of the methods for predicting protein yield for translation of a gene as described above; and (b) modifying codons using synonymous codons that conserve the protein amino acid sequence while changing the force and/or the wait time; wherein the protein yield for translation of the gene is decreased. In further aspects, step (b) comprises modifying codons such that ribosome wait time is decreased.

It is known that protein aggregation is caused by misfolding [117,119, 120] resulting from non-optimal ribosome translational speed [117]. It also known that certain protein coding region requires different timing to fold properly [118]. Therefore, one can deduce that slowing translation speed at key coding regions will reduce protein aggregation. Accordingly, in another aspect, a method for predicting protein aggregation is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal RNA tail of the ribosome; and (b) determining a total cycle count across codons throughout the coding region; wherein the total cycle count across codons throughout the coding region is correlated with protein aggregation.

In another aspect, a method for predicting protein aggregation is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome: (b) plotting a translation bottleneck plot, wherein the plot comprises values comprising a sum of cycles within a sliding window of size N codons; and (c) determining a maximum sum in the translation bottleneck plot; wherein the maximum sum in the translation bottleneck plot is correlated with protein aggregation.

In another aspect, a method for predicting protein aggregation is provided, the method comprising: (a) determining ribosome wait time at each codon in a coding region of an mRNA encoding the protein, comprising determining a number of cycles at each codon, wherein the number of cycles is a function of tRNA abundance, ribosome displacement magnitude, and force from binding between the mRNA and a 3' terminal rRNA tail of the ribosome; and (b) performing a protein translation simulation to determine an amount of ribosomes that finish translation within a number of cycles; wherein the amount of ribosomes that finish translation within a number of cycles is correlated with protein aggregation.

In another aspect, a method for increasing protein aggregation is provided, the method comprising: (a) performing any one of the methods for predicting protein aggregation as described above; and (b) modifying codons using synonymous codons that conserve the protein amino acid sequence while changing the force and/or the wait time; wherein protein aggregation is increased. In further aspects, step (b) comprises modifying codons such that ribosome wait time is decreased.

In another aspect, a method for decreasing protein aggregation, the method comprising: (a) performing any one of the methods for predicting protein aggregation as described above; and (b) modifying codons using synonymous codons that conserve the protein amino acid sequence while changing the force and/or the wait time; wherein protein aggregation is decreased. In further aspects, step (b) comprises modifying codons such that ribosome wait time is decreased.

In another aspect, any of the methods disclosed herein are provided, wherein the gene is from a prokaryotic organism and the 3' terminal rRNA tail of the ribosome is a 16S rRNA tail. In another aspect, any of the methods disclosed herein are provided, wherein the gene is from a prokaryotic organism. Without limiting the scope of the presently disclosed subject matter, any of the methods disclosed herein may be applicable to genes from prokaryotic organisms including, but not limited to, *Acinetobacter, Actinobacillus, Actinomyces pyogenes, Actinomyces pyogenes. Aeromonas hydrophilia, Alcaligenes* fecalis, Aligella *urethralis, Alteromonas* putriaciens, *Alteromonas* putrifuciens, *Bacteroides distasonis, Bacteroides fragila, Bacteroides melaminogenicus, Bacteroides ovatus, Bacteroides* thetaiomicion. *Bacteroides uniformis, Campylobacter, Candida albicans, Capnocytophaga*, CDC group Ivc, *Chlamydia trachomatis, Citrobacter fruendii, Clostridium* difficle, *Clostridium histolyticum, Clostridium ljungdahlii, Clostridium perfingens, Clostridium septicum, Clostridium sordelli, Clostridium sporogenes, Corynebacterium diptheria, Corynebacterium* pseudodoi., *E. coli, E. coli* 0157-H7, *E. coli*-βlactamase positive, *Enterobacter aerogenes, Enterobacter* cloecae, *Enterobacter* fecalis, *Eubacterium* lentum, *Flavobacterium* meningiosepticum. *Fusobacterium, Fusobacterium* miningio, Haemophilia parainfluenza, Haemophilis influenza, *Haemophilus aphrophilus, Klebsiella oxytoca, Klebsiella pneumonia, Klebsiella rhinoscleromatis, Legionella micdliea, Legionella pneumophilia, Leuconostoc lactic,*

*Leuconostoc mesanteriodas, Listeria murrayi, Mima. Mycobacterium avium* intracellulari, *Mycobacterium flavescens, Mycobacterium gordoniae, Mycobacterium* terra group, *Mycobacterium* tuberculoses, *Neisseria cinerea, Neisseria gonorrhea, Neisseria* lactamica, *Neisseria meningitidis, Neisseria sicca, Nocardia brasiliensis, Pasteurella multocida, Proteus mirabilis, Proteus vulgaris, Pseudomonas* cepatia (strain I), *Pseudomonas* cepatia (strain II), *Salmonella* cholerasuis, *Salmonella* dublin, *Salmonella* muenchen, *Salmonella* paratyphi, *Salmonella typhimurium, Schistosoma japonicum, Serratia oderifera, Shigella boydii, Shigella dysenteriae, Shigella felxneri, Shigella sonneri, Staphylococcus aureus, Staphylococcus* epi., *Staphylococcus* saphrophy, *Streptococcus* alpha, *Streptococcus* beta (Group C), *Streptococcus* beta (Group F), *Streptococcus bovis, Streptococcus fecalis, Streptococcus* Group B, *Streptococcus mitis, Streptococcus mutans, Streptococcus pneumonia, Torulopsis globrata, Treponema denticola, Treponema pallidum, Treponema pertemie, Treponema phagedenis, Treponema* refrigens, Vibro paruhen, and *Yersinia* enterolitica.

It is known that the 18S tail interacts with the mRNA in eukaryotes during translation intitation [124] and elongation [121, 122, 123]. Therefore, the 18S tail can be used for the eukaryote model. Accordingly, in another aspect, any of the methods disclosed herein are provided, wherein the gene is from a eukaryotic organism and the 3' terminal rRNA tail of the ribosome is an 18S rRNA tail. The term "eukaryotic" refers to a nucleated cell or organism. Without limiting the scope of the presently disclosed subject matter, any of the methods disclosed herein may be applicable to genes from eukaryotic organisms including, but not limited to, insect cells, plant cells, mammalian cells, animal cells, and lower eukaryotic cells. The term "lower eukaryotic cells" includes yeast and filamentous fungi. Yeast and filamentous fungi include, but are not limited to, *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula* polymorphs, *Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp, *Hansenula polymorpha*, any *Kluyveromyces* sp, *Candida albicans*, any *Aspergillus* sp., *Trichoderma reesei, Chrysosporium lucknowense*, any *Fusarium* sp. And *Neurospora crassa.*

In a further aspect, a computer readable medium is provided, programmed to perform one or more of any of the method steps disclosed herein. Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise." "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to practice the methods of the present invention.

Example 1

A New Biophysical Model for Translation Elongation

Discovery of the Periodic Free Energy Signal

A periodic free energy signal was observed from the average Watson-Crick binding between the 16S rRNA 3' terminal end "exposed tail" (3'-AUUACCUCCACUAG-5') (SEQ ID NO: 12) and the mRNA during translation, as shown in FIG. 1 [45,46]. The most prominent binding energy is at initiation which corresponds to the anti-Shine-Dalgarno (aSD) of the "exposed tail" binding to the Shine-Dalgarno (SD) sequence. After that, there is a periodic (sinusoidal-like) binding signal (in which negative free energy indicates binding) that corresponds to "in-frame" ribosome translocation during elongation [45,46,47]. Fourier transformation of this periodic signal revealed a prominent peak at a frequency of ⅓ cycles per nucleotide [46,48]. This illustrates that the exposed tail binds to the mRNA at every codon during elongation. However, after the stop codon is reached, the signal quickly attenuates, which indicates that the ribosome has stopped translating, as shown in FIG. 2. Ribosome profiling experiments of Li et al. [49] provide physical evidence of the continuous interaction between the 16S rRNA "exposed tail" and the mRNA during elongation. Weiss et al. [50] and Larsen et al. [3]] ERN Alfoxxposhdttahl' affloftite the mRNA to produce a programmed translational frameshift; their observations implied that the exposed tail interacts with the mRNA during elongation. Li et al. [49], Weiss et al. [50], and Larsen et al. [51] provide corroborating physical evidence for the periodic free energy signal which suggested that the 16S rRNA "exposed tail" interacts with mRNA during elongation Without being bound by theory, it is proposed that the functional purpose of the 16S rRNA tail:mRNA binding is to keep the ribosome in the proper reading frame, or in other words, the binding serves as reading frame maintenance. Heterologous protein translation disrupts this binding and therefore "displaces" the ribosome. This periodic free energy signal inspired a new mechanistic "spring" model for translation elongation as described further below Ribosome Spring Model Analysis of the free energy signal for the *E. coli* gene prfB using the cumulative magnitude and phase method showed a change in free energy for both the magnitude and phase at the frameshift site [45,52]. Using a fundamental law of physics, the force exerted on the ribosome at the frameshift site can be calculated:

$$\Delta\text{energy} = -\text{force} \cdot \Delta\text{distance}$$

This inspired the development of the ribosome "spring" model for translation elongation using second-order free energy effects from the 16S rRNA 3' terminal end:mRNA bindings that elucidate frameshifts and illustrate a key concept: ribosome displacement. The ribosome spring model was also developed to predict and optimize protein yield in heterologous protein production applications [53].

As the ribosome translocates along the mRNA, the 16S rRNA 3' terminal end interacts with bases upstream of the ribosome [49,50,51], as shown in FIG. 3. If that binding energy is sufficiently large and is on the "wrong" side of favoring normal in-frame binding, the binding between the 16S rRNA:mRNA acts like a spring and may exert extra force on the ribosome and displace it. In the extreme case, a frameshift may occur. The "spring-like" reaction force is modeled using a sinusoidal or polynomial curve.

For example, in the +1 programmed frameshifting gene prfB (FIG. 4), the aSD of the 16S exposed tail binds to the SD-like sequence 3 bases (UAU in FIG. 4) upstream from the P-site [50], resulting in-9.5 kcal/mol of binding energy. This binding is too close to the P-site and thus compresses the distance between the tail and the ribosome. It behaves like a compressed spring, which upon relaxation displaces the ribosome three quarters of a base downstream into the +1 reading frame where the spring is at minimal energy. The displaced ribosome then picks up the aminoacyl-tRNA in the +1 frame. This leads to a one-base frameshift after which the new reading frame is maintained [45,47,52].

In contrast, the SD in the −1 frameshifting gene of dnaX is 10 bases away from the P-site [51]. This binding extends the "spring" and displaces the ribosome backwards to produce a "partial" frameshift (on which the ribosome now lies between reading frames; producing both τ and γ subunits) [51]. Recent optical tweezer and structural experiments of Tinoco et al. [54] suggest that the aSD forms a springy helix with the SD-like sequence to produce a −1 programmed frameshift.

FIG. 6 shows the *E. coli* 16S aSD during in-frame translation of lacZ. The binding energies around that site range from 0 to −1 kcal/mol. Because the aSD is bound 8 nucleotides away from the P-site, the "spring" is in its "relaxed" state. While slight misalignments between the zero reading frame and A-site are possible, there is not enough "spring force" to cause a frameshift. Interestingly, the spacing between the aSD and the P-site of 5 nucleotides in the relaxed spring during elongation also corresponds to the optimal SD and start codon spacing at initiation, which was observed by Chen et al. [55]. Without being bound by theory, it is proposed that a "relaxed spring" state also occurs when the "optimal" spacing between the SD and start codon is 5 to 8 bases at the translational initiation site [55,56,57]. This compression or extension of the spring leads to the proposed concept: ribosome displacement.

Ribosome Displacement

Ribosome displacement is the misalignment between the ribosome A-site and the normal 0 reading frame (see FIG. 8) caused by the force from the aforementioned "spring". This misalignment is a distance on the order of fractions of a nucleotide. The degree to which a ribosome is displaced is dependent on the magnitude of the force and the aa-tRNA abundance of the codon in the 0 reading frame. For example, if the force is high and the aa-tRNA abundance for the codon in the 0 reading frame is also high, then displacement will be mitigated. However, if the force is high and the aa-tRNA abundance in the 0 reading frame is low, then the displacement will be amplified. A ribosome that is more displaced will take longer to choose between the two aa-tRNAs of the two available reading frames because tRNA binding is disrupted; this, therefore, increases the ribosome "wait-time". The aa-tRNA abundance of codons in the three reading frames has a major impact on the ribosome wait time; this is modeled by tRNA binding competition as described further below. A displaced ribosome can also pick up the wrong aa-tRNA in either the +1 or −1 reading frame, as shown in FIG. 8.

Ribosome displacement is cumulative and does not reset after translocation. This suggests that the ribosome has "memory" during translation elongation. Because the ribosome has memory, ribosome displacement can be "fixed" anywhere on the mRNA by the use of "slow" codons and favorable force. "Slow" codons are codons that use low abundance aa-tRNA. For example, if the ribosome is displaced towards the +1 reading frame, a force towards the 5' end (modeled as an extended spring) coupled with a slow codon can realign the ribosome.

In the model, one displacement unit corresponds to a misalignment of half a nucleotide. Two displacement units is a misalignment of a full nucleotide or a shift in reading frame. Ribosome displacement is calculated at each codon during translation elongation. FIG. 9 shows the ribosome displacement plot for translation of +1 programmed frameshifting gene prfB.

Translation Elongation Dynamics

After initiation, the ribosome enters into the elongation phase. During elongation, the ribosome awaits the delivery of the next aminoacyl-tRNA (aa-tRNA). After delivery of the aa-tRNA, transpeptidation begins where the polypeptide chain is transferred from the peptidyl-tRNA (p-tRNA) to the aa-tRNA. This triggers the rotation of the ribosome into the hybrid conformation where the acceptor end of the p-tRNA and aa-tRNA fluctuates. Rotation of the 30S head and binding of the EF-Tu: GTP complex stabilizes this fluctuation and "unlocks" the mRNA from the ribosome in preparation for translocation. EF-Tu hydrolysis of GTP translocates the ribosome 3 nucleotides downstream. Without being bound by theory, it is proposed that just after translocation when the mRNA is "unlocked", the 16S rRNA "exposed tail" binds to the mRNA and acts like a spring to displace the ribosome in either the +1 or −1 reading frame while it waits for the delivery of the next aminoacyl-tRNA. At this stage, the ribosome also rotates back into the classic confirmation. The degree to which the ribosome is displaced is a function of the force magnitude and how long the ribosome has to wait for the delivery of the next aminoacyl-tRNA, which is related to aa-tRNA abundance. A ribosome that is more displaced has to wait a longer period before picking up the next aminoacyl-tRNA due to tRNA binding disruption. A displaced ribosome is also more likely to pick up the wrong aminoacyl-tRNA from the +1 or −1 reading frame. After the ribosome has picked up the next aa-tRNA, the ribosome enters transpeptidation, and the cycle repeats.

Without being bound by theory, it is proposed that this spring mechanism acts to keep the ribosome in the appropriate reading frame when translating native genes with the exception of programmed frameshifts. The corollary is that the purpose of this mechanism is to reduce the "noise" produced from translocation; i.e. translocation does not always move the ribosome exactly three nucleotides, but approximately 3 nucleotides plus or minus fractions of a nucleotide. This "noise" is due to the entropy from transducing hydrolysis energy into kinetic energy to translocate the ribosome. Translating heterologous genes disrupts "normally evolved" 16S rRNA tail:mRNA binding, which in turn may lead to a displaced ribosome that increases ribosome wait time, creates bottlenecks, or causes frameshifts. Programmed translational frameshift sites like those found in prfB and dnaX exist [50,51,54,58,59] and their efficiency relies on the aforementioned ribosome interactions. The mechanisms behind programmed translation frameshifts [53,54] support the model and are directly relevant to ribosome dynamics during normal translation elongation.

Ribosome Wait Times

The ribosome "wait time" at each codon is calculated as a function of the force from the spring, ribosome displacement, and tRNA abundance. The model computes the ribosome "wait time" at each codon during translation elongation. The output of the "wait time" is in units of "cycle" as measure of how long it takes the ribosome to load the next aa-tRNA and is described further below. FIG. 10 shows the ribosome "wait time" plot of frameshifting gene prfB. The ribosome "pauses" at the frameshift site (codon 26) as it is being "displaced." Li et al. [49] also proposed that the ribosome "pauses" at the SD-like sequence in prfB due to SD:aSD binding; however, they do not propose a biophysical mechanism for the pause.

Total Wait Time is the sum of all the ribosome wait time at each codon. Total Wait Time can be used as an indicator of a gene's translation efficiency.

Translation Bottlenecks

While Total Wait Time is a good "global" predictor of protein yield, a "local" predictor index may be a better estimator. Because mRNA is concurrently translated into proteins by multiple ribosomes, multiple "slow" translation regions clustered in local proximity are likely to be more detrimental to yield than impeding regions distributed across the gene. Two genes can have the same total cycle but different "slow" translation clustering sites. This is refered to as "translation bottlenecks" or "ribosome traffic jams". To compute the local translation bottleneck index, a summing sliding window of size 20 codons (i.e., an approximate ribosome footprint on the mRNA [67]) was used. The ribosome "wait times" were summed within this window and plotted on a translation bottleneck plot, as shown in FIG. 11. The window was then advanced one codon, and the sum was recomputed and then plotted as the next value. The traffic jam principle states that the translation efficiency of a gene is bottlenecked by slowest region of translation. Therefore, the max peak (BNI) of the translation bottleneck plot (FIG. 11) was used as the yield predictor index to determine the gene's translation efficiency; the max peak represents the slowest region during translation. BNI stands for bottleneck index and shows the location of the slowest ribosome traffic jam. The mathematics to calculate the translation bottleneck plot and BNI is described below. BNI is equivalent to the maximum sum in a translation bottleneck plot. Bottlenecks also exist during intiation and termination, however, these are not automatically computed in the model. Bottlenecks at inititation and termination can be added manually to improve protein yield predictions.

Gene Optimization

Without being bound by theory, it is postulated that keeping the displacement of a gene close to zero and maximizing tRNA arrival time by using the most abundant aa-tRNA decreases ribosome wait time and translation bottleneck and therefore increases protein yield. A displacement close to zero ensures that the A-site is aligned close to the zero reading frame. This can be accomplished by choosing the codon that codes for the most abundant aa-tRNA while keeping the phase angle of the gene close to the "species angle" [53]. This results in minimal "spring" compression or extension during translocation and therefore minimizes force and displacement. Optimizing in this manner increases ribosome speed by using the most abundant tRNA and maximizing tRNA binding accuracy by minimizing displacement. The result is that ribosome wait times and translation bottlenecks will be reduced throughout translation elongation. Therefore, total ribosome wait time and BNI will also be lowered. Gene designs incorporating these concepts are made by changing the genetic sequence using synonymous codons while conserving the amino acid sequence. Conversely, genes can be altered to make protein production "less optimal". A decrease in protein yield, with potential applications in pathway optimization and production of "toxic" protein can be accomplished by keeping displacement further away from 0 but between −1 and +1 to avoid possible frameshifts. This increases the ribosome wait time at each codon.

This method is feasible at low mRNA transcript levels when the aa-tRNA abundance pool is not taxed and depleted. However, at high mRNA transcript levels, it is best to spread the workload between many different tRNA (coding for the same amino acid) rather than using one single tRNA or a single set of tRNA. This relates to the "recharge" rates of tRNA from uncharge to charge [60,61,62,63]. One still needs to stay close to the species angle while spreading the workload across multiple tRNA to avoid displacing the ribosome.

There are 61 codons coding for 20 amino acids using 45 different tRNA species [64]. This implies that amino acids have multiple codons coding for multiple aa-tRNAs. For example serine has 6 codons coding for 4 different serine-tRNAs. This was explained in the wobble phenomenon by Crick et al. [65]. However, not all codons code the most abundant tRNA. Valine, for example, has four codons (GUA, GUC, GUG, GUU) coding for three valine-tRNA (val1, val2a, val2b) [64]. Only GUU codes for all three tRNA and is considered "the codon that codes the most abundant tRNA". GUA and GUG codes for val1, and GUC codes for val2a and val2b. tRNA val1 is the most abundant out of the three valine-tRNA. The second most abundant codon is GUA and GUG; tRNA abudance information can be found in Dong et al. [64]. Table 1 lists the amino acids, codons, tRNA, and tRNA abundance for the codons. The sum of abundances for the respective tRNA is used when a codon codes for more than one tRNA; i.e., the tRNA abundance of valine codon GUU is the sum of the abundance for val1, val2a, and val2b tRNAs. Table 1 also shows the codon preference in gene optimization. Only amino acids that code for multiple tRNAs are listed.

TABLE 1

Amino acid, codons, cognate tRNA, and tRNA abundance per codon. tRNA abundance and cognate tRNA information taken from Dong et al. [64]. tRNA abundance is taken from Table 3 in Dong et al. using 0.7 doublings/hour.

| Amino Acid | Codon | tRNA | tRNA Abundance |
|---|---|---|---|
| *ALA | GCA | ala1b | 0.54 |
| ALA | GCC | ala2 | 0.1 |
| *ALA | GCG | ala1b | 0.54 |

TABLE 1-continued

Amino acid, codons, cognate tRNA, and tRNA abundance per codon. tRNA abundance and cognate tRNA information taken from Dong et al. [64]. tRNA abundance is taken from Table 3 in Dong et al. using 0.7 doublings/hour.

| Amino Acid | Codon | tRNA | tRNA Abundance |
|---|---|---|---|
| *ALA | GCU | ala1b | 0.54 |
| ARG | AGA | arg4 | 0.11 |
| ARG | AGG | arg4, 5 | 0.18 |
| *ARG | CGA | arg2 | 0.67 |
| *ARG | CGC | arg2 | 0.67 |
| ARG | CGG | arg3 | 0.12 |
| *ARG | CGU | arg2 | 0.67 |
| GLN | CAA | gln1 | 0.12 |
| *GLN | CAG | gln2 | 0.14 |
| GLY | GGA | gly2 | 0.198 |
| *GLY | GGC | gly3 | 0.7 |
| **GLY | GGG | gly1, 2 | 0.33 |
| *GLY | GGU | gly3 | 0.7 |
| ILE | AUA | ile2 | 0.027 |
| *ILE | AUC | ile1 | 0.513 |
| *ILE | AUU | ile1 | 0.513 |
| LEU | CUA | leu3 | 0.11 |
| LEU | CUC | leu2 | 0.16 |
| *LEU | CUG | leu1, 3 | 0.79 |
| LEU | CUU | leu2 | 0.27 |
| LEU | UUA | leu5 | 0.16 |
| **LEU | UUG | leu4, 5 | 0.45 |
| PRO | CCA | pro3 | 0.09 |
| PRO | CCC | pro2 | 0.12 |
| *PRO | CCG | pro1, 3 | 0.2 |
| *PRO | CCU | pro2, 3 | 0.21 |
| **SER | AGC | ser3 | 0.2 |
| **SER | AGU | ser3 | 0.2 |
| SER | UCA | ser1 | 0.25 |
| SER | UCC | ser5 | 0.12 |
| *SER | UCG | ser1, 2 | 0.3 |
| *SER | UCU | ser1, 5 | 0.37 |
| THR | ACA | thr4 | 0.14 |
| THR | ACC | thr1, 3 | 0.19 |
| **THR | ACG | thr2, 4 | 0.23 |
| *THR | ACU | thr1, 3, 4 | 0.33 |
| **VAL | GUA | val1 | 0.55 |
| VAL | GUC | val2a, val2b | 0.2 |
| **VAL | GUG | val1 | 0.55 |
| *VAL | GUU | val1, 2a, 2b | 0.75 |

*indicates preferred codon used for optimization.
**indicates secondary preferred codon.

Conclusions

A new computational-based biophysical model for translation elongation has been developed to elucidate frameshifting genes prfB, dnaX and to simulate ribosome dynamics during normal translation elongation through an mRNA. The model incorporates an energetic "spring" of 16S rRNA tail and mRNA interactions, ribosome displacement, and aa-tRNA abundance, leading to a ribosome "wait time" parameter for the gene(s) of interest. From those wait time parameters, location of translation bottlenecks can be identified.

This represents a comprehensive strategy for evaluating ribosome dynamics and translational efficiency. The model exists as a fully implemented software package (RiboScan™) that provides a new approach to protein production engineering; this software package will be released as a webserver at [66]. The model can be used for predicting and optimizing genes for heterologous protein production in *E. coli*, can be expanded to different production organisms, and has potential applications for predicting protein synthesis levels from complete genome sequences.

Example 2

The Algorithms and Mathematics

The following Example has been included to provide guidance to one of ordinary skill in the art for practicing representative embodiments of the presently disclosed subject matter. The specific example and equations that follow are only intended for the purposes of illustration, and are not to be construed as limiting in any manner to practice the methods of the present invention.

The ribosome spring model and ribosome displacement as described above are modeled using a step-size integrator and a "probability cycle" algorithm. This probability cycle algorithm calculates ribosome displacement and ribosome "wait time" at every codon using the force convolved with the probabilities of picking up an aminoacyl-tRNA (aa-tRNA). The ribosome is displaced at every "cycle" by a step size function which is computed as the force multiplied by a step size constant, delta T (dT); a cycle is defined as the state in which the ribosome has not picked up an aa-RNA. The probability cycle is described further below.

The force exerted on the ribosome can be calculated using a fundamental law of physics: force equals negative change in energy with respect to change in distance. The free energy signal captures the energetic binding of the 16S rRNA tail:mRNA with respect to distance (displacement) and is modeled using a sinusoid or polynomial. Therefore, the force from the spring is computed as the negative derivative of the free energy signal; the derivative of the free energy signal represents the change in energy with respect to change in distance. Calculations of force and free energy signal are described further below.

Three probabilities are used to determine if the ribosome has "picked up" the aa-tRNA from the three reading frames. Another probability is used to determine if the ribosome has not picked up an aa-tRNA and "do nothing" which re-executes the cycle. The probabilities of picking up an aa-tRNA are computed as a function of the "view curve" and of the aa-tRNA abundance for codons in the three reading frames. The view curve models the degree to which the A-site "sees" each of the three codons in the three reading frame as a function of ribosome displacement. Descriptions of the view curve and aa-tRNA abundance are described further below.

After the ribosome picks up the next aa-tRNA, the cycle ends, and the ribosome translocates to the next codon. Ribosome displacement is cumulative and does not reset after translocation. The "probability cycle" algorithm is executed at every codon until a stop codon is reached. The "main algorithm" oversees the execution of all the sub-algorithms. The inputs into the algorithm are: 1) the 13 nucleotides from the 16S rRNA "exposed tail", 2) the mRNA sequence with 15 nucleotides before the start codon, and 3) the aa-tRNA abundance for each codon.

The Main Algorithm

The main algorithm begins simulating ribosome translation with codon 2 in the ribosome A-site and codon 1 in the P-site. The ribosome displacement is initialized to 0. The discrete free energy signal is transformed into a continuous free energy signal that is modeled by a sinusoid or polynomial. The sinusoid or polynomial is then superimposed onto displacement which is in units of nucleotides; this continuous free energy signal represents the rigid "spring" of the 16S rRNA tail:mRNA binding. The force from the spring can be computed by taking the derivative of this continuous free energy signal evaluated at the current ribosome displacement.

The probability cycle computes the ribosome displacement at every codon using a step size function convolved with the probabilities of picking an aa-tRNA; i.e., the ribosome is displaced by the step size function every cycle until it picks up an aa-tRNA. The step size function is computed as the force evaluated at the current displacement multiplied by a step size delta T (dT). Ribosome displacement changes every cycle; thus, the force exerted on the ribosome changes as well. After the ribosome has picked up an aa-tRNA, the ribosome will 1) frameshift if it picks up the wrong aa-tRNA in the +1 or −1 reading frame then translocate, or 2) perform normal in-frame translocation to the next codon if it picked up the aa-tRNA in the 0 reading frame.

Ribosome displacement from the previous codon is cumulative and does not reset. After translocation, the new force is computed from the new continuous free energy signal at the new ribosome displacement position, and the "probability cycle" algorithm is executed for that codon. The ribosome "wait time" at each codon is determined by the number of times the probability cycles are executed; the wait time is a measure of the amount of cycles needed for the ribosome to pick up an aa-tRNA. The main algorithm executes until a stop codon is recognized, which terminates the ribosome translation simulation. Refer to FIG. 12 for the flow chart of the main algorithm.

The Probability Cycle

The probability cycle algorithm computes ribosome displacement at each codon using a step size function convolved with the probabilities of picking up or not picking up an aa-tRNA. The ribosome is displaced at every cycle by a step size function that is computed as the force at the current ribosome displacement multiplied by step size constant delta T (dT) as shown below. The force calculation is described further below. dT is a parameter that can be adjusted. The force changes every time the cycle is re-executed because the ribosome displacement has also changed. Therefore, the force and ribosome displacement are co-dependent on each other.

$$RD_{New} = RD_{current} + \text{force}(RD_{current}) \cdot dT$$

$RD_{New}$ is the new ribosome displacement calculated at every cycle, $RD_{current}$ is the current ribosome displacement, and dT is a step size constant. At start of translation, $RD_{current}$ is initialized to 0.

$RD_{New}$ becomes $RD_{current}$ at the beginning of each cycle. $RD_{current}$ does not reset and keeps the same value after translocation.

The probability cycle repeats until the ribosome has picked up an aa-tRNA, which is modeled by the four probabilities. The four probabilities are defined as $P_{-1}$, $P_0$, $P_{+1}$, and $P_n$ where $P_{-1}$, $P_0$, and $P_{+1}$ are the probabilities of picking up the aa-tRNA in the −1, 0, +1 reading frames, respectively, and Pu is the probability of not picking up an aa-tRNA and re-iterating through the cycle.

The probabilities of picking up an aa-tRNA are computed as a function of the "view curve" (the degree to which the A-site "sees" the codon in the respective reading frame) and aa-tRNA abundance for the respective reading frames. A ribosome that is more displaced "sees" less of the codon in the 0 reading frame and more of the codon in the adjacent reading frame. The probability of picking up an aa-tRNA in a given reading frame is the product of how much of the codon is seen by the A site, as modeled by the view curve, and the aa-tRNA abundance for that codon. Therefore, a displaced ribosome has a smaller chance of picking up the aa-tRNA in the 0 reading frame and a greater chance of picking up the aa-tRNA in the adjacent reading frame compared to a non-displaced ribosome. The view curve and aa-tRNA abundance are described further below.

A probability that "wins" is defined by having the greatest value relative to the other probabilities. If $P_0$ "wins", (i.e. the ribosome has picked up the aa-tRNA in the 0 reading frame), then the probability cycle terminates, and the ribosome does an in-frame translocation to the next codon. If $P_{-1}$ wins, the ribosome picks up the aa-tRNA in the −1 reading frame, "frameshifts" to the −1 reading frame, and then translocate in the new reading frame. If $P_{+1}$ wins, the ribosome picks up the aa-tRNA in the +1 reading frame, "frameshifts" to the +1 reading frame, and then translocate in the new reading frame. In this context, "frameshifting" means that the probabilities and force for the next codon are computed from the perspective of the new reading frame as opposed to the 0 reading frame, ribosome displacement still remains the same. If $P_n$ wins, the ribosome is still waiting for the delivery of aa-tRNA, and the algorithm re-executes the probability cycle; therefore, the ribosome is again displaced by the step size function, and the probabilities are re-computed. The probability cycle continues until either $P_{-1}$, $P_0$, or $P_{+1}$ wins $P_{-1}$, $P_0$, and $P_{+1}$ are computed "cumulatively" at every cycle i by calculating the probabilities of not picking an aa-tRNA ($\overline{P}_{-1}$, $\overline{P}_0$, $\overline{P}_{+1}$) at every cycle i then subtracting those probabilities from 1 as follows:

$$\overline{P}_{-1}^i = \overline{P}_{-1}^{i-1} * (1-NF \& (VC_{-1}(RD_{current})*TA_{-1}))$$

$$\overline{P}_0^i = \overline{P}_0^{i-1} * (1-NF*VC_0(RD_{current})*TA_0)$$

$$\overline{P}_{+1}^i = \overline{P}_{+1}^{i-1} * (1-NF*(VC_{+1}(RD_{current})*TA_{+1}))$$

i is the index for of the current cycle; therefore $\overline{P}_0^{i-1}$ would be the probability computed from the previous cycle. NF is the normalization constant to compensate for changes in dT. $VC_{-1}$, $VC_0$, $VC_{+1}$ is the view curve of the −1, 0, +1 reading frame respectively. $RD_{current}$ is the current ribosome displacement. $TA_{-1}$, $TA_0$, $TA_{+1}$ is the aa-tRNA abundance of the codon in the −1, 0, +1 reading frame respectively View curves and aa-tRNA abundance are described further below.

Therefore, $P_{-1}^i$, $P_0^i$, $P_{+1}^i$ can be computed as:

$$P_{-1}^i = 1 - \overline{P}_{-1}^i$$

$$P_0^i = 1 - \overline{P}_0^i$$

$$P_{+1}^i = 1 - \overline{P}_{+1}^i$$

And $P_n$ is computed as:

$$P_n = 1 - (P_{-1}^i + P_0^i + P_{+1}^i)$$

Modeling $P_n$ in this manner implies that the aa-tRNAs of the respective reading frame are competing for binding to the A-site of the ribosome.

Pseudo Code of "The Probability Cycle":

```
// Initial Conditions:
    P̄₋₁ = 1, P̄₀ = 1, P̄₊₁ = 1, Ribosome Displacement (RD) = 0, dT = 0.004, Cycle Count = 0
    Normalization Constant (NF) = dT/0.004
// Start probability cycle at codon 2
// probability of not picking up a tRNA is set to 1 at beginning of cycle
   (P̄₋₁ = 1, P̄₀ = 1, P̄₊₁ = 1)
// Cycle Begins
1. RD_New = RD_current + force (RD_current) * dT   // displace ribosome
2. RD_Current = RD_New      // RD is ribosome displacement
3. Compute cumulative probabilities: P̄₋₁ⁱ, P̄₀ⁱ, P̄₊₁ⁱ // probability of not picking up aa-tRNA
    i. P̄₋₁ = P̄₋₁ * (1 − NF * (VC₋₁(RD_current) * TA₋₁))
    ii. P̄₀ = P̄₀ * (1 − NF * (VC₀(RD_current) * TA₀))
    iii. P̄₊₁ = P̄₊₁ * (1 − NF * (VC₊₁(RD_current) * TA₊₁))
4. Compute P₋₁, P₀, P₊₁, Pₙ // probability of picking up aa-tRNA
    i. P₋₁ = (1 − P̄₋₁); P₀ = (1 − P̄₀), P₊₁ = (1 − P̄₊₁)
    ii. Pₙ = 1 − sum (P₋₁, P₀, P₊₁)
5. Cycle Count = Cycle Count + 1 // compute ribosome wait time
6. Repeat #1 until Pₙ is less than P₋₁, P₀, or P₊₁.
// Cycle Ended
7. Ribosome "wait time" at this codon = Cycle Count
8. Ribosome displacement at this codon = RD_current
9. If ribosome displacement is greater than +1 units, "frameshift" to +1 reading frame and translocate
10. If ribosome displacement is less than −1 units, "frameshift" to −1 reading frame and translocate
11. If ribosome displacement is between −1 and +1 units, translocate in-frame to next codon
12. Keep current ribosome displacement (RD_Current) the same after translocation. Do not reset.
13. P̄₋₁ = P̄₀ = P̄₊₁ = 1, Cycle Count = 0. // reset probabilities and cycle count every cycle
14. Repeat #1 for next codon until a stop codon reached. If stop codon reached, terminate translation
```

Output of the Probability Cycle

The output of the probability cycle is ribosome displacement and ribosome wait time at each codon. Therefore, a graph of the ribosome displacement of a gene can be plotted, as shown in FIG. 13. This is called the ribosome displacement plot. Ribosome wait time is calculated as the number of cycles required for the ribosome to pick up an aa-tRNA as described in the pseudo code; therefore, ribosome wait time is a function of ribosome displacement, aa-tRNA abundance, and force. A graph of the ribosome wait time of a gene can also be plotted, as shown in FIG. 14.

Mathematics of the Bottleneck Plot and Bottleneck Index (BNI)

The ribosome wait times (as shown in FIG. 14) were used to calculate the translation bottleneck plot and bottleneck index (BNI), which is depicted in FIG. 15. The translation bottleneck plot and BNI show locations of ribosome traffic jams as explained above.

The computations used to calculate the translation bottleneck plot and BNI are as follows:

Let WS be the window size of the sliding window in units of codons. WS corresponds to the length of the ribosome footprint on the mRNA [70], which is approximately 20 codons. Let $PS_i$ be the partial sum of the ribosome wait times in the sliding window where i is the "codon position" on the translation bottleneck plot. Let $WT_j$ be the ribosome wait time at the $j^{th}$ codon position on the ribosome wait time plot where j is the codon position on the ribosome wait time plot. Therefore the partial sum at the $i^{th}$ position ($PS_i$) on the translation bottleneck plot can be computed as:

$$PS_i = \sum_{j=i}^{j+WS-1} WT_j$$

where the max value for i is the window size (WS) subtracted from the max codon position in the ribosome wait time plot (or length of the gene in codons). For example, if the gene length is 200 codons, then the max codon position in the ribosome wait time plot is 200 codons. Therefore, the max value for i is 180. So the partial sum is calculated from codon position i=1 to codon position i=180 where the partial sum at i=180 is the sum of the ribosome wait time from j=180 to j=200. The partial sum at codon position i=180 represents the bottleneck for the ribosome to translate the last 20 codons.

The bottleneck index (BNI) is calculated by taking the maximum of the partial sums on the translation bottleneck plot:

$$BNI=MAX(PS_i)$$

Calculating Force from "Springy" 16S rRNA Tail

The probability cycle uses the force to displace the ribosome an incremental amount each "cycle". The fundamental law of physics states that the force equals the change in energy with respect to the change in distance. The continuous free energy signal captures the energetic binding of the 16S rRNA tail:mRNA with respect to distance (displacement) at every codon. Therefore, the force is calculated as the derivative of the continuous free energy signal; this derivative represents the change in energy with respect to change in distance. However, before the force can be calculated, the continuous free energy signal at each codon must first be computed.

Calculating the Continuous Free Energy Signal

The continuous free energy signal is computed from the discrete free energies of the Watson-Crick binding between the 16S rRNA exposed tail (3'-auuccuccacuag-5') (SEQ ID NO:16) and the mRNA. The discrete free energy signal can be converted into a continuous free energy signal by fitting the discrete free energy value on either a sinusoid or polynomial. The sinusoid uses three discrete free energy values ($\Delta G_{n-1}$, $\Delta G_n$, $\Delta G_{n+1}$) while the polynomial uses five discrete free energy values ($\Delta G_{n-2}$, $\Delta G_{n-1}$, $\Delta G_n$, $\Delta G_{n+1}$, $\Delta G_{n+2}$). The free energy values are calculated using the methods described in Mishra et al. [68]. The free energy values used herein are from the Freier et al. free energy model. All modeling and calculations use the sinusoidal fitting herein. Polynomial fitting is an option that can be used instead of the sinusoidal fit. The sinusoidal fitting is nearly identical to the polynomial fitting.

Center Point and "Tail Distance"

The center point, $\Delta G_n$, of the continuous free energy signal is the free energy calculated when the exposed tail binds five bases away from middle base of the A-site codon (see FIG. 16a). This distance is called the "tail distance" and is a parameter in the model. The tail distance was derived from modeling the frameshift site of prfB. Any distance greater or less than five bases would not frameshift the ribosome and/or keep the ribosome frameshifted in the +1 reading frame after frameshift. Surprisingly, this distance puts the anti-Shine-Dalgarno sequence (3'-UCCUCC-5') of the 16S rRNA tail 5 bases away from the P-site that corresponds to the optimal spacing between the Shine-Dalgarno to start codon at initiation [72]. It I believed that the tail distance may differ from organism to organism.

Discrete Free Energy Indexing

A sinusoid or polynomial fitting method can be used to convert the discrete free energy values into a continuous free energy signal. The sinusoid fitting uses three discrete free energy values annotated as $\Delta G_{n-1}$, $\Delta G_n$, and $\Delta G_{n+1}$, while the polynomial fitting uses five discrete free energy values annotated as $\Delta G_{n-2}$, $\Delta G_{n-1}$, $\Delta G_n$, $\Delta G_{n+1}$, and $\Delta G_{n+2}$. $\Delta G_{n-1}$ is the free energy value calculated when the exposed tail is shifted one base upstream relative to the $\Delta G_n$ binding position, as shown in FIG. 16b. In this position, the tail is 6 bases away from the center of the A-site. $\Delta G_{n+1}$ is the free energy value calculated when the exposed tail is shifted one base downstream relative to the $\Delta G_n$ binding position, as shown in FIG. 16c. In this position, the tail is 4 bases away from the center of the A-site. $\Delta G_{n-2}$ is free energy values calculated by shifting the exposed tail 2 bases upstream relative to the $\Delta G_n$ binding position or 7 bases from the center of the A-site. $\Delta G_{n+2}$ indicates free energy values calculated by shifting the exposed tail 2 bases downstream relative to the $\Delta G_n$ binding position or 3 bases away from the center of the A-site.

Sinusoidal Fitting of Discrete Free Energy Signal and Force Calculations

The sinusoidal fitting uses discrete free energy values ($\Delta G_{n-1}$, $\Delta G_n$, and $\Delta G_{n+1}$) to convert to a continuous free energy signal. For simplicity in annotation, $\Delta G_{n-1}$, $\Delta G_n$, and $\Delta G_{n+1}$ are re-annotated as A, B, and C, respectively. Therefore, the continuous free energy signal can be calculated using the following method. Compute the DC constant from the free energy values.

$$DC = \frac{A+B+C}{3}$$

Subtract DC constant from the free energy values. DC is not needed to compute the force.

$$a=A-DC$$

$$b=B-DC$$

$$c=C-DC$$

Modified free energy values a, b, and c, can be fitted on a sinusoid with a frequency of ⅓ cycles per nucleotide; this can be done because the average free energy signal has a frequency of ⅓ cycles per nucleotide [73,74]. a is fitted at zero degrees on the sinusoidal as defined below. b is fitted with a 120 degree phase shift on the sinusoid as defined below. c is fitted with a 240 degrees phase shift on the sinusoidal as defined below.

$$a = M \cdot \sin(\Phi)$$

$$b = M \cdot \sin\left(\Phi + \frac{2\pi}{3}\right)$$

$$c = M \cdot \sin\left(\Phi + \frac{4\pi}{3}\right)$$

This leaves 3 equations and 2 unknowns (M and ϕ). The last two equations are expanded using the following trigonometric identity for sine expansion:

$$\sin(x+y)=\sin(x)\cdot\cos(y)+\cos(x)\cdot\sin(y)$$

Subtracting the resulting expanded equations will result in:

$$M \cdot \cos(\Phi) = \frac{b-c}{\sqrt{3}}$$

Using the trigonometric identity for the expansion of tangent:

$$\tan(\Phi) = \frac{\sin\Phi}{\cos\Phi}$$

and equations above, φ can be computed:

$$\Phi = \tan^{-1}\left(\frac{a \cdot \sqrt{3}}{b-c}\right)$$

Using the trigonometric identity:

$$\sin(x)^2 + \cos(x)^2 = 1 \quad (5.22)$$

And equations above, M can be computed:

$$M = \sqrt{(a)^2 + \frac{(b-c)^2}{3}}$$

The continuous free energy signal using sinusoidal fitting is then superimposed on displacement units of −3 to 3:

$$M \cdot \sin\left(\frac{x \cdot \pi}{3} + \Phi\right)$$

The signal is then shifted for minimal energy at the species angle and to compensate for the "tail distance". The following equation models the energy of the ribosome "spring" as function of ribosome displacement (RD)

$$\text{Energy}(RD) = M \cdot \sin\left(\frac{x \cdot \pi}{3} + \Phi - \theta_{sp} - \delta - \frac{\pi}{2}\right)$$

$\theta_{sp}$ (radians) is the "species angle": The species angle for *E. coli* is −23 degrees or 0.401 radian. δ is the shift to compensate for the tail distance. This tail distance is 5 bases for *E. coli* as mentioned elsewhere herein.

$$\delta = \text{tail distance} \cdot \frac{2 \cdot \pi}{3}$$

The shift in tail distance is required because the species angle was calculated every 3, 6, 9 nucleotides rather than every 2, 5, 8 nucleotides.

The force is calculated as −Δ energy/Δ distance. Hence, the force is calculated as the derivative of Energy (RD). Therefore, the force as function of ribosome displacement is:

$$\text{force}(RD) = M \cdot 3 \cdot \pi \cdot \cos\left(\frac{x \cdot \pi}{3} + \Phi - \theta_{sp} - \delta - \frac{\pi}{2}\right)$$

Alternatively, this equation can be written as a sine function in which a phase shift of $$\frac{\pi}{2}$$

is applied:

$$\text{force}(RD) = -M \cdot 3 \cdot \pi \cdot \sin\left(\frac{x \cdot \pi}{3} + \Phi - \theta_{sp} - \delta\right)$$

Either equation for force (RD) can be used in the equation of the probability cycle to compute the force as a function of ribosome displacement if a sinusoidal fitting is used.

Polynomial Fitting of Discrete Free Energy Signal and Force Calculations

A polynomial fitting of degree 4 can also be used to convert the discrete free energy signal into a continuous free energy signal. The fitting uses the 5 discrete free energy values: $\Delta G_{n-2}$, $\Delta G_{n-1}$, $\Delta G_n$, $\Delta G_{n+1}$, and $\Delta G_{n+2}$. For simplicity, $\Delta G_{n-2}$, $\Delta G_{n-1}$, $\Delta G_n$, $\Delta G_{n+1}$: $\Delta G_{n+2}$, are referred to as A, B, C, D, E respectively. A polynomial of degree 4 is generalized using the following equation:

$$y = a_0 + a_1 x + a_2 \cdot x^2 + a_3 \cdot x^3 + a_4 \cdot x^4$$

Therefore, the free energy values A, B, C, D), and E are fitted on a polynomial function which is represented as 5 polynomial equations:

$$A = a_0 + a_1 \cdot x + a_2 \cdot x^2 + a_3 \cdot x^3 + a_4 \cdot x^4$$

$$B = a_0 + a_1 \cdot x + a_2 \cdot x^2 + a_3 \cdot x^3 + a_4 \cdot x^4$$

$$C = a_0 + a_1 \cdot x + a_2 \cdot x^2 + a_3 \cdot x^3 + a_4 \cdot x^4$$

$$D = a_0 + a_1 x + a_2 x^2 + a_3 x^3 + a_1 x^4$$

$$E = a_0 + a_1 x + a_2 \cdot x^2 + a_3 \cdot x^3 + a_1 \cdot x^4$$

where x is in displacement units. The free energy value A is fitted on the polynomial at x equals −4, B is fitted at x equals −2, C is fitted at x equals 0, D is fitted at x equals 2, and E is fitted at x equals 4. The following equations are derived by substituting in the x values for each free energy value A, B, C, D, E:

$$A = a_0 + a_1 \cdot (-4) + a_2 \cdot (-4)^2 + a_3 \cdot -(4)^3 + a_4 \cdot -(4)^4$$

$$B = a_0 + a_1 \cdot (-2) + a_2 \cdot (-2)^2 + a_3 \cdot (-2)^3 + a_4 \cdot (-2)^4$$

$$C = a_0 + a_1 \cdot (0) + a_2 \cdot (0)^2 + a_3 \cdot (0)^3 + a_4 \cdot (0)^4$$

$$D = a_0 + a_1 \cdot 2 + a_2 \cdot (2)^2 + a_3 \cdot (2)^3 + a_4 \cdot (2)^4$$

$$E = a_0 + a_1 (4) + a_2 \cdot (4)^2 + a_3 \cdot (4)^3 + a_4 \cdot (4)^4$$

Thus, there are 5 equations and 5 unknowns ($a_0$, $a_1$, $a_2$, $a_3$, $a_4$). The five coefficients ($a_0$, $a_1$, $a_2$, $a_3$, $a_4$) can be solved using the following matrix:

$$\begin{vmatrix} 1 & x & x^2 & x^3 & x^4 \\ 1 & x & x^2 & x^3 & x^4 \\ 1 & x & x^2 & x^3 & x^4 \\ 1 & x & x^2 & x^3 & x^4 \\ 1 & x & x^2 & x^3 & x^4 \end{vmatrix} \begin{vmatrix} a_0 \\ a_1 \\ a_2 \\ a_3 \\ a_4 \end{vmatrix} = \begin{vmatrix} A \\ B \\ C \\ D \\ E \end{vmatrix}$$

Substituting in values of x that correspond to the free energy values:

$$\begin{vmatrix} 1 & -4 & -4^2 & -4^3 & -4^4 \\ 1 & -2 & -2^2 & -2^3 & -2^4 \\ 1 & 0 & 0^2 & 0^3 & 0^4 \\ 1 & 2 & 2^2 & 2^3 & 2^4 \\ 1 & 4 & 4^2 & 4^3 & 4^4 \end{vmatrix} \begin{vmatrix} a_0 \\ a_1 \\ a_2 \\ a_3 \\ a_4 \end{vmatrix} = \begin{vmatrix} A \\ B \\ C \\ D \\ E \end{vmatrix}$$

and using this matrix equation:

$$a = (X^T X)^{-1} X^T$$

Therefore solving for $a_0$, $a_1$, $a_2$, $a_3$, $a_4$ in terms of A, B, C, D, E:

$$a_4 = \frac{A+E}{384} - \frac{B+D}{96} + \frac{C}{64}$$

$$a_3 = \frac{B-D}{48} - \frac{A-E}{96}$$

$$a_2 = \frac{B+D}{6} - \frac{A+E}{96} - \frac{5 \cdot C}{16}$$

$$a_1 = \frac{A+E}{24} - \frac{B+D}{3}$$

$$a_0 = C$$

where A, B, C, D, E are free energy values $\Delta G_{n-2}$, $\Delta G_{n-1}$, $\Delta G_n$, $\Delta G_{n+1}$, and $\Delta G_{n+2}$, respectively. After solving for $a_0$, $a_1$, $a_2$, $a_3$, and $a_4$, the energy of ribosome spring as function of displacement is:

$$\text{Energy}(RD) = a_0 + a_1 \cdot (x-\tau) + a_2 \cdot (x-\tau)^2 + a_3 \cdot (x-\tau)^3 + a_1 \cdot (x-\tau)^4$$

where $\tau$ is the shift for minimal energy at species angle and tail distance. $\tau$ is calculated as:

$$\tau = \frac{-3 \cdot \theta_{sp}}{\pi} + 0.5$$

where $\theta_{sp}$ is the species angle in radians.

The force is then computed as $-\Delta$ energy/$\Delta$distance. This means the force is the derivative of the equation for Energy (RD). Therefore, the force as function of ribosome displacement is:

$$\text{force}(RD) = -(a_1 + a_2 \cdot 2 \cdot (x-\tau) + a_3 \cdot 3 \cdot (x-\tau)^2 + a_4 \cdot 4 \cdot (x-\tau)^3)$$

This equation can be used in the equation of the probability cycle to compute the force as a function of ribosome displacement if polynomial fitting is used.

The "Big Picture" of Energetics and Force Calculations

At every codon during translation, the aSD of the 16S rRNA exposed tail binds with the mRNA. The binding distance relative to the P-site determines if the spring is compressed, extended, or relaxed. Bindings that locate the aSD (3'-UCCUCC-5') 5 bases away from the P-site result in a relaxed spring (see FIG. 6). In the simulation, a relaxed spring is illustrated as having the minimal energy of the free energy signal close to the center of the A-site (FIG. 17). The force near minimal energy is close to zero, and therefore, ribosome displacement is small. Bindings that locate the aSD closer than 5 bases away from the P-site compress the spring. Bindings that locate the aSD farther than 5 bases away from the P-site extend the spring. The distance of "5 bases" was determined by the "tail distance" when modeling the frameshift site of prfB. The change in @ measures the relative binding location of the aSD to the P-site. Changing in the phase angle results in the shifting of the free energy signal relative to the center of the A-site. Therefore, minimal energy may no longer be located near the center of the A-site, resulting in ribosome displacement by the force.

View Curve and Aminoacyl-tRNA Abundance Table

The probability cycle uses the view curve and aminoacyl-tRNA abundance to calculate the probability of picking an aminoacyl-tRNA from the three reading frames. Because there are three reading frames, there are three view curves and three aa-tRNA abundances. The three view curves are $VC_{-1}$, $VC_0$, and $VC_1$. The three aa-tRNA abundances are $TA_{-1}$, $TA_0$, $TA_{+1}$, corresponding to the $-1$, 0, and $+1$ reading frames respectively. A ribosome with greater displacement will see less of the codon in the 0 reading frame and more of the codons in the adjacent reading frames. This decreases the chance of the ribosome picking up the aa-tRNA in the 0 reading frame and increases the chance of picking up the aa-tRNA in the adjacent reading frame.

View Curve

The view curve models the degree of the codon in the respective reading frame that the A-site "sees". For example, when the A-site is in perfect alignment with the 0 reading frame (ribosome displacement is 0), the A-site sees all of the codon in the 0 reading frame and no part of the codon in the $-1$ or $+1$ reading frame (FIG. 18). A displaced ribosome sees both the codon in the 0 reading frame and the adjacent reading frame. For example, when the ribosome displacement is 1, the ribosome sees 50% of the codon in the 0 frame and 50% of the codon in the $+1$ reading frame. This is modeled by the fact that $VC_0 = VC_{+1}$ when the ribosome displacement is 1 (see FIG. 19). The view curve is modeled using the function $\cos x^n$. The current model uses $\cos x^4$. The power of the cosine function n is a parameter that can be adjusted. A greater value of n makes the view curve narrower, while a smaller n makes the view curve wider.

The view curve for the codon in the 0 reading frame ($VC_0$) is modeled using the function $\cos x^4$ evaluated from $-\frac{1}{2}$ pi to $\frac{1}{2}$ pi and superimposed from $-2$ to 2 displacement units (Equation 5.51). Displacement has units of nucleotides where 2 displacement units is 1 nucleotide and 1 displacement unit is $\frac{1}{2}$ nucleotide. The view curve for the codon in the $+1$ reading frame ($VC_{+1}$) is $\cos x^4$ evaluated from 0 to pi and superimposed from 0 to 4 displacement units (Equation 5.53). The view curve for the codon in the $-1$ reading frame ($VC_{-1}$) is $\cos x^4$ evaluated from $-pi$ to 0 and superimposed from $-4$ to 0 displacement units (Equation 5.51).

$$VC_{-1} = \cos\left(\frac{x \cdot \pi}{4} + \frac{1}{2}\pi\right)^n \Big|_{-\pi}^{0}$$

(5.51)

$$VC_0 = \cos\left(\frac{x \cdot \pi}{4}\right)^n \Big|_{-0.5\pi}^{0.5\pi}$$

(5.52)

$$VC_{+1} = \cos\left(\frac{x \cdot \pi}{4} - \frac{1}{2}\pi\right)^n \Big|_{0}^{\pi}$$

(5.53)

$VC_{-1}$, $VC_0$, $VC_{+1}$ is the view curve of the $-1$, 0, $+1$ reading frame, respectively. n is a parameter of the model that can be changed. It is currently set to 4. x is $RD_{current}$ (see pseudo code of probability cycle), the current ribosome displacement value.

Aminoacyl-tRNA Abundance Table

The probability cycle algorithm uses the aminoacyl-tRNA abundance of the codons in the $-1$, 0, and $+1$ reading frame ($TA_{-1}$, $TA_0$, $TA_{+1}$) to calculate the probability of picking up an aa-tRNA for that codon. Aminoacyl-tRNAs with high abundance have a higher chance of being picked up by the ribosome, which decreases the amount of time the ribosome waits at that codon. On the other hand, aminoacyl-tRNAs with lower abundance have a lower chance of being picked by the ribosome, which increases the amount of time the ribosome waits for aa-tRNA delivery. When determining aa-tRNA abundance for codons that code for multiple tRNAs, the sum of the respective aa-tRNA abundance are used. tRNA abundance measurements for *E. coli* at different growth rates can be found in Dong et al. [75]. Table 2 shows the aa-tRNA abundance for each codon derived from tRNA abundance measurements of Dong et al. [75]. When tRNA abundance information is not known, the genomic codon distribution can be used (Table 3) instead. Genomic codon distribution loosely matches intracellular tRNA abundance [75,76,77,78]. tRNA gene copy number can also be used as estimates of aa-tRNA abundance [79,80,81,82]. tRNA abundances are estimates of the actual aa-tRNA abundance. aa-tRNA abundance changes depending on growth conditions and mRNA expression levels; this relates to the "recharge" rates of tRNAs from uncharged to charged states as described in Chapter 3.3.2. The aa-tRNA abundance values (TA) of the respective codon are substituted for $TA_{-1}$, $TA_0$, $TA_{+1}$ of probability cycle equations.

TABLE 2 aa-tRNA abundance per codon derived from Dong et at. Aminoacyl-tRNA abundance is derived tRNA abundance per ribosome at 1.7 doubling per hour from Dong et al. [75]. Stop codons are assigned very small values to indicate low abundance and termination of translation. TA stands for tRNA abundance values used in probability cycle equations.

| Codon | aa-tRNA Abundance (TA) |
|---|---|
| aaa | 0.1427 |
| aac | 0.0973 |
| aag | 0.1427 |
| aau | 0.0973 |
| aca | 0.0779 |
| acc | 0.0843 |
| acg | 0.1233 |
| acu | 0.1622 |
| aga | 0.0519 |
| agc | 0.0908 |
| agg | 0.0908 |
| agu | 0.0908 |
| aua | 0.0159 |
| auc | 0.2891 |
| aug | 0.0649 |
| auu | 0.2891 |
| caa | 0.0519 |
| cac | 0.0519 |
| cag | 0.0843 |
| cau | 0.0519 |
| cca | 0.0389 |
| ccc | 0.0649 |
| ccg | 0.0843 |
| ccu | 0.1038 |
| cga | 0.3893 |
| cgc | 0.3893 |
| cgg | 0.0389 |
| cgu | 0.3893 |
| cua | 0.0519 |
| cuc | 0.0779 |
| cug | 0.4022 |
| cuu | 0.1298 |
| gaa | 0.3958 |
| gac | 0.1946 |
| gag | 0.3958 |
| gau | 0.1946 |
| gca | 0.2855 |
| gcc | 0.0519 |
| gcg | 0.2855 |
| gcu | 0.2855 |
| gga | 0.109 |
| ggc | 0.3244 |
| ggg | 0.1817 |
| ggu | 0.3244 |

TABLE 2-continued aa-tRNA abundance per codon derived from Dong et at. Aminoacyl-tRNA abundance is derived tRNA abundance per ribosome at 1.7 doubling per hour from Dong et al. [75]. Stop codons are assigned very small values to indicate low abundance and termination of translation. TA stands for tRNA abundance values used in probability cycle equations.

| Codon | aa-tRNA Abundance (TA) |
|---|---|
| gua | 0.3114 |
| guc | 0.1038 |
| gug | 0.3114 |
| guu | 0.4152 |
| uaa | 0.000001 |
| uac | 0.1622 |
| uag | 0.000001 |
| uau | 0.1622 |
| uca | 0.1103 |
| ucc | 0.0584 |
| ucg | 0.1298 |
| ucu | 0.1687 |
| uga | 0.000001 |
| ugc | 0.1168 |
| ugg | 0.0649 |
| ugu | 0.1168 |
| uua | 0.0584 |
| uuc | 0.0779 |
| uug | 0.2141 |
| uuu | 0.0779 |

TABLE 3 aa-tRNA abundance per codon using *E. coli* genomic codon frequency table. Genomic codon frequency table can be found in Nakamura et al. [83]. Stop codons are assigned very small values to indicate low abundance and termination of translation. TA stands for tRNA abundance values used in probability cycle equations.

| Codon | aa-tRNA Abundance (TA) |
|---|---|
| aaa | 0.336 |
| aac | 0.256 |
| aag | 0.133 |
| aau | 0.186 |
| aca | 0.049 |
| acc | 0.245 |
| acg | 0.144 |
| acu | 0.108 |
| aga | 0.03 |
| agc | 0.171 |
| agg | 0.011 |
| agu | 0.127 |
| aua | 0.042 |
| auc | 0.272 |
| aug | 0.268 |
| auu | 0.304 |
| caa | 0.144 |
| cac | 0.068 |
| cag | 0.31 |
| cau | 0.16 |
| cca | 0.106 |
| ccc | 0.075 |
| ccg | 0.244 |
| ccu | 0.05 |
| cga | 0.035 |
| cgc | 0.243 |
| cgg | 0.064 |
| cgu | 0.2 |
| cua | 0.028 |
| cuc | 0.071 |
| cug | 0.571 |
| cuu | 0.11 |

TABLE 3-continued aa-tRNA abundance per codon using *E. coli* genomic codon frequency table. Genomic codon frequency table can be found in Nakamura et al. [83]. Stop codons are assigned very small values to indicate low abundance and termination of translation. TA stands for tRNA abundance values used in probability cycle equations.

| Codon | aa-tRNA Abundance (TA) |
|---|---|
| gaa | 0.397 |
| gac | 0.211 |
| gag | 0.18 |
| gau | 0.292 |
| gca | 0.201 |
| gcc | 0.287 |
| gcg | 0.339 |
| gcu | 0.152 |
| gga | 0.059 |
| ggc | 0.278 |
| ggg | 0.14 |
| ggu | 0.247 |
| gua | 0.129 |
| guc | 0.173 |
| gug | 0.293 |
| guu | 0.182 |
| uaa | 0.000001 |
| uac | 0.162 |
| uag | 0.000001 |
| uau | 0.161 |
| uca | 0.08 |
| ucc | 0.076 |
| ucg | 0.079 |
| ucu | 0.094 |
| uga | 0.000001 |
| ugc | 0.064 |
| ugg | 0.132 |
| ugu | 0.041 |
| uua | 0.128 |
| uuc | 0.185 |
| uug | 0.156 |
| uuu | 0.202 |

Gene Optimization Algorithm

Genes were optimized using the concepts and methods described above. The optimization chooses the codons that code for the most abundant aa-tRNA while maintaining a phase angle that is close to the species angle. The algorithm optimizes a gene by redesigning the entire coding region from the second codon (after AUG) to the stop codon. Six codons were optimized concurrently. The optimization algorithm starts with the first 6 codons beginning at codon 2, optimizes those 6 codons, then moves to the next 6 codons until the end of the gene is reached. Codons where changed using synonymous codons while conserving the amino acid sequence.

For each set of 6 codons, a list of all the different combinations for those codons was determined. A "total value" for each permutation of the 6 codons was calculated. The total value is computed by taking the product of each codon's "value". The codon's value can be defined as either the aa-tRNA abundance or a user "predefined" value. If the codon's value is the aa-tRNA abundance, then the algorithm will almost always use the same codon in the set of synonymous codons. Using a predefined value is helpful in disbursing the codon usage and thus spreading the usage of aa-tRNA. For example, proline codons CCU and CCG can be assign the same value while proline codons CCC and CCA can be assigned a lower value. This will distribute the usage of CCU and CCG codons evenly while limiting the usage of CCC and CCA codons. Codon preferences are shown in Table 1.

The permutations were then ranked from highest to lowest by "total value". The algorithm then takes the highest ranking permutation and computes the phase angle of the 6 codons. If the phase angle of the permutation is within a predefined "threshold" of the species angle, then that permutation is chosen as the "optimized" permutation, and the algorithm moves to the next 6 codons in the gene. However, if the phase angle is not within the predefined threshold of the species angle, the algorithm chooses the next permutation in the list until a permutation is found that is within the range of the species angle. If no permutation within the threshold of the species angle is found, then the highest ranking permutation is used as the "optimized" permutation. The calculation of the species angle ($\theta_{sp}$) and "phase angle" of the partially optimized gene and its 6-codon permutation is described in [68,84]. The phase angle is computed by calculating $\phi_k$ for the partially optimized sequence (including the new 6 codon permutation); calculation of $\phi_k$ is published in [68]. After finding the optimized permutation, the algorithm moves to the next 6 codons and repeats the process until the end of the gene. The resulting product is an optimized gene that uses the codons that code for the most abundant aa-tRNAs or the sets of codons that code for multiple abundant aa-tRNAs, all while maintaining the phase angle close to the species angle.

Optimized gene sequence is then processed by the model to determine ribosome displacement, translation bottlenecks (BNI), and total wait cycle. These parameters are compared to that of the wildtype gene or the parameters of codon bias-optimized gene to determine if the gene can be further optimized; if ribosome displacement is not close enough to zero, then BNI or total wait can still be lowered. The "most optimized" sequence can be determined empirically by (1) varying the "acceptable threshold" of the gene's phase angle compared to the species' angle and also by (2) changing preferred codon(s) through varying the codon's "value".

The aforementioned gene optimization algorithm is best described as a heuristic algorithm rather than a classical optimization algorithm with defined optimal conditions. However, the algorithm is deterministic rather than stochastic because it outputs the same sequence given the same inputs rather than outputting different sequences each time. The algorithm improves the translation efficiency of genes based on using the most abundant aa-tRNA (through codon usage) while also reducing ribosome displacement and force. By using these principles, ribosome wait times and bottlenecks are lowered throughout translation elongation. This results in a "more optimal" gene rather than the "most optimal" gene because the most optimal conditions are not known. In theory, there can be multiple "optimal" gene variants that have the same displacement, wait times, and BNI.

CONCLUSIONS

Algorithms and mathematical equations were developed to model the ribosome "spring" action that results in ribosome displacement. At every codon, the "probability cycle" displaces the ribosome a small step size during each "cycle" until the ribosome "picks up" an aminoacyl-tRNA. The degree of ribosome displacement is a function of the force and how long the ribosome has to wait for the delivery of the next amino-acyl tRNA, which is related to aa-tRNA abundance. The force is calculated by converting the discrete free energy signal into a continuous free energy signal (using sinusoidal fitting or polynomial fitting) and taking the derivative of this continuous free energy signal. The amount of time the ribosome spends waiting for the delivery of the next aminoacyl-tRNA is modeled by multiple probabilities convolved with the "view curve" and aminoacyl-tRNA abundance. The probability cycle convolves the energetic binding of the "springy" 16S rRNA exposed tail (the force exerted on the ribosome from this spring) with the aminoacyl-tRNA abundance to output ribosome displacement and ribosome wait time at every codon. See FIG. 20 for a graphical illustration of the algorithms. Parameters considered in the algorithm include the step size constant delta T (dT), power of the cosine function (n) for the "view curve," the "tail distance," normalization constant (NF) for the probabilities, and the aminoacyl-tRNA abundance information. The accuracy of the model depends on all these parameters. A gene optimization algorithm was also developed to efficiently optimize genes, which is more efficient and accurate than optimizing genes manually. This algorithm designs genes from scratch by optimizing 6 codons at a time starting with the second codon. Optimization of those 6 codons is a "tradeoff" between choosing codons that closely match the species angle and choosing codons that confer with the best aa-tRNA usage. The aforementioned algorithms and mathematics were incorporated in a fully implemented software package called RiboScan™; this software package will be available as webserver [85]. Outputs of RiboScan™ includes polar plots, ribosome displacement plots, ribosome wait time plots, translation bottleneck plots, and simulations of single ribosome dynamics during translation elongation.

Example 3

Case Studies—Prediction and Optimization

The model's prediction and optimization capabilities were assessed by expressing five model genes: gst (glutathione-S-transferase), pf0132 (alpha-glucosidase), clju_c11880 (alcohol dehydrogenase), and rt8_0542 (endoglucanase and exoglucanase) in *Escherichia coli*. The optimization power of the model was also compared to that of codon bias optimization algorithms as described elsewhere herein. Multiple mRNA variants of GST were also designed and expressed to further verify the model's prediction as compared to that of codon bias's prediction. The codon adaptation index (CAI) by Sharpe et al. was used to measure a gene's codon bias. Measured protein yield (GST activity) was correlated with predicted protein yield for both the codon adapation index (CAI) and the model's index (BNI). The rationale behind comparing the correlations was to demonstrate that determinants of protein yield are not limited to just codon bias but rather encompass a convolution between ribosome displacement, force, and tRNA usage. This convolution leads to new ribosome wait time parameters and translation bottlenecks (BNI) that allow for a superior predictor of protein yield. Description of ribosome wait time parameters and translation bottlenecks is described above.

Gene optimization was performed using the concepts described above. The algorithm used for optimization is described above. Polar plots, ribosome displacement plots, ribosome wait time plots, and translation bottleneck plots were used as analysis tools. Detailed descriptions of the materials and methods used in cloning, expressing, and quantifying protein yield for these genes are described below. Genes were synthesized by either gene synthesis company Genewiz, Inc. or Genscript, Inc. The genes' DNA sequences are provided below.

Gene Descriptions

Gene gst came from *Schistosoma japonicum*, a parasite commonly called the liver fluke. GST is a relatively small protein with a molecular weight of 26 kilo-Daltons (218 amino acids, 654 nucleotides). gst is highly expressed in *E. coli* and is soluble in the cytoplasm. GST was chosen as a candidate for model optimization because it is a well-studied eukaryotic protein that has a commercially-available assay for quantifying protein yield. Even though wildtype gst is highly expressed in *E. coli*, the model showed that ribosome displacement can be further minimized to improve expression level [93]. The source of wildtype gst used for prediction and optimization came from the pET-41a+ plasmid (Novagen, Inc.). gst from pET-41a+ is identical to that cloned from *Schistosoma japonicum* [92].

pf0132 (GenBank: NP_577861.2) is an alpha-glucosidase from archaeon *Pyrococcus furiosus* DSM 3638 that was characterized by Costantino et al. [87]. *Pyrococcus furiosus* is a hyperthermophile that lives at 100° C. pf0132 was chosen because it belongs to a domain of life (Archaea) different from that of prokaryotic *E. coli*. Furthermore, pf0132 showed high ribosome displacement which can be minimized to increase protein yield. The molecular weight of PF0132 is 55 kilo-Daltons and contains 489 amino acids (1,467 nucleotides).

clju_11880 (GenBank: CLJU_c11880) is an alcohol dehydrogenase that comes from Clostrium *ljungdahlii* DSM 13528. Clostrium *ljungdahlii* is an anaerobic, enteric bacterium. clju_11880 was chosen because it comes from a genome with high AT content compared to the genome of *E. coli*. Wildtype clju_11880 also showed high displacement which could be minimized to increase protein yield. The molecular weight of CLJU_c11880 is 42 kilo-Daltons, and it contains 380 amino acids (1,140 nucleotides).

rt8_0542 is both an endoglucanase (containing the GH9 domain) and exoglucanase (containing the GH48 domain) from an unpublished Caldicellulosiruptor species. Caldicellulosiruptor is a thermophilic, anaerobic, gram-positive bacterium. Although wildtype rt8_0542 has not been successfully expressed in *E. coli*, a codon bias-optimized variant has produced working protein. Both wildtype and codon bias-optimized rt8_0542 were analyzed using the model to determine key differences. rt8_0542 was chosen to gain insight into the dynamics of codon bias optimization and to better compare codon bias optimization to model optimization in silico. The molecular weight of rt8_0542 is 210 kilo-Daltons, and it contains 1,875 amino acids (5,625 nucleotides).

Cloning Genes into pBAD-Myc-His Plasmid

Genes described above, including the start and stop codon, were synthesized and cloned into the pBAD/Myc-His C plasmid (available from Thermo Fisher Scientific, Inc., Catalog Number: V440-01) using GATEWAY cloning technique by either Genewiz, Inc. or GenScript, Inc. Insertion of the gene sequence into the plasmid directly replaced the ATG at the NcoI site, as shown in FIG. 28.

Comparison of Protein Yield Prediction Indices

Multiple mRNA variants of GST were designed and expressed to assess the model's capabilities in predicting protein yields. The rationale for this experiment was to determine a feasible index from the model for protein yield prediction. The bottleneck index (BNI) was the most feasible predictor for protein yield (see above). The bottleneck index is calculated as the function of displacement, aminoacyl-tRNA usage, force, and ribosome wait time. This index identifies clusters of high ribosome wait time and indicates the location of translational bottlenecks on the mRNA.

The BNI's accuracy was confirmed by correlating BNI predictions with GST activity from nine mRNA variants. The codon adaptation index (CAI) was also evaluated in the same manner. CAI using *E. coli* genomic coding sequences as references [100,101] and CAI (HEG) using highly expressed genes as references were both tested. Total Wait Time from the model (see above) was also correlated to GST activity. The resulting correlation of the four indices was compared to assess their prediction accuracy. The nine gst variants were referred to as W, M, VM, 16, 23, 80, 82, 90D, 0D. The first 90 bases of all gst variants were unchanged from the wildtype gene (except for variant M) to normalize protein yield deviations caused by initiation.

Design Rationale and Graphical Analysis of gst Variants gst variant M was "manually" optimized by minimizing displacement throughout the gene. This optimization was done because displacement was initially thought to be the major predictor of protein yield; however, after various predictions, ribosome wait times and translation bottlenecks were found to be better indicators of protein yield. Ribosome wait times and translation bottlenecks are a function of ribosome displacement, aminoacyl-tRNA usage, and force from the ribosome spring. Variant VM is similar to variant M except that the first 90 bases in variant VM are that of the wildtype. Variant 80 was codon bias-optimized using the "one amino acid, one codon" algorithm. A comparison between model-optimized (variant VM), codon bias-optimized (variant 80), and wildtype was published in Vu et al. [92]. Variant 82, like variant 80, was chosen for its high CAI, but interestingly, the phase angle of variant 82 was closer to the species angle, and the displacement was closer to zero throughout the entire gene. One would expect this variant to produce more protein than variant 80. Variant 16 was designed using a random mRNA sequence generator. Variant 16 was chosen because it has a low CAI, but its displacement remained close to zero. Expression of variant 16 was performed to assess whether ribosome displacement was a better predictor of protein yield than codon bias or if Total Wait Time and translation bottlenecks (BNI) might be better predictors. Variant 23 was also designed using a random mRNA generator. Variant 23 was chosen because of its low CAI and its strange polar plot behavior at zero degrees. Variant 90D was designed using the model to have an average phase angle at around 90 degrees; this phase angle is out of the "normal" range for *E. coli*. Therefore, the ribosome is displaced from codon 40 to the stop codon with maximum displacement of around +1 units; this corresponds to a misalignment of half a nucleotide in the +1 reading frame. Variant 0D was designed using the model to have an average phase angle at around 0 degrees; this phase angle is on the boundary but within the "normal" range of *E. coli*. Even though the phase angle is "on the border," the ribosome displacement remains close to zero. Both 90D and 0D variants have the same codon bias as determined by the CAI but different displacement, total number of wait cycles, and BNIs (see Table 4). According to the model's prediction, variant 90D should produce lower protein yield than variant 0D. Polar plots, ribosome displacement plots, ribosome wait time plots, and translation bottleneck plots of gst variants were all generated, as described below.

Wildtype Graphical Plots

Wildtype gst showed an average phase angle of −64 degrees. *E. coli*'s species angle is −23 degrees. Genes that have an average phase angle that deviates from *E. coli*'s species angle exert extra force on the ribosome during translation, which is caused by the compression or extension of the ribosome spring. This extra force can displace the ribosome when aminoacyl-tRNAs with low abundances are used. In the case of wildtype gst, the ribosome is displaced.

The ribosome is displaced from codon 50 to codon 224 The maximum displacement is +0.75 at around codon 160 (ribosome displacement of 0.375 nucleotides towards the +1 reading frame). The ribosome wait time plot shows clustering of high wait times around codons 65 and 200 with a Total Wait Time of 1694 cycles. The clustering leads to bottlenecks at around codon 65 and codon 200 with the maximum bottleneck (BNI of 228) at codon 199.

Variant M Graphical Plots gst variant M was manually optimized to minimize displacement. Variant M showed an average phase angle of −57 degrees. Even though the gene's average phase angle differs from the *E. coli*'s species angle and exerts extra force on the ribosome, displacement is mitigated because aminoacyl-tRNAs with high abundance are used at key codon positions.

However, even after minimizing displacement, the ribosome wait time plot shows clustering of high wait times around codon 65, codon 110, and codon 200; the Total Wait Time is lowered to 1492 cycles down from 1696 cycles in the wildtype. However, because of high wait-time clustering, bottlenecks exists at codons 65, 100, and 200. The maximum bottleneck (BNI of 218) is computed at codon 67

Variant VM Graphical Plots gst variant VM is similar to variant M except that the first 90 bases are directly copied from the gst wildtype. Variant VM showed an average phase angle of −59 degrees.

Ribosome displacement is minimized almost identical to that of variant M. However, even though ribosome displacement is minimized, the ribosome wait time plot shows clusters of high wait times around codon 65, codon 110, and codon 200; the Total Wait Time is lowered to 1494 cycles as compared to wildtype Because of high wait-time clustering, bottlenecks exist at around codon 65, codon 100, and codon 200. The maximum bottleneck (BNI of 218) is at codon 67.

Variant 16 Graphical Plots gst variant 16 was designed using a random mRNA sequence generator. Variant 16 was chosen because it has a low CAI, yet its displacement remained close to zero. Variant 16 was tested to determine whether ribosome displacement is a better indicator of protein yield than codon bias or if Total Wait Time and translation bottlenecks might be better predictors. Variant 16 showed an average phase angle of −43 degrees.

Ribosome displacement was minimized throughout elongation. The ribosome wait time plot shows clustering of high wait times around codon 65 and codon 180; the Total Wait Time is increased to 2012 cycles compared to 1696 cycles in the wildtype. Because of high wait-time clustering, bottlenecks exist at around codon 59 and codon 180. The maximum bottleneck (BNI of 296) is at codon 59.

Variant 23 Graphical Plots gst variant 23 was also designed using a random mRNA sequence generator. Variant 23 was chosen because it has a low CAI and interesting polar plot behavior at zero degrees. Variant 23 showed an average phase angle of −18 degrees.

Ribosome displacement stayed minimized throughout elongation with the exception of codons 80 to 110, in which ribosome displacement decreases to around-0.70. The ribosome wait time plot shows clustering of high wait times around codon 60, codons 90 to 110, and codon 180; the Total Wait Time is increased to 1788 cycles compared to 1696 cycles in the wildtype. Because of high wait-time clustering, bottlenecks exist around codon 60, codon 90, and codon 185. The maximum bottleneck (BNI of 261) is at codon 185.

Variant 80 Graphical Plots gst variant 80 was codon bias-optimized using the "one amino acid one codon" algorithm. Variant 80 showed an average phase angle of −59 degrees.

The ribosome begins being displaced from codon 40 to codon 175. The maximum displacement is +0.50 around codon 85 to 125, which corresponds to an A-site misalignment of 0.25 nucleotides toward the +1 reading frame. The ribosome wait time plot shows clustering of high wait times around codon 3: the Total Wait Time is decreased to 1148 cycles compared to 1696 cycles in the wildtype. Because of high wait-time clustering, bottlenecks exist around codon 2. The maximum bottleneck (BNI of 160) is at codon 2.

Variant 82 Graphical Plots gst variant 82, like variant 80, was chosen because of its high CAI; however, the phase angle of variant 82 was closer to the species angle of *E. coli*, and its displacement was closer to zero throughout the enter gene. One would expect this variant to produce higher protein yield than variant 80. Variant 82 showed an average phase angle of −51 degrees.

The ribosome showed minimal displacement throughout elongation. The ribosome wait time plot shows clustering of high wait times around codon 3; the Total Wait Time is decreased to 1148 cycles compared to 1696 cycles in the wildtype. Because of high wait-time clustering, bottlenecks exist at around codon 2. The maximum bottleneck (BNI of 160) is at codon 2.

Variant 90D Graphical Plots

Using the model, gst variant 90D was designed to have a phase angle at around 90 degrees. Variant 90D showed an average phase angle of −87 degrees.

Because the average phase angle of variant 90D is out of the "normal" phase angle range for *E. coli*, the ribosome is displaced from around codon 40 to codon 224. The ribosome wait time plot shows clustering of very high wait times around codon 110; the Total Wait Time is increased to 1925 cycles compared to 1696 cycles in the wildtype. Because of high wait-time clustering, bottlenecks exist around codon 100. The maximum bottleneck (BNI of 288) is at codon 100.

Variant 0D Graphical Plots

Using the model, gst variant 0D was designed to have a phase angle at around 0 degrees. Variant 0D showed an exact average phase angle of −3 degrees. This phase angle is on the boundary of the "normal" phase angle range of *E. coli*.

Even though the phase angle is "on the border," the ribosome displacement stays close to zero and deviates about 0.5 displacement units. The ribosome wait time plot shows clustering of high wait times around codon 180 and 200; the Total Wait Time is decreased to 1527 cycles compared to 1696 cycles in the wildtype. Bottlenecks exist around codon 185. The maximum bottleneck (BNI of 205) is at codon 185.

Experimental Procedures and Laboratory Results

All gst variants were synthesized and cloned into pBAD/Myc-His inducible plasmid available from Thermo Fisher Scientific, Inc. gst genes were synthesized and cloned by Genewiz, Inc. or GeneScript, Inc. The plasmids containing gene insert were transformed into chemically competent TOP10 *E. coli* cells (available from Thermo Fisher Scientific, Inc.) and expressed at 0.02% w/v (0.2 mg/ml) arabinose for 3 hours. The $P_{bad}$ inducible promoter was used to normalize the transcript levels. One milliliter of induced cells were harvested, pelleted, and lysed with BugBuster and Lysonase (both available from EMD Millipore, Inc.). GST activity was quantified using GST assay kit (E.C. 2.5.1.18) available from Sigma Aldrich, Inc. One unit of GST is defined as the amount of GST enzyme that produces 1 umol of GS-DNB conjugate per minute. GST specific activity was normalized to total protein activity using the Pierce™ BCA Protein Assay Kit available from Thermo Fisher Scientific, Inc. Total protein normalization was performed to standardize for deviations in the number of cells collected. Units for normalized GST activity were defined as units of GST per $A_{562\ nm}$ of total protein where one $A_{562\ nm}$ equals 18 mg of total protein. The calculations for units of normalized GST activity are described in more detail below. Two independent inductions were conducted to test for replicability. Three samples were collected from each induction for a total of six samples assayed. Detailed experimental procedures can be found below. Normalized GST activity of each gst variant and its protein yield prediction indices are shown in Table 4.

GST Protein Quantification

Activity Assay: Cell pellets from induction were re-suspended in 1 ml of EMD Millipore's BugBuster™ Protein Extraction Reagent (Catalog Number: 70584). 3 ul of EMD Millipore's Lysonase™ Bioprocessing Reagent (Catalog Number: 71230) per 1 ml of BugBuster™ was added to each cell re-suspension; Samples were placed on a shaker (55S Single Platform Shaker from Reliable Scientific, Inc.) at medium speed at room temperature for 20 min and subsequently centrifuged at 16,000G at 4° C. for 20 min.

Glutathione S-transferase activity (E.C. 2.5.1.18) was quantified in 96-well microplates using GST assay kit from Sigma Aldrich, Inc. (Catalog Number: CS0410). 10 uL of each cell lysate was aliquoted in three wells as triplicates. 190 uL of assay mixture containing [9.8:1:1] mixture of [Dulbecco's Phosphate Buffered Saline: 100 mM 1-chloro-2,4-dinitrobenzene (CDNB): 200 mM L-glutathione reduced] (all from Sigma-Aldrich, Inc.) was added to each well. GST produces GS-DNB using L-Glutathione and CDNB as substrates. The GST assay kit measures the production of GS-DNB conjugate, which absorbs light at 340 nm. Ten absorbance measurements at 340 nm are made at 30 second intervals using a POLARstar Galaxy microplate reader from BMG LABTECH, Inc. The first measurement was made exactly 1 minute after mixing assay mixture and cell lysate. GST activity is directly proportional to the rate of increase in absorbance at 340 nm per minute ($\Delta A_{340nm}$/minute). Therefore, GST activity was measured as the slope of the ten absorbance measurements with respect to time (in units of $\Delta A_{340nm}$/minute). GST specific activity was calculated using the following formula:

$$\frac{\frac{\Delta A_{340nm}}{min} \cdot V(ml) \cdot dil}{\varepsilon_{mM} \cdot V_{enz}(ml)} = \frac{umol}{ml \cdot min} = \frac{Units\ of\ GST}{ml}$$

One unit of GST is defined as the amount of GST enzyme producing 1 umol of GS-DNB conjugate per minute at 25° C. dil is the dilution factor of original sample: $\varepsilon_{mM}$ is the millimolar extinction coefficient for GS-DNB conjugate at 340 nm; V is the reaction volume; and $V_{enz}$ is the volume of the sample tested. The milli-molar extinction coefficient ($\varepsilon_{mM}$) for GS-DNB conjugate at 340 nm is 9.6 mM$^{-1}$ for a path length of 1 cm. Under the aforementioned assay conditions, dil=1, $\varepsilon_{mM}$=6.04, V (ml)=0.2, and $V_{enz}$ (ml)=0.01.

$$\frac{Units\ of\ GST}{ml}$$

were multiplied by 0.2 ml (cell pellet resuspension volume) to compute the units of GST per cell pellet.

GST specific activity was normalized to total protein using Pierce™ BCA Protein Assay Kit (available from Thermo Fisher Scientific, Inc., Catalog Number: 23225). Total protein normalization was performed to standardize for deviations in the number of cells collected. Total protein content was measured by absorbance of light at 562 nm ($A_{562nm}$) according to the manufacturer's instructions for the microplate procedure. The same microplate reader (POLARstar Galaxy microplate reader) was used, and $A_{562nm}$ measurements were made after 1 hour of incubation at room temperature. Normalized GST activity was computed by dividing GST specific activity with total protein measurements ($A_{562nm}$) for the same cell pellet. Units for normalized GST activity are defined as units of GST per $A_{562nm}$ of total protein where one unit of $A_{562nm}$ equals 18 mg of total protein using the BSA standard curve. All assays were conducted in triplicates and measured within the linear range of the assay.

PF0132 Protein Quantification

SDS-PAGE: Gene pf0132 and variants expressed as insoluble inclusion bodies. Soluble fraction and inclusion body purification were performed using EMD Millipore's BugBuster™ Protein Extraction Reagent (Catalog Number: 70584) and EMD Millipore's Lysonase™ Bioprocessing Reagent (Catalog Number: 71230) according to the manufacturer's instructions following a 4 hour induction at a 0.2% w/v (2 mg/ml) arabinose concentration. Wash and resuspension volumes ranging from 200 uL to 1 ml were used to vary purified protein concentration.

Inclusion body and water-soluble fraction of wildtype and model-optimized pf0132 were visualized on SDS-PAGE gels. Samples were mixed with equal volume of 2× Laemmli Sample Buffer (available from Bio-Rad, Inc., Catalog Number: 1610737) prepared with 5% 2-mercaptoethanol Samples were incubated in boiling water for 5 minutes. 30ul of samples were loaded and run on a NuSep's Tris-Glycine NB 4-20% precast SDS-PAGE gel (Catalog Number. NB10-008) in a Mini-PROTEAN® Tetra Electrophoresis System by Bio-Rad, Inc. PageRuler Prestained Protein Ladder (available from Thermo Fisher Scientific, Inc., Catalog Number: 26616) was used as a protein size standard. The gels were run at 125 V for approximately 2 hours. The completed gel was placed on a shaker at low speed in NuBlu Express Stain according to manufacturer's instruction to visualize protein bands.

CLJU_C11880 Protein Quantification

Activity Assay: Cell pellets from induction were resuspended in 200 ul of EMD Millipore's BugBuster™ Protein Extraction Reagent (Catalog Number: 70584). 3 ul of EMD Millipore's Lysonase™ Bioprocessing Reagent (Catalog Number: 71230) per 1 ml of BugBuster™ were added to each cell resuspension. Samples were placed on a shaker at medium speed at room temperature for 20 minutes and subsequently centrifuged at 16,000G at 4° C. for 20 minutes.

CLJU_cl1880 (alcohol dehydrogenase, ADH) activity levels were quantified using the alcohol dehydrogenase (EC 1.1.1.1) enzymatic assay protocol available from Sigma Aldrich, Inc. [86]. All assay conditions were conducted per manufacturer's instructions with contents reduced tenfold for use on 96-well microplate. ADH converts alcohol to aldehyde, with the concomitant reduction of $NAD^+$ to NADH. The ADH assay measures the reduction $NAD^+$ to NADH; NADH absorbs light at 340 nm. Ten absorbance measurements at 340 nm were made at 30-second intervals using a microplate reader. The first measurement was made exactly 1 minute after combining assay mixture and cell lysate. ADH activity is directly proportional to the rate of increase in absorbance at 340 nm per minute ($\Delta A_{340nm}$/minute). Therefore, ADH activity was measured as the slope of the ten absorbance measurements with respect to time (in units of $\Delta A_{340nm}$/minute). ADH specific activity was calculated using the follow formula:

$$\frac{\frac{\Delta A_{340nm}}{min} \cdot V(\text{ml}) \cdot dil}{\varepsilon_{mM} \cdot V_{enz}(\text{ml})} = \frac{umol}{\text{ml} \cdot \text{min}} = \frac{\text{Units of } ADH}{\text{ml}}$$

One unit of ADH is defined as the amount of ADH enzyme producing 1 umol of NADH per minute at 25° C. dil is the dilution factor of original sample; $\varepsilon_{mM}$ is the milli-molar extinction coefficient for NADH at 340 nm; V is the reaction volume; and $V_{enz}$ is the volume of the sample tested. The milli-molar extinction coefficient ($\varepsilon_{mM}$) for NADH at 340 nm is 6.22 $mM^{-1}$ for a path length of 1 cm. Under the aforementioned assay conditions, dil=1, $\varepsilon_{mM}$=5.47, V (ml) =0.3, and $V_{enz}$ (ml)=0.01.

$$\frac{\text{Units of } ADH}{\text{ml}}$$

were multiplied by 0.2 ml (cell pellet resuspension volume) to compute the units of ADH per cell pellet.

ADH specific activity was normalized to total protein using Pierce™ BCA Protein Assay Kit (available from Thermo Fisher Scientific, Inc., Catalog Number: 23225). Total protein normalization was performed to standardize for deviations in the number of cells collected Total protein content was measured by absorbance of light at 562 nm ($A_{562nm}$) according to the manufacturer's instructions for the microplate procedure; the same microplate reader (POLARstar Galaxy microplate reader) was used. $A_{562nm}$ measurements were made after 1 hour of incubation at room temperature. Normalized ADH activity was computed by dividing ADH specific activity with total protein measurements ($A_{562nm}$) for the same cell pellet. Units of normalized ADH activity are defined as units of ADH per $A_{562nm}$ of total protein where one unit of $A_{562nm}$ equals 18 mg of total protein using the BSA standard curve. All assays were conducted in triplicates and measured within linear range of the assay.

SDS-PAGE

Both wildtype and optimized clju c11880 also expressed as insoluble inclusion bodies. Water-soluble fractions and inclusion body purification were performed using BugBuster™ Protein Extraction Reagent and Lysonase™ Bioprocessing Reagent according to the manufacturer's instructions following a 4 hour induction at a 0.2% w/v (2 mg/ml) arabinose concentration. Wash and resuspension volumes ranging from 200 uL to 400 ul were used to vary purified protein concentration for visualization on SDS-PAGE gel.

Inclusion body, whole cell lysate, and water-soluble fraction of wildtype and model-optimized clju_c11880 were visualized on SDS-PAGE gels. Samples were mixed with equal volume of with 2× Laemmli Sample Buffer (available from Bio-Rad, Inc., Catalog Number: 1610737) prepared with 5% 2-mercaptoethanol. Samples were incubated in boiling water for 5 minutes. 30ul of samples were loaded and ran on a NuSep's Tris-Glycine NB 4-20% precast SDS-PAGE gel (Catalog Number: NB10-008) in a Mini-PROTEAN® Tetra Electrophoresis System by Bio-Rad, Inc. PageRuler Prestained Protein Ladder (available from Thermo Fisher Scientific, Inc., Catalog Number: 26616) was used as a protein size standard. The gels were run at 175 V for approximately 1 hour. The completed gel was placed on a shaker at low speed in NuBlu Express Stain to visualize protein bands.

Correlating GST Activity with Predictive Indices

Normalized GST activity levels were correlated with the following predictive indices for protein yield: CAI using *E. coli* genomic coding sequences, CAI using highly expressed genes (HEG), Total Wait Time, and BNI. For comparison purposes, normalized GST activity and values for the various predictive indices for the corresponding gst variants can be found in Table 4. Correlations were computed by fitting a best-fit line using least-square regression and calculating the resulting r (Pearson correlation coefficient) and r-squared (coefficient of determination) values. BNI had the best correlation followed by Total Wait Time, CAI, and then CAI (HEG). BNI correlated with an r=−0.96 and r-squared=0.92; Total Wait Time correlated with an r=−0.89 and r-squared=0.80; CAI correlated with an r=0.75 and r-squared=0.57; and CAI (HEG) correlated with an r=0.68 and r-squared=0.47.

TABLE 4

Normalized GST activity and protein yield predictive indices for gst variants. Normalized GST activity, CAI, CAI (HEG), Total Wait Time, and BNI values for each gst variant are listed. CAI is the codon adaptation index using *E. coli* genomic coding sequences [94] as reference genes. CAI (HEG) is the codon adaptation index using highly expressed genes from [91] as reference genes. Total Wait Time and bottleneck index (BNI) are protein yield prediction indices from the model. gst variants are sorted from lowest to highest normalized GST activity.

| gst Variants | Normalized GST Activity[1] | CAI | CAI (HEG) | Total Wait Time (Cycles) | BNI[3] |
|---|---|---|---|---|---|
| 16 | 0.413 ± 0.023 | 0.41 | 0.13 | 2012 | 296 |
| 90D | 0.422 ± 0.038 | 0.54 | 0.31 | 1925 | 288 |
| 23 | 0.493 ± 0.029 | 0.44 | 0.20 | 1788 | 261 |
| Wildtype | 0.540 ± 0.033 | 0.58 | 0.34 | 1694 | 228 |
| 0D | 0.555 ± 0.027 | 0.56 | 0.33 | 1527 | 205 |
| 80 | 0.583 ± 0.032 | 0.75 | 0.79 | 1148 | 160[2], 202[3] |
| VM | 0.590 ± 0.014 | 0.61 | 0.37 | 1494 | 218 |
| M | 0.594 ± 0.024 | 0.62 | 0.39 | 1492 | 218 |
| 82 | 0.607 ± 0.037 | 0.78 | 0.80 | 1148 | 160[2], 202[3] |

±indicates one standard deviation.
[1]Normalized GST activity is measured as units of GST per $A_{562\,nm}$ of total protein where one $A_{562\,nm}$ equals 18 mg of total protein; one unit of GST is defined as the amount of GST enzyme producing 1 umol of GS-DNB conjugate per minute.
[2]BNI values before adding wait time value to initiation.
[3]BNI values after adding wait time value to initiation.

In order for BNI to correlate with r-squared=0.92, a ribosome wait time value was adjusted to the beginning of all gene variants by adding 50 wait cycles to the beginning of each gene. This increased ribosome wait time simulates the bottleneck at translation initiation. After adding the wait time values to the beginning of each gene, the BNI of variants 80 and 82 changed from 160 to 202 at the beginning of the gene. The BNI of other variants were not affected. This is because the BNIs of other genes were already greater than 202 and were located at the middle or the end rather than the beginning of the gene. On the other hand, variants 80 and 82 did not have bottlenecks in the middle or end of the gene. In essence, the model over-predicted the protein yield for variants 80 and 82 because bottlenecking at initiation was not taken into account. Adding ribosome wait time value at the beginning of each gene takes into account bottlenecking at initiation and, thus, improves protein yield prediction.

The ordering of normalized GST activity from lowest to highest corresponds better with BNI and Total Wait Time than with CAI and CAI (HEG) indices. gst variant 90D and variant 0D was designed to have the similar CAI (0.54 and 0.56 respectively) and CAI (HEG) (0.31 and 0.33 respectively) but different ribosome displacements. Variant 90D was designed to have higher ribosome displacement while variant 0D has lower displacement. This resulted in a higher BNI and Total Wait Time for variant 90D when compared to 0D (see Table 4). BNI and Total Wait Time predicted that variant 0D will have higher yield compared to 90D. According to CAI and CAI (HEG), the two variants should have similar yield; however, gst variant 0D showed 23% higher yield than variant 90D. This indicated that BNI and Total Wait Time more accurately predict the activity levels of 90D and 0D compared to CAI and CAI (HEG). Variant 23 showed a 17% increase in activity level compared to variant 90D. CAI and CAI (HEG) predicted that the yield of variant 23 is lower than that of variant 90D. Contrastingly, BNI and Total Wait Time predicted that variant 23 produces a higher yield than variant 90D. BNI and Total Wait Time predicted GST activity more accurately. According to CAI and CAI (HEG), variants 80 and 82 should produce a lot more yield compared to variant M and VM. However, measured activity levels showed that variants 80 and 82 produced similar levels to variants M and VM. BNI more accurately predicted the protein yield of variants 80 and 82 compared to variants M and VM given the inclusion of ribosome wait time value at initiation. The Total Wait Time index did not accurately predict the protein yield of variants 80 and 82 versus variants M and VM because it does not take bottlenecks into account.

Comparison of Gene Optimizations

Five protein candidates were chosen and expressed in *E. coli* to assess the model's optimization capabilities and were compared to codon bias optimization. The five candidates were GST, a glutathione S-transferase; PF0132, an alpha-glucosidase; CLJU_c11880, an alcohol dehydrogenase; and Rt8_0542, an endoglucanase and exoglucanase. Model optimizations of gst was performed. Model optimization of gst were compared to that of two codon bias optimization algorithms: 1) the "one amino acid, one codon" method, and 2) the "codon table matching, random guided" method. Optimization of clju_c11880 and pf0132 was performed by minimizing displacement only; this ensures the codon bias remains approximately the same in both wildtype and model-optimized variants. The codon adaptation index (CAI) was used as a measurement of codon bias. The front ends of all variants were unchanged to standardize for deviation in protein yield caused by initiation. The first 51 bases of gst was optimized using Salis's RBS calculator [90]. Changing the front end of a gene using Salis's RBS calculator [90] optimizes translation initiation such that there should not be a bottleneck at initiation. The resulting optimized front end generated by Salis's RBS calculator was used in all gst variants; whereas, the first 90 bases of optimized clju_c11880 and pf0132 used that of their respective wildtypes.

GST, Glutathione-S-Transferase
Gene Optimization and Graphical Analysis gst was optimized by choosing the codons that code for the most abundant tRNA while minimizing force and displacement. This kept the average phase angle of the gene close to the species angle of −23 degrees. gst was also optimized using two codon bias optimization algorithms. "Codon bias-optimized 1" was optimized using the "one amino acid, one codon method" by Optimizer [91]. "Codon bias-optimized 2" was optimized using the "guided random, codon table matching" method by IDTDNA, Inc.'s CodonOpt software. The codon bias optimization algorithms used highly expressed genes as the reference genes. The first 51 bases of gst were optimized using Salis's RBS calculator [90]. Optimizing the front end using Salis's RBS calculator optimizes translation initiation so that there should not be a bottleneck at initiation. The resulting optimized front end generated by Salis's RBS calculator was used in all gst variants.

Polar plot analysis showed that the average phase angle of "codon bias-optimized 2" gst was shifted to −25 degrees from the wildtype phase angle of −61 degrees. The average phase angle of "codon bias-optimized 1" gst was shifted to −36 degrees from the wildtype phase angle of −61 degrees. The model-optimized variant was optimized close to the species angle, so the phase angle stayed close to −21 degrees.

For wildtype gst, the ribosome was displaced from codon 50 to the stop codon. The ribosome displacement plot showed that both codon bias-optimized and model-optimized variants reduce displacement. The model-optimized variant reduced displacement the most.

Wildtype gst showed clustering of high ribosome wait time at around codon 65 and codon 200 and bottlenecks at around codon 65 and codon 198. Ribosome wait time plots showed that both codon bias and model-optimized variants lowered wait times throughout the coding region as compared to wildtype. Translation bottleneck plots showed that all optimization methods lowered bottlenecks throughout the coding region as compared to wildtype. Normalized GST activity and protein yield prediction indices are shown in Table 5.

Experimental Procedures and Results

Wildtype and optimized gst variants were synthesized and cloned into pBAD/Myc-His inducible plasmid available from Thermo Fisher Scientific, Inc. gst genes were synthesized and cloned by Genewiz, Inc. or GeneScript, Inc. The plasmids containing the gene insert of interest were transformed into chemically competent TOP10 E. coli cells (available from Thermo Fisher Scientific, Inc.) and expressed at 0.02% w/v (0.2 mg/ml) arabinose for 3 hours. The $P_{bad}$ inducible promoter was used to normalize for transcript levels. One milliliter of induced cells was harvested, pelleted, and lysed with BugBuster and Lysonase (both available from EMD Millipore, Inc.). GST activity was quantified using GST assay kit (E.C. 2.5.1.18) available from Sigma Aldrich, Inc. Because of increased GST activity, cell lysates were diluted twofold before assaying. One unit of GST is defined as the amount of GST enzyme producing 1 umol of GS-DNB conjugate per minute. GST specific activity was normalized to total protein using Pierce™ BCA Protein Assay Kit available from Thermo Fisher Scientific, Inc. Total protein normalization was performed to standardize for deviations in the number of cells collected. Units for normalized GST activity levels were defined as units of GST per $A_{562nm}$ of total protein where one $A_{562nm}$ equals 18 mg of total protein. Calculations for units of normalized GST activity are described above. Three independent inductions were conducted to test for replicability. From each induction, three samples were collected for a total of nine samples assayed. Detailed experimental procedures are described above.

Normalized GST activity and protein yield prediction indices for each gst variant can be found in Table 5. Model-optimized variants showed an increase of 53% over wildtype, "codon bias-optimized 1" showed a 13% increase over wildtype, and "codon bias-optimized 2" showed a 34% increase over wildtype. All optimizations decreased Total Wait Time and BNI and changed total GC content closer to 50%. CAI and CAI (HEG) indices under-predicted the protein yield of the model-optimized gst variant and over-predicted the protein yield of "codon bias-optimized 1" variant. BNI and Total Wait Time over-predicted the protein yield of "codon bias-optimized 1" variant.

TABLE 6.5

Normalized GST activity of gst variants and their predictive indices. Normalized GST activity, CAI, CAI (HEG), Total Wait Time, and BNI values for wildtype and optimized gst variants are listed. CAI is the codon adaptation index using E. coli genomic coding sequences [94] as reference genes. CAI (HEG) is the codon adaptation index using highly expressed genes from [91] as reference genes. Total Wait Time and BNI (bottleneck index) are protein yield prediction indices from the model. The model-optimized variant showed a 53% increase over wildtype. "Codon bias-optimized 1" showed a 13% increase over wildtype. "Codon bias-optimized 2" showed a 34% increase over wildtype.

| gst Variants | Normalized GST Activity[1] | CAI | CAI (HEG) | Total Wait Time (Cycles) | BNI | GC % |
|---|---|---|---|---|---|---|
| Wildtype | 0.607 ± 0.041 | 0.60 | 0.37 | 1696 | 233 | 39 |
| Model-optimized | 0.927 ± 0.035 | 0.76 | 0.68 | 1019 | 123 | 45 |
| Codon bias-optimized 1 | 0.684 ± 0.050 | 0.84 | 0.97 | 1103 | 139 | 51 |
| Codon bias-optimized 2 | 0.814 ± 0.024 | 0.83 | 0.80 | 1171 | 161 | 49 |

±indicates one standard deviation.
[1]Normalized GST activity is measured as units of GST per $A_{562\ nm}$ of total protein where one $A_{562\ nm}$ equals 18 mg of total protein; one unit of GST is defined as the amount of GST enzyme producing 1 umol of GS-DNB conjugate per minute.

CLJU_c11880. Alcohol Dehydrogenase
Gene Optimization and Graphical Analysis clju_c11880 is an alcohol dehydrogenase (ADH) and was optimized by minimizing displacement only. This was done to ensure that codon bias remained similar between the two variants to better compare the effects of ribosome displacement alone. Minimizing displacement also shifts the average phase angle of the gene (−60 degrees) closer to the species angle of −25 degrees. The bottleneck index (BNI) is lowered from 615 at codon 317 to 322 at codon 93. Wildtype clju_c11880 showed very high wait times from codon 300 to codon 350 Total Wait Time is also lowered from 3905 to 3047 cycles after optimization (see Table 6).

Experimental Procedures and Results

Both wildtype and model-optimized cjlu_c11880 genes were synthesized and cloned into pBAD/Myc-His vectors by Genewiz Inc. The plasmids containing the gene insert of interest were transformed into chemically competent TOP10 E. coli cells (available from Thermo Fisher Scientific, Inc.) and induced at 0.2% w/v (2 mg/ml) arabinose for 4 hours. The $P_{bad}$ inducible promoter was used to normalize for transcript levels. Two milliliters of induced cells were harvested, pelleted, and lysed with BugBuster and Lysonase (both available from EMD Millipore, Inc.). Alcohol dehydrogenase (ADH, E.C. 1.1.1.1) enzymatic assay (protocol available from Sigma Aldrich, Inc.) and SDS-PAGE were conducted on the cell lysates to quantify CLJU_C11880 protein yield. One unit of ADH is defined as the amount of ADH enzyme producing 1 umol of NADH per minute. ADH specific activity was normalized to total protein using the Pierce™ BCA protein assay kit available from Thermo Fisher Scientific, Inc. Total protein normalization was performed to standardize for deviations in the number of cells collected. Units for normalized ADH activity were defined as units of ADH per $A_{562nm}$ of total protein where one $A_{562nm}$ equals 18 mg of total protein. Calculations for units of normalized ADH activity can be found elsewhere herein. Two independent inductions were conducted to test for replicability. From each induction two samples were collected for a total of four samples assayed. Detailed protocols for these procedures are described above.

Wildtype and optimized variants produced protein in both soluble (active) form and insoluble (inactive) inclusion bodies. Both fractions of proteins were quantified to compare production between the wildtype and optimized cjlu_c11880. The enzymatic assay results are shown in Table 6. A 44% increase in the activity of the optimized variant was measured.

TABLE 6 clju_c11880 variants and their protein yield prediction indices. Normalized ADH activity, CAI, CAI (HEG), Total Wait Time, and BNI values for wildtype and model-optimized clju_c11880 are listed. CAI is the codon adaptation index using E. coli genomic coding sequences [94] as reference genes. CAI (HEG) is the codon adaptation index using highly expressed genes from [91] as reference genes. Total Wait Time and BNI (bottleneck index) are protein yield prediction indices from the model. Model-optimized variant yielded 44% more activity than wildtype.

| clju_c11880 Variants | Normalized ADH Activity[1] | CAI | CAI (HEG) | Total Wait Time (Cycles) | BNI | GC % |
|---|---|---|---|---|---|---|
| Wildtype | 0.025 ± 0.004 | 0.53 | 0.25 | 3905 | 615 | 30 |
| Model-optimized | 0.036 ± 0.006 | 0.57 | 0.29 | 3047 | 322 | 40 |

±indicates one standard deviation.
[1]Normalized ADH activity is measured as units of ADH per $A_{562\,nm}$ of total protein where one $A_{562\,nm}$ equals 18 mg of total protein; one unit of ADH is defined as the amount of ADH enzyme producing 1 umol of NADH per minute.

CLJU_cl1880 was also produced in insoluble inclusion body form. Inclusion bodies were purified and quantified using SDS-PAGE. A negative variant, a transformed plasmid which does not contain the clju_c11880 gene insert, was also expressed along with clju_c11880 variants and visualized on an SDS-PAGE gel. A gel comparing the production of CLJU_c11880 across variants was prepared. Samples were from the whole cell lysate, soluble fraction of active enzyme, and insoluble fraction of inclusion bodies. From this comparison, there was a marked decrease in the production of inclusion bodies in the optimized clju_c11880 variant as indicated by black arrows. The lack of inclusion body production in the negative variant (the no-gene insert plasmid) and the estimated size of ~40 kDa for the protein bands (marked by red and black arrows) indicated that these bands are presumed PF0132. Alpha-Glucosidase Gene Optimization and Graphical Analysis pf0132 was also optimized based on minimizing displacement only. This was done to verify whether minimizing displacement increases protein yield. Minimizing displacement changes the phase angle of the optimized variant to −44 degrees. Optimizing pf0132 also decreased Total Wait Time and lowered bottleneck effects (see Table 7).

TABLE 7 pf0132 variants and their protein yield prediction indices. CAI, CAI (HEG), Total Wait Time, and BNI values for pf0132 variants are listed. CAI is the codon adaptation index using E. coli genomic coding sequences [94] as reference genes. CAI (HEG) is the codon adaptation index using highly expressed genes from [91] as reference genes. Total Wait Time and bottleneck index (BNI) are protein yield prediction indices from the model. GC % is percent of total GC content.

| pf0132 Variants | CAI | CAI (HEG) | Total Wait Time (Cycles) | BNI | GC % |
|---|---|---|---|---|---|
| Wildtype | 0.48 | 0.25 | 4044 | 282 | 44 |
| Model-optimized | 0.634 | 0.3 | 3159 | 222 | 48 |

Experimental Procedures and Results

The wildtype pf0732 was cloned from the *Pyrococcus furiosus* genome [87]. The optimized pf0132 gene was synthesized by Genscript, Inc.. Both wildtype and optimized pf0132 were cloned into pBAD-Myc-His plasmids (available from Thermo Fisher Scientific, Inc.) for protein production in TOP10 E. coli strain (available from Thermo Fisher Scientific, Inc.) with a final arabinose concentration of 0.2% w/v (2 mg/ml) for 4 hours. The $P_{bad}$ inducible promoter was used to normalize for transcript levels One milliliter of induced cells was harvested, pelleted, and lysed with Bugbuster and Lysonase (both available from EMD Millipore, Inc.). The resulting lysate was used for assaying and SDS-PAGE. Detailed protocols for these procedures are described elsewhere herein.

pf0132 and its optimized variant produced insoluble inclusion bodies with no enzymatic activity. Therefore, the quantity of (inactive) protein produced was measured with SDS-PAGE gel. Densitometer analysis of SDS-PAGE showed a 210% increase in density of the bands (at 55 kD and 40 kD) in optimized PF0132 versus the bands (55 kD. 32 kD) in wildtype PF0132. This implies a substantial improvement in the production of PF0132 protein compared to the wildtype, although the optimized gene was produced as inclusion body form. Protein bands were identified as PF0132 using MALDI-TOF/TOF and LC-ESI-MS/MS mass spectrometry.

Rt8_0542

Gene Optimization and Graphical Analysis

Wildtype and codon bias-optimized rt8_0542 was analyzed using the model to determine the dynamics of codon bias optimization when compared to the wildtype gene. Codon bias optimization was performed using the "guided random, codon table matching" method by IDTDNA, Inc.'s CodonOpt software. Wildtype rt8_0542 has not been successfully produced in E. coli while codon bias-optimized rt8_0542 was successfully produced as both water soluble protein and inclusion bodies. Model-optimized rt8_0542 is also presented as a reference for comparison between wildtype and codon bias optimization; however, in vivo expression of this variant has not been performed. Both global and local GC contents were computed for all variants. Local GC content plots were computed using [99] with a window size of 50. A summary of all protein yield prediction indices for the three variants are tabulated in Table 9.

The phase angle of wildtype is −90 degrees in the beginning of the gene and gradually shifts to −10 degrees in the latter half of the sequence around codon 600. A shift in local GC content of the wildtype gene from 40 to 50% GC content also occurs at a similar spot at nucleotide 2000. Because the phase angle begins at the "wrong" angle (−90 degrees), the ribosome was displaced 1.5 displacement units downstream (corresponding to a misalignment of ¾ nucleotide towards the +1 reading frame) at around codon 400 when translating the wildtype gene. The ribosome wait time plot of the wildtype rt8_0542 showed clustering of high ribosome wait times (70 to 129 cycles) around codons 400 through 500. Normal ribosome wait times for endogenous E. coli genes are around 5 to 20 cycles per codon. This leads to bottlenecks at around codon 400 through 500. The maximum ribosome wait time is 129 cycles at codon 476. Codon 476 codes for the isoleucine rare codon ATA. According to the model, the ribosomes are unlikely to translate past codon 476 due to high ribosome displacement and very high ribosome wait time. Wildtype variant showed a BNI of 362 and Total Wait Time of 15,053 cycles, which is higher than both model-optimized and codon bias-optimized variants (see Table 9).

The codon bias-optimized variant showed an average phase angle of −24 degrees, which is very close to the species angle. This codon bias optimization was fortuitous because the "guided random, codon table matching" optimization method results in random average phase angles which could be further away from the species angle. Because the phase angle of the gene is near the species angle throughout the coding region, the local GC content also remained around 50%; whereas, the global GC content is 51%. The displacement plot of the codon bias-optimized variant showed reduced displacement when compared to the wildtype variant. Ribosome wait times were lowered to less than 20 cycles per codon, and bottlenecks were lowered throughout the entire coding region compared to wildtype. Codon bias-optimized variant showed a BNI of 218 and Total Wait Time of 11,511 cycles, which is substantially lower than the wildtype variant (see Table 9).

The model-optimized variant showed an average phase angle of −25 degrees, which is very close to the species angle. Both global GC content (see Table 9) and local GC content remained near 50%. The displacement plot of the model-optimized variant showed minimal displacement that is lower than both wildtype and codon bias-optimized variants. Ribosome wait times were lowered to less than 20 cycles per codon, and bottlenecks were lowered throughout the entire coding region compared to the wildtype. The model-optimized variant showed a BNI of 152 and Total Wait Time of 9161 cycles, which is lower than both codon bias-optimized and wildtype variants (see Table 9).

TABLE 9 rt8_0542 variants and their protein yield prediction indices. CAI, CAI (HEG), Total Wait Time, and BNI values for rt8_0542 variants are listed. CAI is the codon adaptation index using E. coli genomic coding sequences [94] as reference genes. CAI (HEG) is the codon adaptation index using highly expressed genes from [91] as reference genes. Total Wait Time and bottleneck index (BNI) are protein yield prediction indices from the model. GC % is percent of total GC content.

| rt8_0542 Variants | CAI | CAI (HEG) | Total Wait Time (Cycles) | BNI | GC % |
|---|---|---|---|---|---|
| Wildtype | 0.54 | 0.29 | 15053 | 362 | 47% |
| Model-optimized | 0.69 | 0.58 | 9161 | 152 | 50% |
| Codon bias-optimized | 0.71 | 0.51 | 11511 | 218 | 51% |

Experimental Procedures and Results

Laboratory experiments were conducted by Jonathan Conway in Dr. Robert Kelly's lab and are included herein with permission. Wildtype rt8_0542 has not been successfully expressed in E. coli; however, the codon bias-optimized variant was successfully expressed as soluble and insoluble fractions. Codon bias-optimized rt8_0542 was overexpressed using the T7 promoter (pET45 plasmid) in Arctic Express DE3 RIL E. coli strain at 13° C. Arctic Express DE3 RIL cells contain chaperones to assist in protein folding and to prevent or reduce inclusion body formation. The soluble portion of codon bias-optimized rt8_0542 was purified using his-tagged purification (Ni-NTA column) and visualized on an SDS-PAGE gel Comparison of Protein Yield Prediction Indices-BNI versus CAI In order to compare the effectiveness of the standard codon adaptation index (CAI) versus the new bottleneck index (BNI) created with the model, the correlation between the indices and normalized GST activities were compared. BNI scored the best correlation with normalized GST activity levels with an r of −0.96 and r-squared of 0.92. Total Wait Time scored the second best correlation with an r of −0.89 and r-squared of 0.80 BNI and Total Wait Time correlated better with normalized GST activity levels than codon bias indices CAI and CAI (HEG). CAI correlated with an r of 0.75 and r-squared of 0.57 while CAI (HEG) scored an r of 0.68 and r-squared of 0.47. For reference, an r above 0.5 indicates that there is a correlation, and an r above 0.8 indicates a very high correlation.

Correlation between BNI and CAI yielded an r of 0.59. This indicates that BNI correlates with CAI because both intrinsically measure tRNA abundance usage. BNI uses actual tRNA abundance measurements from Dong et al. [89] while CAI uses genomic codon frequency as references. The two indices use two different reference sources to predict protein yield, yet both showed correlation with each other and with protein yield. This indicates that genomic codon frequency intrinsically measures tRNA abundance usage. However, unlike CAI and CAI (HEG), which only measure tRNA abundance usage, BNI also accounts for ribosome displacement, force, and clustering of high ribosome wait times (bottlenecks). BNI does not take bottlenecks at initiation or termination into account; however, ribosome wait time values can be added to increase bottlenecks at either location.

Total Wait Time did not score nearly as well as BNI because two genes can have the same Total Wait Time but different "slow" translation clustering sites which result in bottlenecks. The mRNA is concurrently translated into protein by multiple ribosomes; therefore, multiple "slow" translation regions clustered in local proximity are more detrimental to yield than impeding regions distributed across the gene. Total Wait Time does not consider bottlenecks within the codon region, initiation, or termination.

Both CAI and CAI (HEG) correlated similarly according to r and r-square values. However, the correlation was less than BNI and Total Wait Time. This is because CAI and CAI (HEG) only account for codon bias and do not consider the "ordering" of those codons within the gene Two genes can have similar codon bias but different ribosome displacement and translation bottlenecks due to the ordering of codons. Unlike CAI and CAI (HEG), BNI and Total Wait Time consider the actual sequence of codons as it is translated in vivo to consider how that order of codons affects ribosome displacement, force, translation bottlenecks (only for BNI, not Total Wait Time), as well as aminoacyl-tRNA usage.

gst Optimization

All optimized variants shift the phase angle from −61 degrees (that of the wildtype gene) closer to E. coli's species angle of −25 degrees, which minimizes displacement. All optimized variants shifted the GC content of the genes closer to 50%, which matches the GC content of the *E. coli* genome. Both codon bias-optimized and model-optimized variants minimize ribosome wait and bottlenecking effects; however, the model-optimized variant minimizes bottlenecks better than codon bias-optimized variants (see Table 6.5).

All three optimized variants produced an increase in protein yield over the wildtype genes. Model-optimized variants produced the highest increase from the wildtype (53% improvement). The "codon bias-optimized 2" variant using the "guided random, codon table matching" method produced the next highest increase in yield (34% improvement). "Codon bias-optimized 1" variant using the "one amino acid, one codon" method produced the smallest increase in yield (13% improvement). Both codon bias optimization and model optimization did not show "substantial" gain (as observed in [105,106,107]) in protein yield compared to wildtype gst because wildtype gst is already highly expressed in *E. coli*. Optimization of gst for translation elongation has probably hit the upper limit for increasing protein yield.

A probable reason why the "one amino acid, one codon" method did not show a larger increase in yield is because of aminoacyl-tRNA depletion. The "one amino acid, one codon" method uses only one tRNA species per amino acid rather than spreading the tRNA usage as implemented in the "guided random, codon table matching" method. Optimization using the "one amino acid, one codon" method leads to competition between heterologous protein production and endogenous protein production for usage of available aminoacyl-tRNA. The competition depletes available aminoacyl-tRNA; therefore, protein yield suffers. These observations were explained in Welch et al. [102], Dittmar et al. [103], Elf et al. [104], and Menzella et al. [109]. CAI, CAI (HEG), BNI, and Total Wait Time over-predicted the protein yield of the "codon bias-optimized 1" variant which used the "one amino acid, one codon" optimization method. This is because CAI, CAI (HEG), BNI, and Total Wait Time assume unlimited availability of aminoacyl-tRNA; however, availability of aminoacyl-tRNA is limited and can become depleted if both endogenous protein production and heterologous protein production compete for the same tRNA species. In addition, CAI and CAI (HEG) under-predicted the protein yield of model-optimized variant because CAI and CAI (HEG) do not take translation bottlenecks into account.

clju_c11880 Optimization clju_c11880, an alcohol dehydrogenase (ADH), was optimized by minimizing displacement only. This was done intentionally to assess whether minimizing displacement alone will increase protein yield. Optimizing by minimizing displacement also ensured that the codon bias was similar in both variant. Optimized clju_c11880 showed increased enzymatic activity by 44% and decreased inclusion body production when compared to the wildtype.

The decrease in inclusion body production could be caused by the ribosome choosing the correct aminoacyl-tRNA due to reduction of displacement from codon 270 to 380. Picking the wrong aminoacyl-tRNA and incorporating the wrong amino acid can cause misfolding and production of inclusion bodies [110,111]. Wildtype clju_c11880 also showed very high ribosome wait times from codon 300 to 350 leading to bottlenecks around the same position. Optimizing clju_c11880 reduced ribosome wait times and bottlenecks at the same positions. The ribosome may have stalled due to high ribosome wait times around codon 300 to 350. A stalled ribosome will dissociate and produce partially-completed CLJU_C11880 which may not fold correctly to form active enzymes. These partially produced polypeptides can form inclusion bodies [111] that are probably the source of the two smaller bands around 35 kDA in the inclusion body fractions on the SDS-PAGE. The intensity of those two smaller bands is greatly reduced in the optimized variant, suggesting a reduction in inclusion body production. Reduction of ribosome wait times in the optimized variant may have reduced ribosome stalling and dissociations. Reduction in ribosome stalling and disassociation could have caused the reduction of inclusion body production as observed in the two smaller bands of the optimized variant. These aforementioned postulates and observations suggest that optimization of genes using the model's wait time parameters may allow for improved protein folding and, therefore, reduce or eliminate inclusion body production; this postulate was also suggested by Pechmann et al. [97] and Li et al. [98] and was demonstrated by Siller et al. [96] in vivo by decreasing ribosome translation rates.

pf0132 Optimization pf0132 was optimized by minimizing displacement only. This was done to see whether minimizing displacement would increase protein yield. pf0132 was only produced in inclusion body form. Optimized pf0132 showed increased inclusion body production when compared to the wildtype. pf0132 was cloned from an extremophile *Pyrococcus furiosus* that lives at 100° C. PF0132 was evolutionarily designed to fold at a much higher temperature than 37° C., the temperature at which *E. coli* expressed pf0132 in these experiments. Thermophile proteins folded at mesophilic temperature tend to form inclusion bodies because of improper folding [112, 113].

rt8_0542 Optimization

Model analysis showed the potential cause of unsuccessful expression of wildtype rt8_0542 in *E. coli*. An "incorrect" phase angle led to a displaced ribosome which increased ribosome wait times and bottlenecks around codons 400 through 500. The maximum ribosome wait time is 129 cycles at codon 476. Codon 476 codes for the isoleucine rare codon ATA. According to the model, the ribosomes are unlikely to translate past codon 476 due to high ribosome displacement and very high ribosome wait time. This increase in ribosome wait time may be substantial enough (compared to endogenous genes and prfB) for ribosomes to disassociate and stop translating. Alternatively, the ribosome could have potentially frameshifted due to high ribosome displacement of +1.5 units (misalignment of ¾ nucleotides towards the +1 reading frame) and encountered a stop codon in the new reading frame. For comparison purposes, endogenous genes showed ribosome wait times of 5-20 cycles while prfB showed a ribosome wait time of 147 cycles at the frameshift site. Contrastingly, model analysis showed the underlying factors that lead to successful expression of codon bias-optimized variant in *E. coli*. The phase angle of codon bias-optimized variant followed closely to the species angle throughout the coding region; this was "random luck" due to the fact that codon bias optimization (using the "guided random, codon table matching" method) is a stochastic process that does not always closely follow the species angle. Remaining close to the species angle will result in minimal compression or extension of the "spring", which also minimizes displacement. Codon bias optimization reduced ribosome displacement, ribosome wait times, and bottlenecks. Model optimization of rt8_0542 was also included as a reference for in silico comparison to codon bias optimization and wildtype variants. Optimizing rt8_0542 using the model led to a reduction in ribosome displacement, ribosome wait time, and translation bottlenecks. These reductions surpassed that of codon bias optimization.

Conclusions

An index for determining yield was developed based on expression level of multiple mRNA variants of gst. The index is named the bottleneck index (BNI), which measures the clustering of high ribosome wait times during the translation of genes. The development of this index was based on principle of "ribosome traffic jams" and the "ribosome footprint". Total ribosome wait time can also be used as measure of translation efficiency. In comparing these new metrics to measured protein yield, BNI correlated with an r-square of 0.92 while Total Wait Time correlated with an r-squared of 0.80. On the other hand, CAI and CAI (HEG) scored an r-square of 0.57 and 0.47 respectively. This indicated that BNI and Total Wait Time may be a better index for predicting yield, however, BNI and Total Wait Time need to be further tested with a larger dataset to more extensively compare them to CAI's prediction. BNI does not account for bottlenecks at initiation or termination, but values can manually be added at those locations to increase prediction accuracy. BNI may also over-predict protein yield, especially in the case of "one amino acid, one codon" codon bias optimization. This is because BNI assumes unlimited aminoacyl-tRNA availability.

Genes optimized using the model showed increased protein levels when compared to codon bias-optimized variants and wildtype variants. Model-optimized gst showed a 53% increase over wildtype, "codon bias-optimized 2" showed a 34% increase of wildtype, and "codon bias-optimized 1" showed a 13% increase over wildtype. Model-optimized clju_c11880 showed a 44% increase in activity and reduction in inclusion body formation compared to wildtype; this indicated that the model has the potential to reduce or eliminate inclusion bodies by changing ribosome wait time parameters. Model-optimized pf0132 showed an increase in protein production of 200% using densitometer analysis. Unfortunately, both wildtype and optimized variants were only produced as inclusion bodies. Wildtype, model-optimized, and codon bias-optimized variants produced inclusion bodies and minor water soluble fractions. Differences in protein level between the variants were hard to discern from the preliminary data, and the results are in-conclusive. Further laboratory experiments are required. Analysis of wildtype rt8_0542 showed that the first 500 codons were detrimental to protein yield due to high ribosome wait times and bottlenecks. The model suggested that the ribosomes may have dissociated from the mRNA between codon 400 and 500; alternatively, the ribosomes could have potentially frameshifted due to high ribosome displacement of +1.5 units (displacement of ¾ nucleotides towards the +1 reading frame) and encountered a stop codon in the new reading frame. Conversely, codon bias optimization lowered ribosome wait times and bottlenecks which allowed the ribosomes to translate the gene more efficiently. The model-optimized variant showed greater reductions in ribosome displacement, Total Wait Time, and translation bottlenecks compared to codon bias-optimized variant.

As shown through polar plots, codon bias optimization changed the average phase angle of the wildtype genes into the "working" range for E. coli's phase angle. The "one amino acid, one codon" codon bias optimization method (using highly expressed genes as reference) always changed the average phase angle of a gene near −45 degrees. This is because the average phase angle of highly expressed genes is near −45 degrees. The "guided random, codon table matching" codon bias optimization method "randomly" changes the average phase angle of the gene with every optimization because it is a stochastic algorithm (see the phase angle of codon bias-optimized rt8_0542, and gst variants), however, the average phase angle still remains within the "working" range of E. coli's phase angle. Both methods of codon bias optimization miss the species angle (although "codon table matching, guided random" method can by chance "hit" the species angle) resulting in slight displacement of the ribosome. This slight displacement accumulates for very long genes and increases ribosome wait time and bottlenecks. The model optimizes a gene's phase angle using the species angle which results in an average phase angle that is close to the species angle. Therefore, ribosome displacement is minimized more so than with codon bias optimization throughout the coding region. It should be noted that changing the phase angle of the gene (phase angle is related to the binding patterns of the 16S rRNA exposed tail and mRNA) also changes the global and local GC content of the gene. This observation is shown in the optimization example rt8_0542. Therefore, it is contended that GC content is related to the nucleotide composition of the 16S rRNA 3' exposed tail.

The experiment results showed that reducing ribosome displacement, ribosome wait times, and translation bottlenecks usually increased total protein yield. In the case of the CLJU_c11880 optimization, lowering displacement, ribosome wait times, and bottlenecks also reduced inclusion body production. The experimental results also showed that optimization using the model's translation bottleneck principle showed greater improvements in protein yield than codon bias optimization. This is because codon bias optimization does not consider the "ordering" of codons which affects the location of 16S rRNA tail:mRNA bindings relative to the P-site. The distance of the 16S rRNA tail:mRNA bindings relative to the P-site is calculated using the "phase angle". An unfavorable binding (a phase angle that differs from the species angle) compresses or extends the spring which exerts a force on the ribosome. Therefore, this extra force could lead to a displaced ribosome. A displaced ribosome increases the ribosome wait times which can result in translation bottlenecks and, therefore, decrease protein yield.

Experimental results also showed that BNI was a better predictor of protein yield than CAI and CAI (HEG). This is because CAI and CAI (HEG) only consider codon bias rather than the "ordering" of those codons in the gene. Two genes can have similar codon bias but different ribosome displacement and translation bottlenecks due to the "ordering" of codons on the gene as explained in the previous paragraph. Unlike CAI and CAI (HEG), BNI takes aminoacyl-tRNA usage into account as well as the "ordering" of codons, which affects the force exerted on the ribosome, ribosome displacement, and translation bottlenecks.

Based on the results observed in this chapter and the literature published by Vu et al. [93], Li et al. [98], Welch et al [102], Allert et al. [114], Kudla et al. [115], and Tinoco et al. [116] it is contended that the determinants of protein yield from translation elongation are not just codon bias, but, rather, the convolution between aminoacyl-tRNA usage and additional effects involving the interaction between the 16S rRNA 3' terminal end and the mRNA, which may lead to a displaced ribosome and, therefore, increased ribosome wait times, bottlenecks, or frameshifts.

Improvements to the current experimental work should consider case studies including: 1) a comparing of codon bias optimization versus model optimization for very long genes, 2) designing a synthetic +1 or −1 frameshift using the model's principles and verifying the frameshift in. vivo, 3) optimizing and expressing genes that showed poor translation even when codon bias-optimized [20,22,23], 4) conducting ribosome profiling experiments to determine the accuracy of the model's predicted ribosome wait times and bottlenecks.

Example 4

Translation Model and Free Energy Signal

Free Energy Signal. It has been recognized for some time that in bacterial translation the 3' terminal nucleotides of the 16S rRNA ("exposed tail" of about 13 nucleotides) continuously interact with the mRNA sequence [6,9, 10, 11, 14, 15]. These interactions involve Watson-Crick base pairing where the free energy of the hybridization between the 16S rRNA tail and mRNA can be calculated. FIG. 21 illustrates the average signal that is obtained by calculating hybridization energy at every nucleotide of 200 non-frame-shifting *E. coli* endogenous genes [9]. The most prominent binding energy is at the initiation site, but after that there is a periodic (sinusoidal-like) binding signal (negative free energy indicates binding) that corresponds to "in-frame" ribosome translocation [9,10, 11]. When heterologous genes translate without being adapted to the host, this signal is disrupted, which we predict is due to binding misalignments and it becomes more likely that the yield suffers. The mathematics of the model were previously described in [9,10, 11,17,18].

This signal inspired a novel mechanistic model of the process that helps to elucidate frameshifts and to predict and optimize protein yield using second-order energetic interactions between the 16S rRNA 3' terminal "exposed tail" and the mRNA. The model's predictive and optimization power was compared to that of simply using codon bias manipulation and was tested in vivo.

The "Spring" Model. As the ribosome translocates along the mRNA the 16S rRNA 3' terminal end interacts with bases upstream of the ribosome [6,15] (FIG. 22). If that binding energy is sufficiently large and is on the "wrong" side of favoring normal in-frame binding, it may exert extra force on the ribosome and displace it. In the extreme case, a frameshift may occur. We model this "spring-like" reaction force using a sinusoid. For example, in the +1 programmed frameshifting gene prfB (FIG. 22), the aSD of the 16S tail binds to the SD-like sequences 3 bases (UAU in the figure) upstream from the P site resulting in −9.5 kcal/mol of binding energy. This binding is too close to the P site and compresses the distance between the tail and the ribosome. It behaves like a compressed spring, which upon relaxation displaces the ribosome to minimal energy ¾ of a base downstream into the +1 reading frame. The displaced ribosome then picks up the aa-tRNA in the +1 frame. This leads to a one base frameshift after which the new "in-frame" is maintained [9, 10, 18]. In contrast, the SD in the −1 frameshifting gene of dnaX is 10 bases away from the P site [14]. This binding extends the "spring" and displaces the ribosome upstream to produce a "partial" frameshift (between reading frames; producing both τ and γ subunits). We postulate that a "relaxed spring" state occurs when the "optimal" spacing between the SD and start codon is 8 bases [20]. FIG. 23 shows the *E. coli* 16S aSD during in-frame translation of lacZ. The binding energies around that site range from zero to −1 kcal/mol. Because the aSD is bound 8 nucleotides away from the P site, the "spring" is in its "relaxed" state. While slight misalignments between the zero reading frame and A site are possible (and this can affect the yield), there is not enough "spring force" to cause a frameshift.

We model the compression or extension of the "spring" as a change in the "phase" of the free energy sinusoidal signal [10,18] (FIG. 22 and FIG. 23). In the case of a compressed spring (prfB), the phase angle changes 230 degrees at the codon 26 stop [9,18]. In our model, we defined the perfectly relaxed "spring" to have a phase angle of −25 degrees. This is the average phase angle of all non-hypothetical, non-putative, and non-pseudo "long" endogenous genes (1000+ bp) in *E. coli*. We chose to use the phase angle of long genes because we believe that long genes require almost perfect alignment to translate full-length mRNA without errors, i.e. errors can accumulate for very long genes. Therefore the "spring" needs to be close to "relaxed" throughout translation elongation. We define this phase angle as the "species angle".

Ribosome displacement is cumulative and does not reset after translocation. The more the ribosome is displaced, the longer it takes to choose between the two aa-tRNAs of the two reading frames. aa-tRNA abundance of codons in the two reading frames has a major impact on the ribosome wait time. The aa-tRNA abundance translates into tRNA arrival time in our model. When explicit tRNA abundance is not known, we use the codon distribution of the host organism [12]. After the ribosome has "chosen" the next aa-tRNA, it translocates three bases downstream. In our model, one displacement unit is a misalignment of half a nucleotide. Two displacement units is a misalignment of a full nucleotide or a reading frameshift. Effective analysis tools to determine yield are polar, ribosome displacement, and ribosome wait time plots.

Results

Predicting Yield. Expected yield is proportional to the rate at which ribosomes initiate translation and the rate that ribosomes finish translating the mRNA [1]. Our model predicts the ribosome wait time at each codon by calculating the number of cycles it takes to load the next aa-tRNA. The number of "cycles" at each codon is computed as a function of force from the "spring," ribosome displacement magnitude, and tRNA abundance We use the the total cycle count as an internal index for measuring protein yield. However, since the overall goal is to minimize displacement throughout the coding region, we will use total displacement change between wildtype and optimized gene to illustrate optimization extent. Total displacement (TD) is the sum of the displacement in absolute value at each codon throughout the coding region.

While the "total cycle" is a good "global" predictor, a "local" index predictor may be a better estimator of yield. Because mRNA is translated into protein by multiple ribosomes and not just one ribosome at a time, multiple "slow" translation regions clustered together in local proximity are more detrimental to yield than multiple slow regions distributed evenly across the gene. Two genes can have the same total wait cycle but different "slow" translation clustering. This is referred to as the "translation bottleneck" or "ribosome traffic jam principle." To compute the local translation bottleneck index, a "summing" sliding window of size N codons was used (e.g., where N is 20 codons), otherwise known as an integrator. The wait "cycles" were summed within this window and plotted on a plot called the "translation bottleneck plot." The window was then slid downstream one codon, the sums were recomputed and then plotted as the next value on the plot. The "peak" or the maximum sum in the translation bottleneck plot was used as the yield predictor.

Another estimator of yield was termed "the protein translation simulation" and measured the amount of ribosomes that finish translation within a given amount of time. Time in our model was measured in terms of cycles. A "ribosome profile" simulation was created based on wait cycles at each codon. The simulation simulated the ribosomes initiating, translating, and dissociating from the mRNA. The number of ribosomes that finished translating was another "yield index" predictor.

Optimizing Protein Yield. As used herein, the terms "tRNA abundance" and "aminoacyl-tRNA (aa-tRNA or charged-tRNA) abundance" are used interchangeably, tRNA can have an amino acid attached (aa-tRNA) or not have an amino acid attached (uncharged-tRNA). The ribosome uses only aa-tRNA to produce protein, not uncharged-tRNA. However, quantitative data on aa-tRNA is sometimes hard to gather and thus one can infer the relative amount of aa-tRNA by total tRNA concentration (charged plus uncharged tRNA) through publications or codon usage frequency from the genome.

We postulate that if we keep the displacement of a gene close to zero and maximize tRNA arrival time by using the most abundant aa-tRNA, we can decrease ribosome wait time and increase protein yield. A displacement close to zero ensures that the A site is aligned close to the zero reading frame. This can be accomplished by choosing the codon that codes for the most abundant aa-tRNA while keeping the phase angle of the gene close to the "species angle." This results in minimal "spring" compression or extension during translocation. Gene designs, incorporating these concepts, are made by changing the genetic sequence using synonymous codons while conserving the amino acid sequence. We believe the model excels at optimizing very long genes, because it minimizes error accumulated by optimizing on "species angle" rather than codon bias. Conversely, genes can be altered to make protein production "less optimal". A decrease in protein yield, with potential applications in pathway optimization and production of "toxic" protein, can be accomplished by keeping displacement further away from 0 but between −1 and +1 to avoid possible frameshifts. This increases the ribosome wait time at each codon.

This method is feasible at low mRNA transcript levels when the charged-tRNA abundance pool is not taxed and depleted. However, at high mRNA transcript levels it is best to spread the workload between many different tRNA (coding for the same amino acid) rather than using one single tRNA or a single set of tRNA. This relates to the "recharge" rates of tRNA from uncharge to charge [4, 21, 22]. One still needs to stay close to the species angle while spreading the workload across multiple tRNA to avoid displacing the ribosome.

In vivo Experiments. To verify the model's prediction and optimization, we optimized and expressed in E. coli three model genes and multiple mRNA variants coding for GST (26 kDa Glutathion S-Transferase from Schistosoma japonicum, found in pET-41a (+) plasmid; Novagen, Inc.) Protein yield of optimized genes showed increase from wildtype levels. Due to space limitations, we only illustrate optimization results of gst and adh (alcohol dehydrogenase, CLJU_C11880, from Clostridium ljungdahlii DSM 13528). The first 90 bases of all variants were the same as the first 90 bases of the wildtype. This was done to eliminate variations in yield due to translation initiation [1,5,7]. Genes were cloned into pBAD inducible plasmids (Invitrogen, Inc.) and expressed in E. coli. Total protein was quantified by BCA assay and used for normalization of activity; total protein units were measured in absorbance at 562 nm. CAI calculation and optimization were done using the published method [19].

gst was optimized based on the displacement (model-optimized), and codon bias (CAI-optimized); see FIG. 24. All gst variants were cloned into the pBAD inducible plasmid, expressed in E. coli at 0.02% w/v arabinose for 2 hours, and activity levels assayed. GST activity was measured using E.C. 2.5.1.18 assay. Normalized GST yield was quantified in units of $\Delta ABS_{340nm}$/min per total protein. Three independent inductions were conducted to test for replicability. From each induction three samples were collected for a total of nine samples assayed.

The model-optimized variant showed the most GST activity yield followed by CAI-optimized and then wildtype (FIG. 25). CAI-optimized, which has a better codon bias, did not produce as much GST as model-optimized variant. Conversely, the model optimization of gst barely increased codon bias but surpassed the protein yield level of CAI-optimized. Thus, higher codon bias may not always mean higher yield, and CAI is not always an accurate predictor of protein yield as demonstrated by our results and [4,5].

adh was also optimized based on ribosome displacement (model-optimized; see FIG. 26). Wildtype and optimized variants were cloned into pBAD inducible plasmid, expressed in E. coli at 0.2% w/v arabinose for 4 hours, and activity levels compared. ADH activity was measured using E.C. 1.1.1.1 assay. Normalized ADH yield was quantified in units of $\Delta ABS_{340nm}$/min per unit of total protein. Two independent inductions were conducted to test for replicability. From each induction two samples were collected for a total of four samples assayed. Model-optimized variant yielded a 45% increase from wildtype while barely increasing the codon bias (FIG. 27).

Conclusion

We have developed a new model for predicting and optimizing genes for heterologous protein production. The model incorporates an energetic "spring" of 16S rRNA tail and mRNA interactions, ribosome displacement, and tRNA abundance, leading to a ribosome "wait time" parameter for the gene(s) of interest. This represents a comprehensive strategy for evaluating ribosome dynamics and translational efficiency. The model exists as a fully implemented software package (RiboScan™) that provides a new approach to protein production engineering. Applications using the model include: 1) analysis of endogenous E. coli genes and genome annotations, 2) optimization and expression of high value industrial and theurapetic genes that showed poor translation even with codon bias optimization, 3) modifying ribosome "wait time" parameter to optimize protein folding for decreased or elimination of inclusion body formation [6], and 4) expanding the translation model to different production organisms.

REFERENCES

[1] Plotkin, J. B. & Kudla, G. "Synonymous but not the same: the causes and consequences of codon bias." *Nature Reviews Genetics*, 12 (1), 32-42 (2010).

[2] Gustafsson, C., Minshull, J., Govindarajan, S., Ness, J., Villalobos, A., & Welch, M. "Engineering genes for predictable protein expression." *Protein expression and purification*, 83 (1), 37-46, (2012)

[3] Gustafsson, C., Govindarajan, S., & Minshull, J. "Codon bias and heterologous protein expression." *Trends in biotechnology.* 22 (7), 346-353, (2004).

[4] Welch, M., Govindarajan S., Ness J., Villalobos, A., Gurney, A., & Minshul, J. "Design Parameters to Control Synthetic Gene Expression in *Escherichia coli.*" *PLoS one,* 4 (9), e7002, (2009).

[5] Kudla, G., Murray, A. W., Tollervey, D., & Plotkin, J. B. "Coding-sequence determinants of gene expression in *Escherichia coli.*" *Science,* 324 (5924), (2009).

[6] Li, G. W., Oh, E., & Weissman, J. S. "The anti-Shine-Dalgarno sequence drives translational pausing and codon choice in bacteria." *Nature,* 484 (7395), 538-541, (2012).

[7] Allert, M., Cox, J. C., & Hellinga, H. W. "Multifactorial determinants of protein expression in prokaryotic open reading frames." *Journal of molecular biology,* 402 (5), 905-918, (2010).

[8] Sharp, P. M. & Li, W-H. "The codon adaptation index—a measure of directional synonymous codon usage bias, and its potential applications." *Nucleic Acids Res.,* 15 (3), 1281-1295, (1987).

[9] Mishra, M., Vu, S. K., Bitzer, D. L., & Vouk, M. A. "Free energy periodicity in prokaryotic coding and its role in identification of +1 ribosomal frameshifting in the *Escherichia Coli* K-12 gene prfb." $26^{th}$ *Conf. Proc. IEEE EMBS,* Vol 2, pp. 2848-2851, (2004).

[10] Mishra, M. "The Role of Free Energy Synchronous Signal in Translation of Prokaryotes." Thesis. (www.lib.ncsu.edu/resolver/1840.16/1221) (2004).

[11] Rosnick, D., Bitzer, D., Vouk, M., & May, E. "Free energy periodicity in *E. coli* coding." $22^{nd}$ *Conf. Proc IEEE EMBS,* Vol. 4, pp. 2470-2473, (2000).

[12] Dong, H., Nilsson, L., & Kurland, C. G. "Co-variation of tRNA abundance and codon usage in *Escherichia coli* at different growth rates." *Journal of molecular biology.* 260 (5), 649-663, (1996).

[13] Aitken, C. E., Petrov, A., & Puglisi, J. D. "Single ribosome dynamics and the mechanism of translation." *Annu Rev Biophys.,* 39:491-513, (2010).

[14] Larsen, B., Wills, N. M., Gesteland, R. F., & Atkins, J. F. "rRNA-mRNA base pairing stimulates a programmed-1 ribosomal frameshift."*J. Bacteriol.,* 176 (22), 6842-6851, (1994).

[15] Weiss, R. B., Dunn, D. M., Dahlberg, A. E., Atkins, J. F., & Gesteland, R. F. "Reading frame switch caused by base-pair formation between the 3'end of 16S rRNA and the mRNA during elongation of protein synthesis in *Escherichia coli.*" *EMBO. J.,* 7 (5), 1503 (1988).

[16] Freier, S. M., Kierzek, R., Jaeger, J. A., Sugimoto, N., Caruthers, M. H., Nielson, T., & Tuner, D. H. "Improved free-energy parameters for predictions of RNA duplex stability." *Proc. Nat. Acad. Sci. USA,* 83 (24): 9373-9377, (1986).

[17] Ponnala, L., Stomp, A.-M., Bitzer D. L., & Vouk M. A. "Analysis of free energy signals arising from nucleotide hybridization between rRNA and mRNA sequences during translation in Eubacteria." *EURASIP J. on Bioinformatics and Systems Biol.,* pp. 1-9 (23613), (2006).

[18] Ponnala, L., Bitzer, D. L., Stomp, A., & Vouk, M. A. "A computational model for reading frame maintenance." $28^{th}$ *Conf. Proc. IEEE EMBS.* pp. 4540-4543. (2006).

[19] Puigbò, P., Guzmán, E., Romeu, A., & Garcia-Vallvé, S. "OPTIMIZER: a web server for optimizing the codon usage of DNA sequences." *Nucleic acids research,* 35 (suppl 2), W126-W131, (2007).

[20] Shultzaberger, R. K., Bucheimer, R. E., Rudd, K. E., & Schneider, T. D. "Anatomy of *Escherichia coli* ribosome binding sites." *Journal of molecular biology,* 313 (1), 215-228, (2001).

[21] Elf, J., Nilsson, D., Tenson, T., & Ehrenberg, M. "Selective charging of tRNA isoacceptors explains patterns of codon usage." *Science,* 300 (5626): 1718-1722 (2003).

[22] Kimberly, A. D., Sørensen, M. A., Elf, J., Ehrenberg, M., & Pan, T. "Selective charging of tRNA isoacceptors induced by amino-acid starvation." *EMBO reports* 6 (2): 151-157 (2005)

[23] Shine, J. & Dalgamno. L. "The 3'-terminal sequence of *Escherichia coli* 16S ribosomal RNA: complementarity to nonsense triplets and ribosome binding sites," *Proceedings of the National Academy of Sciences,* vol. 71, no. 4, pp. 1342-1346, 1974.

[24] Marshall, R. A., Aitken. C. E. and Puglisi, J. D. "GTP Hydrolysis by IF2 Guides Progression of the Ribosome into Elongation," *Mol. Cell,* vol. 35, no. 1, pp. 37-47, 2009.

[25] Korkmaz, G., Holm, M., Wiens, T. and Sanyal, S. "Comprehensive Analysis of Stop Codon Usage in Bacteria and Its Correlation with Release Factor Abundance," *J. Biol. Chem.,* vol. 289, no. 44, pp. 30334-30342, 2014.

[26] Spirin, A. S. *Ribosomes,* 1st ed. New York, NY: Kluwer Academic/Plenum Publishers, 1999.

[27] Dunkle, J. A., and Cate, J. H. D. "Ribosome structure and dynamics during translocation and termination," *Annu. Rev. Biophys.,* vol. 39, pp. 227-244, 2010.

[28] Sanna, C. R. Li, W.-H., and Zhang, L. "Overlapping genes in the human and mouse genomes," *BMC Genomics,* vol. 9, p. 169, 2008

[29] Fukuda, Y., Nakayama, Y., and Tomita, M. "On dynamics of overlapping genes in bacterial genomes," *Gene,* vol. 323, no. 1-2, pp. 181-187, 2003.

[30] Li, G. W., Oh, E. and Weissman, J. S. "The anti-Shine-Dalgarno sequence drives translational pausing and codon choice in bacteria," *Nature,* vol. 484, no. 7395, pp. 538-541, 2012.

[31] Farabaugh, P. J. "Programmed translational frameshifting," *Annu. Rev. Genet.,* vol. 30, pp. 507-528, 1996

[32] Tinoco, I. Kim, H. K. and Yan, S. "Frameshifting dynamics," *Biopolymers,* vol. 99, no. 12, pp. 1147-1166, 2013.

[33] Weiss, R. B., Dunn, D. M., Dahlberg, A. E., Atkins, J. F., and Gesteland, R. F. "Reading frame switch caused by base-pair formation between the 3' end of 16S rRNA and the mRNA during elongation of protein synthesis in *Escherichia coli,"EMBO. J.,* vol. 7, no. 5, pp. 1503-1507, 1988.

[34] Larsen, B., Wills, N. M., Gesteland, R. F., and Atkins, J. F. "rRNA-mRNA base pairing stimulates a programmed-1 ribosomal frameshift," *J. Bacteriol.,* vol. 176, no. 22, pp. 6842-6851, 1994.

[35] Salis, H. M., Mirsky, E. A., and Voigt, C. A. "Automated design of synthetic ribosome binding sites to control protein expression," *Nat. Biotechnol.,* vol. 27, no. 10, pp. 946-950, 2009.

[36] Sharp, P. M., and Li, W.-H. "The codon adaptation index—a measure of directional synonymous codon usage bias, and its potential applications," *Nucleic Acids Res.,* vol. 15, no. 3, pp. 1281-1295, 1987.

[37] dos Reis, M., Savva, R., and Wernisch, L., "Solving the riddle of codon usage preferences: a test for translational selection," *Nucleic Acids Res.,* vol. 32, no. 17, pp. 5036-5044, 2004

[38] Welch, M., Govindarajan, S., Ness, J. E., Villalobos, A., Gurney, A., Minshull, J., and Gustafsson, C. "Design Parameters to Control Synthetic Gene Expression in *Escherichia coli,*" *PLoS ONE*, vol. 4, no. 9, p. e7002, 2009.

[39] Gustafsson, C., Govindarajan, S., and Minshull, J. "Codon bias and heterologous protein expression," *Trends in Biotechnology*, vol. 22, no. 7. pp. 346-353, 2004.

[40] Puigbò, P., Guzmán, E., Romeu, A., and Garcia-Vallvé, S. "OPTIMIZER: A web server for optimizing the codon usage of DNA sequences," *Nucleic Acids Res.*, vol. 35, no. SUPPL.2, 2007.

[41] Grote, A., Hiller, K., Scheer, M., Münch, R., Nortemann, B., Hempel, D. C., and Jahn, D. "JCat: A novel tool to adapt codon usage of a target gene to its potential expression host," *Nucleic Acids Res.*, vol. 33, no. SUPPL. 2, 2005.

[42] Vu, S. K., Bellotti, A. A., Gabriel, C. J., Brochu, H. N., Miller, E. S., Bitzer, D. L., and Vouk, M. A "Modeling ribosome dynamics to optimize heterologous protein production in *Escherichia coli,*" *IEEE Global Conference on Signal and Information Processing (GlobalSIP)*, pp. 1422-1425, 2014.

[43] Shultzaberger, R. K., Bucheimer, R. E., Rudd, K. E., and Schneider, T. D. "Anatomy of *Escherichia coli* ribosome binding sites," *J. Mol. Bio.*, vol. 313, no. 1, pp. 215-228, 2001.

[44] Tinoco, I., Kim, H.-K., and Yan, S. "Frameshifting dynamics," *Biopolymers*, vol. 99, no. 12, pp. 1147-1166, 2013.

[45] M. Mishra, S. K. Vu, D. L. Bitzer, and M. a Vouk, "Free energy periodicity in prokaryotic coding and its role in identification of +1 ribosomal frameshifting in the *Escherichia Coli* K-12 gene prfb," *Conf. Proc. IEEE Eng. Med. Biol. Soc.*, vol. 4, pp. 2848-2851, 2004.

[46] D. I. Rosnick, D. L. Bitzer, M. A. Vouk, and E. E. May, "Free energy periodicity in *E. coli* coding," *Conf. Proc. IEEE Eng. Med. Biol. Soc.*, vol. 4, pp. 2470-2473, 2000.

[47] M. Mishra, "The Role of Free Energy Synchronization Signal in Translation of Prokaryotes," M. S. thesis, Dept. Comp. Sci., N. C. State Univ., Raleigh, NC, 2004.

[48] L. Ponnala, A. M. Stomp, D. L. Bitzer, and M. A. Vouk, "Analysis of free energy signals arising from nucleotide hybridization between rRNA and mRNA sequences during translation in eubacteria," *Eurasip J. Bioinforma. Syst. Biol.*, vol. 2006, 2006.

[49] G. W. Li, E. Oh, and J. S. Weissman, "The anti-Shine-Dalgarno sequence drives translational pausing and codon choice in bacteria," *Nature*, vol. 484, no. 7395, pp. 538-541, 2012

[50] R. B. Weiss, D. M. Dunn, A. E. Dahlberg, J. F. Atkins, and R. F. Gesteland, "Reading frame switch caused by base-pair formation between the 3'end of 16S rRNA and the mRNA during elongation of protein synthesis in *Escherichia coli,*" *EMBO J.*, vol. 7, no. 5, p. 1503, 1988.

[51] B. Larsen, N. M. Wills, R. F. Gesteland, and J. F. Atkins, "rRNA-mRNA base pairing stimulates a programmed-1 ribosomal frameshift,"*J. Bacteriol.*, vol. 176, no. 22, pp. 6842-6851, 1994.

[52] L. Ponnala, D. L. Bitzer, A. Stomp, and M. A. Vouk, "A computational model for reading frame maintenance," *Conf. Proc. IEEE Eng. Med. Biol. Soc.,* 2006, pp. 4540-4543.

[53] S. K. Vu, A. A. Bellotti, C. J. Gabriel, H. N. Brochu, E. S. Miller, D. L. Bitzer, and M. A. Vouk, "Modeling ribosome dynamics to optimize heterologous protein production in *Escherichia coli,"* *IEEE Global Conference on Signal and Information Processing (GlobalSIP)*, pp. 1422-1425, 2014.

[54] I. Tinoco, H. K. Kim, and S. Yan, "Frameshifting dynamics," *Biopolymers*, vol. 99, no. 12, pp. 1147-1166, 2013.

[55] H. Chen, M. Bjerknes, R. Kumar, and E. Jay, "Determination of the optimal aligned spacing between the Shine-Dalgarno sequence and the translation initiation codon of *Escherichia coli* m RNAs." *Nucleic Acids Res.*, vol. 22, no. 23, pp 4953-4957, 1994.

[56] R. K. Shultzaberger, R. E. Bucheimer, K. E. Rudd, and T. D. Schneider, "Anatomy of *Escherichia coli* ribosome binding sites," *J. Mol. Bio.*, vol. 313, no. 1, pp. 215-228, 2001.

[57] N. Malys, "Shine-Dalgarno sequence of bacteriophage T4: GAGG prevails in early genes," *Mol. Biol. Rep.*, vol. 39, no. 1, pp. 33-39, 2011.

[58] P. J. Farabaugh, "Programmed translational frameshifting," *Annu. Rev. Genet.*, vol. 30, pp. 507-528, 1996.

[59] P. V. Baranov, R. F. Gesteland, and J. F. Atkins, "Release factor 2 frameshifting sites in different bacteria," *EMBO Rep.*, vol. 3, no. 4, pp. 373-377, 2002.

[60] J. Elf and M. Ehrenberg, "Near-Critical Behavior of Aminoacyl-tRNA Pools in *E. coli* at Rate-Limiting Supply of Amino Acids," *Biophys. J.*, vol. 88, no. 1, pp. 132-146, 2005.

[61] M. Welch, S. Govindarajan, J. E. Ness, A. Villalobos, A. Gurney, J. Minshull, and C. Gustafsson, "Design Parameters to Control Synthetic Gene Expression in *Escherichia coli,"* *PLoS ONE*, vol. 4, no. 9, p. e7002, 2009.

[62] K. A. Dittmar, M. A. Sørensen, J. Elf, M. ans Ehrenberg, and T. Pan, "Selective charging of tRNA isoacceptors induced by amino-acid starvation," *EMBO Rep.*, vol. 6, no. 2, pp. 151-157, 2005.

[63] M. A. Sørensen, "Charging levels of four tRNA species in *Escherichia coli* Rel(+) and Rel(-) strains during amino acid starvation: a simple model for the effect of ppGpp on translational accuracy," *J. Mol. Biol.*, vol. 307, no. 3, pp. 785-798, 2001.

[64] H. Dong, L. Nilsson, and C. G. Kurland, "Co-variation of tRNA abundance and codon usage in *Escherichia coli* at different growth rates,"*J. Mol. Biol.*, vol. 260, no. 5, pp. 649-663, 1996.

[65] F. H. Crick, "Codon-anticodon pairing: the wobble hypothesis," *J. Mol. Biol.*, vol. 19, no. 2, pp. 548-555, 1966.

[66] S. K. Vu, 'RiboLab Research Group', *Ribolab.com,* 2015. [Online]. Available: http://www.ribolab.com. [Accessed: 5 Aug. 2015].

[67] A. S. Spirin, Ribosomes, 1st ed. New York, NY: Kluwer Academic/Plenum Publishers, 1999.

[86] M. Mishra, S. K. Vu, D. L. Bitzer, and M. a Vouk, "Free energy periodicity in prokaryotic coding and its role in identification of +1 ribosomal frameshifting in the *Escherichia Coli* K-12 gene prfb," *Conf. Proc. IEEE Eng. Med. Biol. Soc* . . . vol. 4, pp. 2848-2851, 2004.

[69] D. I. Rosnick, D. L. Bitzer, M. A. Vouk, and E. E. May, "Free energy periodicity in *E. coli* coding," *Proc. 22nd Annu. Int. Conf. IEEE Eng. Med. Biol. Soc.*, vol. 4, pp. 2470-2473, 2000.

[70] A. S. Spirin, *Ribosomes,* 1st ed. New York, NY: Kluwer Academic/Plenum Publishers, 1999.

[71] S. M. Freier, R. Kierzek, J. A. Jaeger, N. Sugimoto, M. H. Caruthers, T. Neilson, and D. H. Turner, "Improved

[72] H. Chen, M. Bjerknes, R. Kumar, and E. Jay, "Determination of the optimal aligned spacing between the Shine-Dalgarno sequence and the translation initiation codon of *Escherichia coli* m RNAs," *Nucleic Acids Res.*, vol. 22, no. 23, pp. 4953-4957, 1994.

[73] D. I. Rosnick, D. L. Bitzer, M. A. Vouk, and E. E. May, "Free energy periodicity in *E. coli* coding," *Conf. Proc. IEEE Eng. Med. Biol. Soc.*, vol. 4, pp. 2470-2473, 2000.

[74] L. Ponnala, A. M. Stomp, D. L. Bitzer, and M. A. Vouk, "Analysis of free energy signals arising from nucleotide hybridization between rRNA and mRNA sequences during translation in eubacteria," *Eurasip J. Bioinforma. Syst. Biol.*, vol. 2006, 2006.

[75] H. Dong, L. Nilsson, and C. G. Kurland, "Co-variation of tRNA abundance and codon usage in *Escherichia coli* at different growth rates," *J. Mol. Biol.*, vol. 260, no. 5, pp. 649-663, 1996.

[76] T. Ikemura, "Correlation between the abundance of yeast transfer RNAs and the occurrence of the respective codons in protein genes: differences in synonymous codon choice patterns of yeast and *Escherichia coli* with reference to the abundance of isoaccepting transfer RNAs,".*J. Mol. Biol.*, vol. 158, no. 4, pp. 573-597, 1982.

[77] T. Ikemura, "Codon usage and tRNA content in unicellular and multicellular organisms," *Mol. Biol. Evol.*, vol. 2, no. 1, pp. 13-34, 1985.

[78] T. Ikemura, "Correlation between the abundance of *Escherichia coli* transfer RNAs and the occurrence of the respective codons in its protein genes: a proposal for a synonymous codon choice that is optimal for the *E. coli* translational system,".*J. Mol. Biol.*, vol. 151, no. 3, pp. 389-409, 1981.

[79] S. Kanaya, Y. Yamada, Y. Kudo, and T. Ikemura, "Studies of codon usage and tRNA genes of 18 unicellular organisms and quantification of *Bacillus subtilis* tRNAs: gene expression level and species-specific diversity of codon usage based on multivariate analysis," *Gene*, vol. 238, no. 1, pp. 143-155, 1999.

[80] L. Duret, "tRNA gene number and codon usage in the *C. elegans* genome are co-adapted for optimal translation of highly expressed genes," *Trends in Genetics*, vol. 16, no. 7. pp. 287-289, 2000.

[81] R. Percudani, A. Pavesi, and S. Ottonello, "Transfer RNA gene redundancy and translational selection in *Saccharomyces cerevisiae*," *J Mol. Biol.*, vol. 268, no. 2, pp. 322-330, 1997.

[82] M. dos Reis, R. Savva, and L. Wernisch, "Solving the riddle of codon usage preferences: a test for translational selection," *Nucleic Acids Res.*, vol. 32, no. 17, pp. 5036-5044, 2004.

[83] Y. Nakamura, T. Gojobori, and T. Ikemura, "Codon usage tabulated from international DNA sequence databases: status for the year 2000," *Nucleic Acids Res*, vol. 28, p. 292, 2000.

[84] M. Mishra, "The Role of Free Energy Synchronization Signal in Translation of Prokaryotes," M. S. thesis, Dept. Comp. Sci., N. C. State Univ., Raleigh, NC, 2004.

[85] S. K. Vu, 'RiboLab Research Group', *Ribolab.com*, 2015 [Online]. Available: http://www.ribolab.com. [Accessed: 5 Aug. 2015].

[86] P. M. Sharp and W. H. Li, "The codon adaptation index—a measure of directional synonymous codon usage bias, and its potential applications," *Nucleic Acids Res.*, vol. 15, no. 3, pp. 1281-1295, 1987.

[87] H. R. Costantino, S. H. Brown, and R. M. Kelly, "Purification and characterization of an α-glucosidase from a hyperthermophilic archaebacterium, *Pyrococcus furiosus*, exhibiting a temperature optimum of 105 to 115° C.," *J. Bacteriol.*, vol. 172, no. 7, pp. 3654-3660, 1990.

[88] P. L. Møller, F. Jørgensen, O. C. Hansen, M. Madsen, P. Stougaard, O. L. E. C. Hansen, and S. M. Madsen, "Intra- and Extracellular b-galactosidases from *Bifidobacterium bifidum* and *B. infantis*: Molecular Cloning, Heterologous Expression, and Comparative Characterization," *Appl. Environ. Microbiol.*, vol. 67, no. 5, pp. 2276-2283, 2001.

[89] H. Dong, L. Nilsson, and C. G. Kurland, "Co-variation of tRNA Abundance and Codon Usage in *Escherichia coli* at Different Growth Rates," *J. Mol. Biol.*, vol. 260, no. 5, pp. 649-663, 1996.

[90] H. M. Salis, "The ribosome binding site calculator," *Methods Enzymol.*, vol. 498, pp. 19-42, 2011.

[91] P. Puigbò, E. Guzmán, A. Romeu, and S. Garcia-Vallvé, "OPTIMIZER: A web server for optimizing the codon usage of DNA sequences," *Nucleic Acids Res.*, vol. 35, no. SUPPL.2, 2007.

[92] D. B. Smith, K. M. Davern, P. G. Board, W. U. Tiu, E. G. Garcia, and G. F. Mitchell, "Mr 26,000 antigen of *Schistosoma japonicum* recognized by resistant WEHI 129/J mice is a parasite glutathione S-transferase," *Proc. Natl. Acad. Sci. U.S.A*, vol. 83, no. 22, pp. 8703-8707, 1986.

[93] S. K. Vu, A. A. Bellotti, C. J. Gabriel, H. N. Brochu, E. S. Miller, D. L. Bitzer, and M. A. Vouk, "Modeling ribosome dynamics to optimize heterologous protein production in *Escherichia coli*," *IEEE Global Conference on Signal and Information Processing (GlobalSIP)*, pp. 1422-1425, 2014.

[94] Y. Nakamura, T. Gojobori, and T. Ikemura, "Codon usage tabulated from international DNA sequence databases: status for the year 2000," *Nucleic Acids Res*, vol. 28, p. 292, 2000

[95] L. M. Guzman, D. Belin, M. J. Carson, and J. Beckwith, "Tight regulation, modulation, and high-level expression by vectors containing the arabinose P(BAD) promoter," *J. Bacteriol.*, vol. 177, no. 14, pp. 4121-4130, 1995.

[96] E. Siller, D. C. DeZwaan, J. F. Anderson, B. C. Freeman, and J. M. Barral, "Slowing Bacterial Translation Speed Enhances Eukaryotic Protein Folding Efficiency," *J. Mol. Biol.*, vol. 396, no. 5, pp. 1310-1318, 2010.

[97] S. Pechmann and J. Frydman, "Evolutionary conservation of codon optimality reveals hidden signatures of cotranslational folding," *Nat. Struct. Mol. Biol.*, vol. 20, no 2, pp 237-243, 2013.

[98] G. W. Li, E. Oh, and J. S. Weissman, "The anti-Shine-Dalgarno sequence drives translational pausing and codon choice in bacteria," *Nature*, vol. 484, no. 7395, pp. 538-541, 2012.

[99] BiologicsCorp, 'GC Content Calculator', Biologicscorp.com, 2015. [Online]. Available: http://www.biologicscorp.com/tools/GCContent. [Accessed: 22 Aug. 2015].

[100] Y. Nakamura, T. Gojobori, and T. Ikemura, "Codon usage tabulated from international DNA sequence databases: status for the year 2000." *Nucleic Acids Res*, vol. 28, p. 292, 2000

[101] D. A. Benson, I. Karsch-Mizrachi, D. J. Lipman, J. Ostell, and E. W. Sayers, "GenBank," *Nucleic Acids Res.*, vol. 39, no. SUPPL. 1, 2011.

[102] M. Welch, S. Govindarajan, J. E. Ness, A. Villalobos, A. Gurney, J. Minshull, and C. Gustafsson, "Design Parameters to Control Synthetic Gene Expression in *Escherichia coli*," *PLoS ONE*, vol. 4, no. 9, p. e7002, 2009.

[103] K. A. Dittmar, M. A. Sørensen, J. Elf. M. ans Ehrenberg, and T. Pan, "Selective charging of tRNA isoacceptors induced by amino-acid starvation," *EMBO Rep.*, vol. 6, no. 2, pp. 151-157, 2005.

[104] J. Elf and M. Ehrenberg, "Near-Critical Behavior of Aminoacyl-tRNA Pools in *E. coli* at Rate-Limiting Supply of Amino Acids," *Biophys. J.*, vol. 88, no. 1, pp. 132-146, 2005.

[105] C. Gustafsson, S. Govindarajan, and J. Minshull, "Codon bias and heterologous protein expression," *Trends in Biotechnology*, vol. 22, no. 7. pp. 346-353, 2004.

[106] M. Welch, A. Villalobos, C. Gustafsson, and J. Minshull, "Designing genes for successful protein expression," *Methods Enzymol.*, vol. 498, pp. 43-66, 2011.

[107] B. Maertens, A. Spriestersbach, U. Von Groll, U. Roth, J. Kubicek, M. Gerrits, M. Graf, M. Liss, D. Daubert, R. Wagner, and F. Schäfer, "Gene optimization mechanisms: A multi-gene study reveals a high success rate of full-length human proteins expressed in *Escherichia coli*," *Protein Sci.*, vol. 19, no. 7, pp. 1312-1326, 2010.

[108] N. A. Burgess-Brown, S. Sharma, F. Sobott, C. Loenarz, U. Oppermann, and O. Gileadi, "Codon optimization can improve expression of human genes in *Escherichia coli*: A multi-gene study," *Protein Expr. Purif.*, vol. 59, no. 1, pp. 94-102, 2008.

[109] H. G. Menzella, "Comparison of two codon optimization strategies to enhance recombinant protein production in *Escherichia coli*," *Microb. Cell Fact.*, vol. 10, no. 1, p. 15, 2011.

[110] F. Baneyx and M. Mujacic, "Recombinant protein folding and misfolding in *Escherichia coli*," *Nat. Biotechnol.*, vol. 22, no. 11, pp. 1399-1408, 2004.

[111] A. Mitraki and J. King, "Protein Folding Intermediates and Inclusion Body Formation," *Nat. Biotechnol.*, vol. 7, pp. 690-697, 1989.

[112] S. Kim and S. B. Lee, "Soluble expression of archaeal proteins in *Escherichia coli* by using fusion-partners," *Protein Expr. Purif.*, vol. 62, no. 1, pp. 116-119, 2008.

[113] S. V. Albers, M. Jonuscheit, S. Dinkelaker, T. Urich, A. Kletzin, R. Tampé, A. J. M. Driessen, and C. Schleper, "Production of recombinant and tagged proteins in the hyperthermophilic archaeon *Sulfolobus solfataricus*," *Appl. Environ. Microbiol.*, vol. 72, no. 1, pp. 102-111, 2006.

[114] M. Allert, J. C. Cox, and H. W. Hellinga, "Multifactorial Determinants of Protein Expression in Prokaryotic Open Reading Frames," *J. Mol. Biol.*, vol. 402, no. 5, pp. 905-918, 2010.

[115] G. Kudla, A. W. Murray, D. Tollervey, and J. B. Plotkin, "Coding-sequence determinants of gene expression in *Escherichia coli*," Science, vol. 324, no. 5924, pp. 255-258, 2009

[116] I. Tinoco, H. K. Kim, and S. Yan, "Frameshifting dynamics," *Biopolymers*, vol. 99, no. 12, pp. 1147-1166, 2013.

[117] E. Siller, D. C. DeZwaan, J. F. Anderson, B. C. Freeman, and J. M. Barral, "Slowing Bacterial Translation Speed Enhances Eukaryotic Protein Folding Efficiency," *J. Mol. Biol.*, vol. 396, no. 5, pp. 1310-1318, 2010.

[118] S. Pechmann and J. Frydman, "Evolutionary conservation of codon optimality reveals hidden signatures of cotranslational folding," *Nat. Struct. Mol. Biol.*, vol. 20, no. 2, pp. 237-243, 2013.

[119] A. Mitraki and J. King, "Protein Folding Intermediates and Inclusion Body Formation," *Nat. Biotechnol.*, vol. 7, pp. 690-697, 1989.

[120] F. Baneyx and M. Mujacic, "Recombinant protein folding and misfolding in *Escherichia coli*," *Nat. Biotechnol.*, vol. 22, no. 11, pp. 1399-1408, 2004.

[121] C. Xing, D. L. Bitzer, W. E. Alexander, A. M. Stomp, and M. A. Vouk, "Free energy analysis on the coding region of the individual genes of *Saccharomyces cerevisiae*," *Conf Proc IEEE Eng Med Biol Soc*, vol. 1, pp 4225-4228, 2006.

[122] C. Xing, D. L. Bitzer, W. E. Alexander, M. a Vouk, and A.-M. Stomp, "Identification of protein-coding sequences using the hybridization of 18S RNA and mRNA during translation.," *Nucleic Acids Res.*, vol. 37, no. 2, pp. 591-601, 2009.

[123] C. Xing, "Methods of identification of pseudogenes based on functionality: hybridization of 18S rRNA and mRNA during translation," *Methods Mol Biol*, vol. 1167, pp. 63-73, 2014.

[124] A. V Pisarev, V. G. Kolupaeva, M. M. Yusupov, C. U. T. Hellen, and T. V Pestova, "Ribosomal position and contacts of mRNA in eukaryotic translation initiation complexes.," *EMBO J.*, vol. 27, pp. 1609-1621, 2008.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

INCORPORATION-BY-REFERENCE OF
MATERIAL SUBMITTED ELECTRONICALLY

This application contains a sequence listing. It has been submitted electronically via EFS-Web as an AS CII text file entitled 908_21_2_UTIL_SL.txt. The sequence listing is 3,098 bytes in size, and was created on Aug. 10, 2023. It is hereby incorporated by reference in its entirety.

That which is claimed:

1. A method for increasing protein yield by determining an optimized nucleotide sequence encoding a protein and expressing the optimized nucleotide sequence in a host cell, the method comprising:
   (a) determining ribosome wait time at each codon in a coding region of an mRNA encoding the protein, comprising determining a number of cycles at each codon, wherein determining the number of cycles at each codon comprises determining ribosome displacement at each codon using a step size function convolved with probabilities of picking up or not picking up an aa-tRNA, wherein the step size function is determined as the force at the current ribosome displacement multiplied by a step size constant (dT), wherein determined ribosome displacement repeats in a probability cycle until the ribosome has picked up an aa-tRNA, wherein the number of cycles is a function of tRNA abundance, ribosome displacement magnitude, and force from binding between the mRNA and a 3' terminal rRNA tail of a ribosome;
   (b) determining a total cycle count across codons throughout the coding region;
   (c) producing an optimized nucleotide sequence, wherein producing the optimized nucleotide sequence includes modifying codons using synonymous codons that conserve the protein amino acid sequence while changing the force and/or the wait time, and wherein changing the force and/or wait time includes minimizing the ribosome displacement magnitude by selecting a phase angle of the optimized nucleotide sequence that is substantially equal to a species angle of the host cell;
   (d) introducing an expression vector comprising the optimized nucleotide sequence into the host cell or introducing the optimized nucleotide sequence into the chromosome of the host cell; and
   (e) expressing the optimized nucleotide sequence encoding the protein in the host cell;
   wherein the protein yield of the protein is increased.

2. The method of claim 1, wherein the host cell is a eukaryotic organism and the 3' terminal rRNA tail of the ribosome is an 18S rRNA tail.

3. The method of claim 1, wherein the host cell is a prokaryotic organism and the 3' terminal rRNA tail of the ribosome is an 16S rRNA tail.

4. A method for increasing protein yield by determining an optimized nucleotide sequence encoding a protein and expressing the optimized nucleotide sequence in a host cell, the method comprising:
   (a) determining ribosome wait time at each codon in a coding region of an mRNA encoding the protein, comprising determining a number of cycles at each codon, wherein determining the number of cycles at each codon comprises determining ribosome displacement at each codon using a step size function convolved with probabilities of picking up or not picking up an aa-tRNA, wherein the step size function is determined as the force at the current ribosome displacement multiplied by a step size constant (dT), wherein determined ribosome displacement repeats in a probability cycle until the ribosome has picked up an aa-tRNA, wherein the number of cycles is a function of tRNA abundance, ribosome displacement magnitude, and force from binding between the mRNA and a 3' terminal rRNA tail of a ribosome;
   (b) determining a total cycle count across codons throughout the coding region;
   (c) producing an optimized nucleotide sequence, wherein producing the optimized nucleotide sequence includes modifying codons using synonymous codons that conserve the protein amino acid sequence while changing the force and/or the wait time, and wherein changing the force and/or wait time includes minimizing the ribosome displacement magnitude by selecting a phase angle of the optimized nucleotide sequence that is substantially equal to a species angle of the host cell;
   (d) introducing an expression vector comprising the optimized nucleotide sequence into the host cell or introducing the optimized nucleotide sequence into the chromosome of the host cell; and
   (e) expressing the optimized nucleotide sequence encoding the protein in the host cell;
   wherein the protein yield of the protein is decreased.

5. The method of claim 4, wherein the host cell is a eukaryotic organism and the 3' terminal rRNA tail of the ribosome is an 18S rRNA tail.

6. The method of claim 4, wherein the host cell is a prokaryotic organism and the 3' terminal rRNA tail of the ribosome is an 16S rRNA tail.

* * * * *

SEQUENCE LISTING

<160> NUMBER OF SEQ ID NOS: 17

<210> SEQ ID NO 1

-continued

```
<211> LENGTH: 26
<212> TYPE: RNA
<213> ORGANISM: Escherichia coli

<400> SEQUENCE: 1
ccgcccguca caccauggag uggguu                                          26

<210> SEQ ID NO 2
<211> LENGTH: 69
<212> TYPE: RNA
<213> ORGANISM: Escherichia coli

<400> SEQUENCE: 2
auuccuccac agguuggcg uccaaagggg augccaaugg aacaaugcug aagugggguc      60
aguacuuag                                                             69

<210> SEQ ID NO 3
<211> LENGTH: 21
<212> TYPE: RNA
<213> ORGANISM: Escherichia coli

<400> SEQUENCE: 3
aagcgggagg cauggaaacc c                                               21

<210> SEQ ID NO 4
<211> LENGTH: 13
<212> TYPE: RNA
<213> ORGANISM: Escherichia coli

<400> SEQUENCE: 4
auuccuccac uag                                                        13

<210> SEQ ID NO 5
<211> LENGTH: 22
<212> TYPE: RNA
<213> ORGANISM: Escherichia coli

<400> SEQUENCE: 5
ucuuaggggg uaucuuugac ua                                              22

<210> SEQ ID NO 6
<211> LENGTH: 24
<212> TYPE: RNA
<213> ORGANISM: Escherichia coli

<400> SEQUENCE: 6
uuuccggcac cagaagcggu gccg                                            24

<210> SEQ ID NO 7
<211> LENGTH: 12
<212> TYPE: RNA
<213> ORGANISM: Escherichia coli

<400> SEQUENCE: 7
ucacguacgg cg                                                         12

<210> SEQ ID NO 8
<211> LENGTH: 11
<212> TYPE: RNA
<213> ORGANISM: Escherichia coli

<400> SEQUENCE: 8
ucaguacggc g                                                          11
```

<210> SEQ ID NO 9
<211> LENGTH: 21
<212> TYPE: RNA
<213> ORGANISM: Escherichia coli

<400> SEQUENCE: 9
aagcgggaug caugguugcc c    21

<210> SEQ ID NO 10
<211> LENGTH: 24
<212> TYPE: RNA
<213> ORGANISM: Escherichia coli

<400> SEQUENCE: 10
uuuccggcac cagaagcucc ggcg    24

<210> SEQ ID NO 11
<211> LENGTH: 14
<212> TYPE: RNA
<213> ORGANISM: Escherichia coli

<400> SEQUENCE: 11
auuaccucca cuag    14

<210> SEQ ID NO 12
<211> LENGTH: 14
<212> TYPE: RNA
<213> ORGANISM: Escherichia coli

<400> SEQUENCE: 12
gaucaccucc auua    14

<210> SEQ ID NO 13
<211> LENGTH: 27
<212> TYPE: RNA
<213> ORGANISM: Escherichia coli

<400> SEQUENCE: 13
ccgcccguca caccauggga gugggyu    27

<210> SEQ ID NO 14
<211> LENGTH: 68
<212> TYPE: RNA
<213> ORGANISM: Escherichia coli

<400> SEQUENCE: 14
gauucaugac uggggugaag ucguaacaag guaaccguag gggaaccugc gguuggauca    60
ccuccuua    68

<210> SEQ ID NO 15
<211> LENGTH: 18
<212> TYPE: RNA
<213> ORGANISM: Escherichia coli

<400> SEQUENCE: 15
aagcgggagg cauggaaa    18

<210> SEQ ID NO 16
<211> LENGTH: 13
<212> TYPE: RNA
<213> ORGANISM: Escherichia coli

```
<400> SEQUENCE: 16
gaucaccucc uua                                                              13

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xhis

<400> SEQUENCE: 17

His His His His His His
1               5
```